(12) United States Patent
Romagnoli et al.

(10) Patent No.: US 10,744,293 B2
(45) Date of Patent: Aug. 18, 2020

(54) PATIENT INTERFACE

(71) Applicant: ResMed Pty Ltd, Bella Vista, New South Wales (AU)

(72) Inventors: Jose Ignacio Romagnoli, Sydney (AU); Errol Savio Alex D'Souza, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 0 days.

(21) Appl. No.: 16/270,731

(22) Filed: Feb. 8, 2019

(65) Prior Publication Data

US 2019/0290878 A1 Sep. 26, 2019

Related U.S. Application Data

(63) Continuation of application No. 14/717,238, filed on May 20, 2015, now Pat. No. 10,232,137.

(Continued)

(51) Int. Cl.
*A61M 16/10* (2006.01)
*A61M 16/00* (2006.01)
(Continued)

(52) U.S. Cl.
CPC .... *A61M 16/1045* (2013.01); *A61M 16/0057* (2013.01); *A61M 16/06* (2013.01);
(Continued)

(58) Field of Classification Search
CPC .......... A61M 16/1045; A61M 16/0633; A61M 16/0057; A61M 16/06; A61M 16/0683;
(Continued)

(56) References Cited

U.S. PATENT DOCUMENTS 4,782,832 A 11/1988 Trimble et al.
4,944,310 A 7/1990 Sullivan
(Continued)

FOREIGN PATENT DOCUMENTS

GB 2 379 886 3/2003
NZ 581715 3/2010
(Continued)

OTHER PUBLICATIONS

First Examination Report issued in corresponding New Zealand Appln. No. 625846 dated Jun. 10, 2014.
(Continued)

*Primary Examiner* — Andrew S Lo
(74) *Attorney, Agent, or Firm* — Nixon & Vanderhye P.C.

(57) ABSTRACT

A patient interface for delivery of a supply of pressurised air or breathable gas to an entrance of a patient's airways includes a frame member, a cushion assembly provided to the frame member, and an anterior wall member repeatedly engageable with and disengageable from the cushion assembly. The frame member includes connectors operatively attachable to a positioning and stabilizing structure. The cushion assembly includes a seal-forming structure and a void defined by an anterior surface of the cushion assembly. The anterior wall member has a predetermined surface area to seal the void of the cushion assembly and form a gas chamber when the anterior wall member and the cushion assembly are engaged. The void of the cushion assembly is sized such that the patient's nose and/or mouth is substantially exposed when the anterior wall member is disengaged from the cushion assembly thereby improving breathing comfort of the patient.

20 Claims, 65 Drawing Sheets

Related U.S. Application Data

(60) Provisional application No. 62/001,944, filed on May 22, 2014.

(51) Int. Cl.
*A61M 16/06* (2006.01)
*A61M 16/08* (2006.01)
*A61M 16/16* (2006.01)

(52) U.S. Cl.
CPC .... *A61M 16/0633* (2014.02); *A61M 16/0683* (2013.01); *A61M 16/08* (2013.01); *A61M 16/0816* (2013.01); *A61M 16/0875* (2013.01); *A61M 16/10* (2013.01); *A61M 16/107* (2014.02); *A61M 16/1055* (2013.01); *A61M 16/16* (2013.01); *A61M 2205/0272* (2013.01)

(58) Field of Classification Search
CPC .............. A61M 16/08; A61M 16/0816; A61M 16/0875; A61M 16/107; A61M 16/10; A61M 16/1055; A61M 16/16; A61M 2205/0272
USPC .................................................. 128/206.24
See application file for complete search history.

(56) References Cited

U.S. PATENT DOCUMENTS

| | | | |
|---|---|---|---|
| 6,240,921 B1 | 6/2001 | Brydon et al. | |
| 6,532,959 B1 | 3/2003 | Berthon-Jones | |
| 6,581,594 B1 | 6/2003 | Drew et al. | |
| 6,629,527 B1* | 10/2003 | Estes | A61M 16/024 128/202.22 |
| 6,823,869 B2 | 11/2004 | Raje | |
| 6,951,218 B2 | 10/2005 | Gradon | |
| 7,047,971 B2 | 5/2006 | Ho | |
| 7,066,179 B2* | 6/2006 | Eaton | A61M 16/0683 128/202.27 |
| 7,069,932 B2* | 7/2006 | Eaton | A61M 16/06 128/206.21 |
| 7,234,466 B2* | 6/2007 | Kwok | A61M 16/06 128/207.11 |
| 7,287,528 B2* | 10/2007 | Ho | A61M 16/0616 128/206.21 |
| 7,290,546 B2 | 11/2007 | Sprinkle | |
| 7,318,439 B2 | 1/2008 | Raje | |
| 7,455,063 B2* | 11/2008 | Geiselhart | A61M 16/06 128/205.25 |
| 7,610,916 B2* | 11/2009 | Kwok | A61M 16/06 128/207.11 |
| 7,621,274 B2* | 11/2009 | Sprinkle | A61M 16/06 128/206.21 |
| 7,793,987 B1* | 9/2010 | Busch | A61M 16/0816 285/9.1 |
| 7,958,893 B2* | 6/2011 | Lithgow | A61M 16/06 128/206.24 |
| 8,042,542 B2* | 10/2011 | Ging | A44B 11/266 128/200.24 |
| 8,051,855 B2* | 11/2011 | Ho | A61M 16/06 128/206.21 |
| 9,044,564 B2* | 6/2015 | Dravitzki | A61M 16/0683 |
| 9,149,593 B2* | 10/2015 | Dravitzki | A61M 16/0683 |
| 2001/0017134 A1 | 8/2001 | Von Bahr | |
| 2005/0121030 A1 | 6/2005 | Bateman et al. | |
| 2005/0155604 A1* | 7/2005 | Ging | A61M 16/0875 128/206.21 |
| 2009/0044808 A1 | 2/2009 | Guney et al. | |
| 2009/0050156 A1 | 2/2009 | Ng et al. | |
| 2009/0217929 A1 | 9/2009 | Kwok | |
| 2010/0000534 A1 | 1/2010 | Kooij et al. | |
| 2010/0229868 A1* | 9/2010 | Rummery | A61M 16/06 128/205.25 |
| 2011/0023874 A1 | 2/2011 | Bath et al. | |
| 2011/0259337 A1* | 10/2011 | Hitchcock | A61M 16/0875 128/207.11 |
| 2012/0017912 A1* | 1/2012 | Ging | A61M 16/0683 128/207.11 |
| 2012/0090617 A1* | 4/2012 | Matula, Jr. | A61M 16/0683 128/206.21 |
| 2012/0138061 A1* | 6/2012 | Dravitzki | A61M 16/0633 128/205.25 |
| 2012/0138063 A1* | 6/2012 | Eves | A61M 16/0683 128/206.24 |
| 2012/0152255 A1* | 6/2012 | Barlow | A61M 16/0066 128/205.25 |
| 2012/0222680 A1* | 9/2012 | Eves | A61M 16/065 128/206.24 |
| 2013/0190643 A1* | 7/2013 | Brambilla | A61M 16/0069 600/543 |
| 2014/0338672 A1* | 11/2014 | D'Souza | A61M 16/0858 128/206.24 |
| 2014/0360505 A1* | 12/2014 | Newman | A61M 16/0633 128/206.24 |
| 2015/0034079 A1* | 2/2015 | Allum | A61M 16/0858 128/201.13 |
| 2015/0047643 A9* | 2/2015 | Davidson | A61M 16/0616 128/206.24 |
| 2015/0151066 A1* | 6/2015 | Chodkowski | A61M 16/0638 128/206.24 |
| 2015/0157823 A1* | 6/2015 | Eury, Jr. | A61M 16/06 128/205.25 |
| 2015/0209540 A1* | 7/2015 | Hendriks | A61M 16/0683 128/204.21 |
| 2015/0238716 A1* | 8/2015 | Budhiraja | A61M 16/16 128/203.14 |
| 2015/0297854 A1* | 10/2015 | McCracken | A61M 16/0825 128/201.23 |
| 2015/0314099 A1* | 11/2015 | Carroll | A61M 16/0622 128/206.24 |
| 2015/0335845 A1* | 11/2015 | Baiko | A61M 16/0622 128/206.24 |
| 2015/0335846 A1 | 11/2015 | Romagnoli et al. | |
| 2015/0374944 A1* | 12/2015 | Edwards | A61M 16/0616 128/205.25 |
| 2016/0001029 A1* | 1/2016 | Bayer | A61M 16/0611 128/206.24 |
| 2016/0095996 A1* | 4/2016 | Gusky | A61M 16/08 128/205.25 |
| 2016/0121069 A1* | 5/2016 | Chang | A61M 16/0816 128/202.27 |
| 2016/0129210 A1 | 5/2016 | Matula, Jr. | |

FOREIGN PATENT DOCUMENTS

| | | |
|---|---|---|
| NZ | 548060 | 7/2010 |
| WO | WO 1998/004310 | 2/1998 |
| WO | WO 1998/034665 | 8/1998 |
| WO | WO 2000/078381 | 12/2000 |
| WO | WO 2004/073778 | 9/2004 |
| WO | WO 2005/063328 | 7/2005 |
| WO | WO 2006/074513 | 7/2006 |
| WO | WO 2006/130903 | 12/2006 |
| WO | WO 2009/052560 | 4/2009 |
| WO | WO 2010/135785 | 12/2010 |
| WO | WO 2012/040792 | 4/2012 |

OTHER PUBLICATIONS

Further Examination Report issued in corresponding New Zealand Appln. No. 625846 dated Jul. 11, 2014.
Romagnoli et al., U.S. Appl. No. 14/717,238, filed May 20, 2015, entitled: "Patient Interface", (parent application).

* cited by examiner

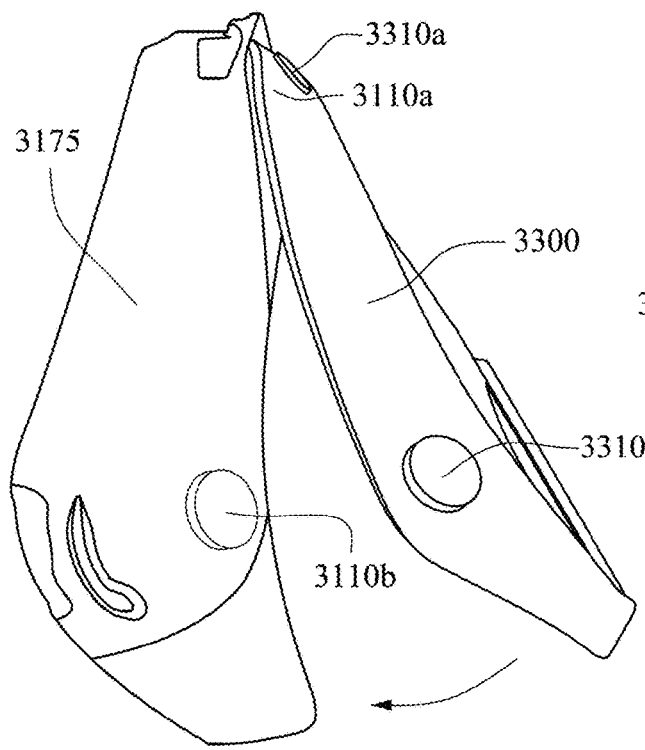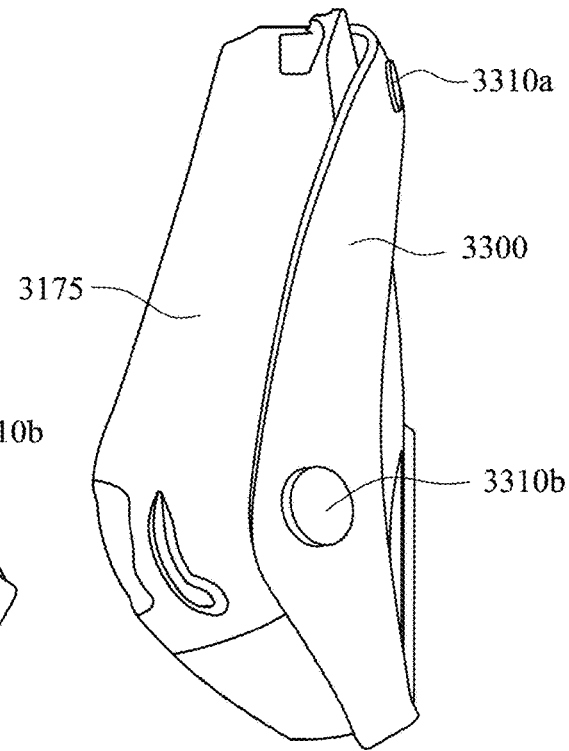
FIG. 19a
FIG. 19b
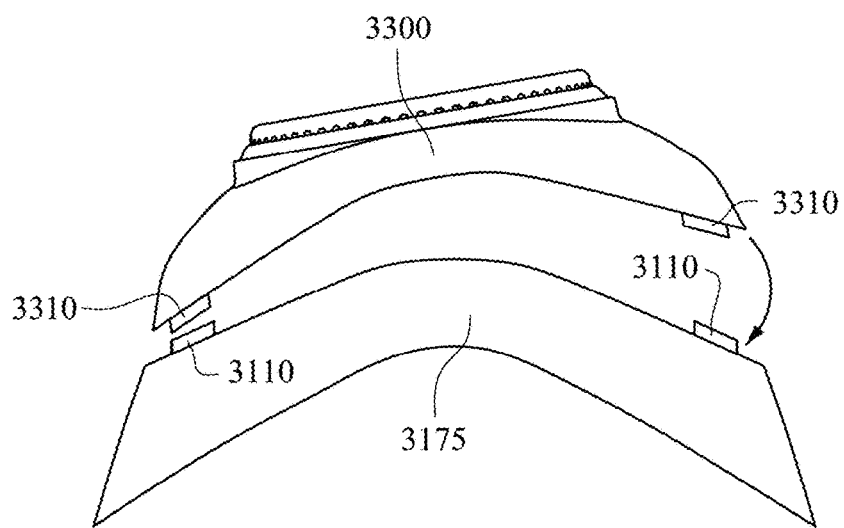
FIG. 19c

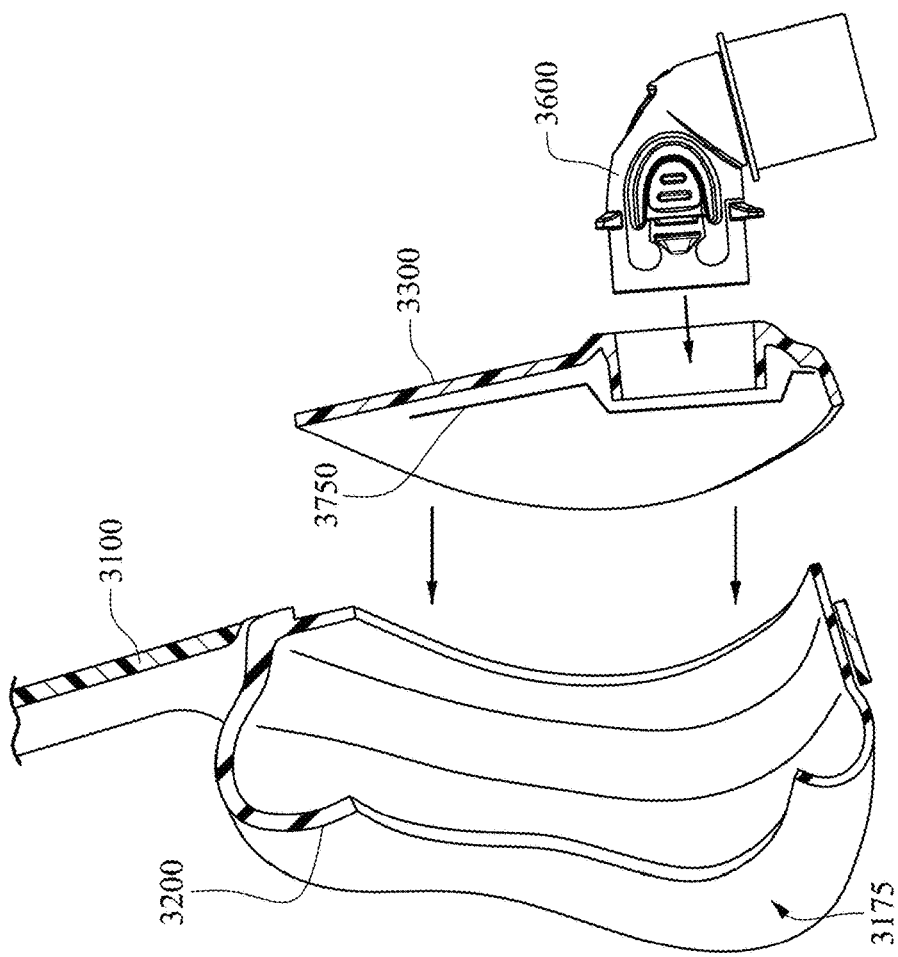
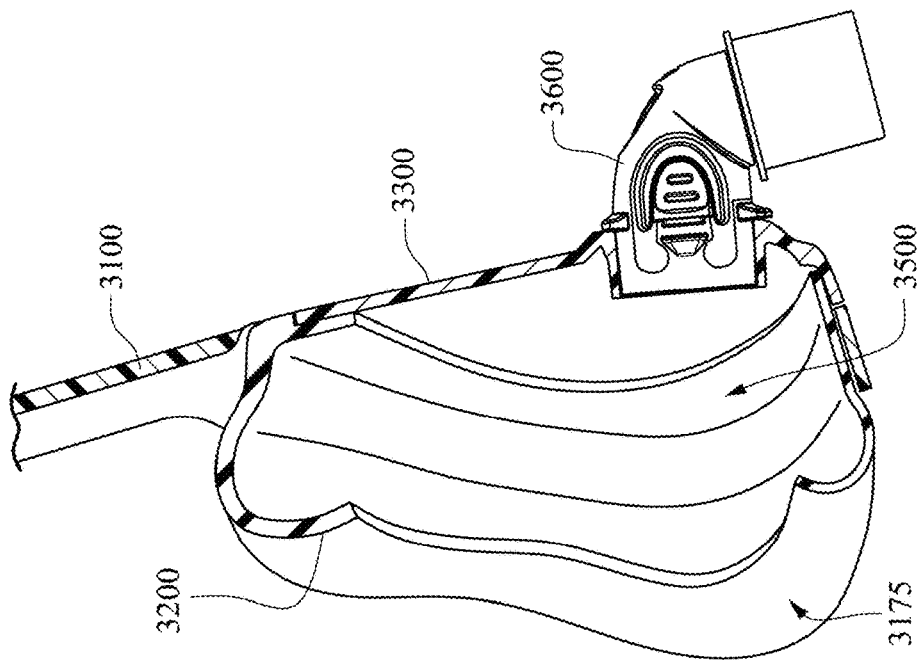
FIG. 20b
FIG. 20a

PATIENT INTERFACE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

CROSS-REFERENCE TO RELATED APPLICATIONS

This application is a continuation of U.S. application Ser. No. 14/717,238, filed May 20, 2015, which claims the benefit of U.S. Provisional Patent Application No. 62/001,944, filed May 22, 2014, each of which is incorporated herein by reference in its entirety.

BACKGROUND OF THE TECHNOLOGY

1.1 (1) Field of the Technology

The present technology relates to one or more of the diagnosis, treatment and amelioration of respiratory disorders, and to procedures to prevent respiratory disorders. In particular, the present technology relates to medical devices, and their use for treating respiratory disorders and for preventing respiratory disorders.

1.2 (2) Description of the Related Art

The respiratory system of the body facilitates gas exchange. The nose and mouth form the entrance to the airways of a patient.

The airways include of a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See West, Respiratory Physiology—the essentials.

A range of respiratory disorders exist.

Obstructive Sleep Apnoea (OSA), a form of Sleep Disordered Breathing (SDB), is characterized by occlusion of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is a disorder of a patient's respiratory controller in which there are rhythmic alternating periods of waxing and waning ventilation, causing repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnoea, repeated chest infections, morning headaches, fatigue, poor sleep quality and loss of appetite.

Otherwise healthy individuals may take advantage of systems and devices to prevent respiratory disorders from arising.

1.2.1 Systems

One known product used for treating sleep disordered breathing is the S9 Sleep Therapy System, manufactured by ResMed.

1.2.2 Therapy

Nasal Continuous Positive Airway Pressure (CPAP) therapy has been used to treat Obstructive Sleep Apnea (OSA). The hypothesis is that continuous positive airway pressure acts as a pneumatic splint and may prevent upper airway occlusion by pushing the soft palate and tongue forward and away from the posterior oropharyngeal wall.

Non-invasive ventilation (NIV) has been used to treat OHS, COPD, MD and Chest Wall disorders.

1.2.3 Patient Interface

The application of a supply of air at positive pressure to the entrance of the airways of a patient is facilitated by the use of a patient interface, such as a nasal mask, full-face mask or nasal pillows. A range of patient interface devices are known, however a number of them suffer from being one or more of obtrusive, aesthetically undesirable, poorly fitting, difficult to use and uncomfortable, especially when worn for long periods of time or when a patient is unfamiliar with a system. Masks designed solely for aviators, as part of personal protection equipment or for the administration of anaesthetics may be tolerable for their original application, but nevertheless be undesirably uncomfortable to be worn for extended periods, for example, while sleeping.

1.2.3.1 Seal-Forming Portion

Patient interfaces typically include a seal-forming portion.

One type of seal-forming portion extends around the periphery of the patient interface, and is intended to seal against the user's face when force is applied to the patient interface with the seal-forming portion in confronting engagement with the user's face. The seal-forming portion may include an air or fluid filled cushion, or a moulded or formed surface of a resilient seal element made of an elastomer such as a rubber. With this type of seal-forming portion, if the fit is not adequate, there will be gaps between the seal-forming portion and the face, and additional force will be required to force the patient interface against the face in order to achieve a seal.

Another type of seal-forming portion incorporates a flap seal of thin material so positioned about the periphery of the mask so as to provide a self-sealing action against the face of the user when positive pressure is applied within the mask. Like the previous style of seal forming portion, if the match between the face and the mask is not good, additional force may be required to effect a seal, or the mask may leak. Furthermore, if the shape of the seal-forming portion does not match that of the patient, it may crease or buckle in use, giving rise to leaks.

Another form of seal-forming portion may use adhesive to effect a seal. Some patients may find it inconvenient to constantly apply and remove an adhesive to their face.

A range of patient interface seal-forming portion technologies are disclosed in the following patent applications, assigned to ResMed Limited: WO 1998/004,310; WO 2006/074,513; WO 2010/135,785.

1.2.3.2 Positioning and Stabilising

A seal-forming portion of a patient interface used for positive air pressure therapy is subject to the corresponding force of the air pressure to disrupt a seal. Thus a variety of techniques have been used to position the seal-forming portion, and to maintain it in sealing relation with the appropriate portion of the face.

One technique is the use of adhesives. See for example US Patent publication US 2010/0000534.

Another technique is the use of one or more straps and/or stabilising harnesses. Many such harnesses suffer from being one or more of ill-fitting, bulky, uncomfortable and awkward to use.

1.2.3.3 Vent Technologies

Some forms of patient interface systems may include a vent to allow the washout of exhaled carbon dioxide. Many such vents are noisy. Others may block in use and provide insufficient washout. Some vents may be disruptive of the sleep of a bed-partner 1100 of the patient 1000, e.g. through noise or focussed airflow.

ResMed Limited has developed a number of improved mask vent technologies. See WO 1998/034,665; WO 2000/078,381; U.S. Pat. No. 6,581,594; US Patent Application; US 2009/0050156; US Patent Application 2009/0044808.

Table of noise of prior masks (ISO 17510-2:2007, 10 $cmH_2O$ pressure at 1 m)

| Mask name | Mask type | A-weighted sound power level dbA (uncertainty) | A-weighted sound pressure dbA (uncertainty) | Year (approx.) |
|---|---|---|---|---|
| Glue-on (*) | nasal | 50.9 | 42.9 | 1981 |
| ResCare standard (*) | nasal | 31.5 | 23.5 | 1993 |
| ResMed Mirage (*) | nasal | 29.5 | 21.5 | 1998 |
| ResMed UltraMirage | nasal | 36 (3) | 28 (3) | 2000 |
| ResMed Mirage Activa | nasal | 32 (3) | 24 (3) | 2002 |
| ResMed Mirage Micro | nasal | 30 (3) | 22 (3) | 2008 |
| ResMed Mirage SoftGel | nasal | 29 (3) | 22 (3) | 2008 |
| ResMed Mirage FX | nasal | 26 (3) | 18 (3) | 2010 |
| ResMed Mirage Swift (*) | nasal pillows | 37 | 29 | 2004 |
| ResMed Mirage Swift II | nasal pillows | 28 (3) | 20 (3) | 2005 |
| ResMed Mirage Swift LT | nasal pillows | 25 (3) | 17 (3) | 2008 |
| ResMed Mirage series I, II (*) | full face | 31.7 | 23.7 | 2000 |
| ResMed UltraMirage | full face | 35 (3) | 27 (3) | 2004 |
| ResMed Mirage Quattro | full face | 26 (3) | 18 (3) | 2006 |
| ResMed Mirage Quattro FX | full face | 27 (3) | 19 (3) | 2008 |

(*) one specimen only, measured using test method specified in ISO3744 in CPAP mode at 10 cm $H_2O$)

Sound pressure values of a variety of objects are listed below

| Object | A-weighted sound pressure dbA (uncertainty) | Notes |
|---|---|---|
| Vacuum cleaner: Nilfisk Walter Broadly Litter Hog: B+ Grade | 68 | ISO3744 at 1 m distance |
| Conversational speech | 60 | 1 m distance |
| Average home | 50 | |
| Quiet library | 40 | |
| Quiet bedroom at night | 30 | |
| Background in TV studio | 20 | |

1.2.3.4 Nasal Pillow Technologies

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT nasal pillows mask, SWIFT II nasal pillows mask, SWIFT LT nasal pillows mask, SWIFT FX nasal pillows mask and LIBERTY full-face mask. The following patent applications, assigned to ResMed Limited, describe nasal pillows masks: International Patent Application WO 2004/073,778 (describing amongst other things aspects of ResMed SWIFT nasal pillows), US Patent Application 2009/0044808 (describing amongst other things aspects of ResMed SWIFT LT nasal pillows); International Patent Applications WO 2005/063, 328 and WO 2006/130,903 (describing amongst other things aspects of ResMed LIBERTY full-face mask); International Patent Application WO 2009/052,560 (describing amongst other things aspects of ResMed SWIFT FX nasal pillows).

2 (B) BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

One aspect of the present technology relates to apparatus used in the diagnosis, treatment or prevention of a respiratory disorder.

Another aspect of the present technology relates to apparatus for treating a respiratory disorder including a patient interface, an air circuit, and a source of air at positive pressure.

Another aspect of the present technology relates to methods used in the diagnosis, treatment or prevention of a respiratory disorder.

Another aspect of the present technology relates to a patient interface for sealed delivery of a flow of breathable gas at a continuously positive pressure with respect to ambient air pressure to an entrance to the patient's airways including at least entrance of a patient's nares, wherein the patient interface is configured to maintain a therapy pressure in a range of about $4cmH_2O$ to about 30 $cmH_2O$ above ambient air pressure in use, throughout the patient's respiratory cycle, while the patient is sleeping, to ameliorate sleep disordered breathing. In an example, the patient interface includes a cushion assembly including a seal-forming structure adapted to form a seal against the patient's airways and a plenum chamber pressurised at a pressure above ambient pressure in use, a positioning and stabilising structure to maintain the cushion assembly in sealing contact with an area surrounding an entrance to the patient's airways while maintaining a therapeutic pressure at the entrance to the patient's airways, a gas washout vent configured to allow a flow of patient exhaled $CO_2$ to an exterior of the patient interface to minimise rebreathing of exhaled $CO_2$ by the patient, and a frame assembly to releasably engage the cushion assembly and provide a connection to the positioning and stabilising structure.

Another aspect of the present technology relates to a patient interface having improved comfort by reducing apparent bulk/obtrusiveness of the patient interface, reducing the claustrophobic (enclosed) feeling of the patient interface and/or providing a patient interface that allows the patient to feel more in control of their therapy.

Another aspect of the present technology relates to a patient interface including a repeatedly engageable/disengageable anterior wall member or fascia that allows the patient's nose and/or mouth to be substantially exposed when disengaged to improve breathing comfort of the patient (e.g., minimal breathing obstruction). Such arrangement provides improved breathing comfort when therapy is not required and does not require the patient to adjust the headgear or the cushion seal since the patient interface remains on the patient's head when the fascia is disengaged or removed. Such arrangement provides less bulk on the patient's face (facial footprint area and weight) when therapy is not required, when the patient has removed the fascia. Also, such arrangement may allow automatic start/stop of pressurised air to the patient interface upon detection of fascia engagement/disengagement, therefore minimizing waste of pressurised air when therapy is not required. Removal of the fascia may also improve patient communication with the bed partner (e.g., no muffled voice and ability for bed partner to clearly view the patient's mouth), allow the patient to drink/eat/medicate without having to completely remove the patient interface, allow the clinician to view and assess the cushion seal on the patient's face, optimize gas washout, facilitate patient/clinician acclimatization to CPAP therapy (e.g., training-type patient interface), and/or provide a means for patient to disconnect patient interface from the flow generator (e.g., to go to the bathroom throughout the night).

In an example, the cushion assembly and the anterior wall member (fascia) are structured to maintain engagement during use and prevent any unintentional or partial disassembly during use, e.g., caused by tube drag forces. In an example, the anterior wall members sealingly engages the cushion assembly, e.g., to prevent leak. In an example, the anterior wall member and cushion assembly provide an easy/intuitive arrangement for assembly/disassembly (e.g., assembly/disassembly without instruction), which requires minimal dexterity (e.g., one-handed operation). In an example, assembly/disassembly of the anterior wall member to the cushion assembly may require less than about 6N force. In an example, audible, tactile and/or visual feedback may be provided upon correct assembly of the anterior wall member to the cushion assembly.

Another aspect of the present technology relates to a patient interface arrangement for treatment of sleep disordered breathing that may allow automatic start/stop of pressurised air to the patient interface upon detection of engagement/disengagement (e.g., via magnetic sensors) of a fascia, elbow and/or gas delivery tube, therefore minimizing waste of pressurised air when therapy is not required.

Another aspect of the present technology relates to a patient interface for delivery of a supply of pressurised air or breathable gas to an entrance of a patient's airways including a frame member, a cushion assembly provided to the frame member, and an anterior wall member repeatedly engageable with and disengageable from the cushion assembly. The frame member includes connectors operatively attachable to a positioning and stabilizing structure. The cushion assembly includes a seal-forming structure and a void defined by an anterior surface of the cushion assembly. The anterior wall member has a predetermined surface area to seal the void of the cushion assembly and form a gas chamber when the anterior wall member and the cushion assembly are engaged. The void of the cushion assembly is sized such that the patient's nose and/or mouth is substantially exposed when the anterior wall member is disengaged from the cushion assembly thereby improving breathing comfort of the patient.

Another aspect of the present technology relates to a method of donning a patient interface for delivery of a supply of pressurised air or breathable gas to an entrance of a patient's airways, the method including providing a frame member including connectors to a cushion assembly including a seal-forming structure and a void defined by an anterior surface of the cushion assembly, positioning the cushion assembly against the patient's face using a positioning and stabilizing structure operatively attached to the frame member, and engaging an anterior wall member having a predetermined surface area with the cushion assembly to seal the void of the cushion assembly and form a gas chamber when the anterior wall member and the cushion assembly are sealingly engaged, the anterior wall member comprising a connection port for connection to a gas delivery tube, wherein the void of the cushion assembly is sized such that the patient's nose and/or mouth is substantially exposed to ambient air when the anterior wall member is disengaged from the cushion assembly.

Another aspect of the present technology relates to a patient interface for sealed delivery of a flow of breathable gas at a continuously positive pressure with respect to ambient air pressure to an entrance to the patient's airways including at least entrance of a patient's nares, wherein the patient interface is configured to maintain a therapy pressure in a range of about 4cmH$_2$O to about 30 cmH$_2$O above ambient air pressure in use, throughout the patient's respiratory cycle, while the patient is sleeping, to ameliorate sleep disordered breathing. The patient interface includes a cushion assembly including a seal-forming structure adapted to form a seal against the patient's airways, a positioning and stabilising structure to maintain the cushion assembly in sealing contact with an area surrounding an entrance to the patient's airways while maintaining a therapeutic pressure at the entrance to the patient's airways, a frame member to engage the cushion assembly and provide a connection to the positioning and stabilising structure, the cushion assembly including a void defined by an anterior surface of the cushion assembly, and an anterior wall member repeatedly engageable with and disengageable from the cushion assembly. The anterior wall member has a predetermined surface area to seal the void of the cushion assembly and form a gas chamber when the anterior wall member and the cushion assembly are engaged. The anterior wall member and the cushion assembly are magnetically engageable.

Another aspect of the present technology relates to a patient interface for sealed delivery of a flow of breathable gas at a continuously positive pressure with respect to ambient air pressure to an entrance to the patient's airways including at least entrance of a patient's nares, wherein the patient interface is configured to maintain a therapy pressure in a range of about 4cmH$_2$O to about 30 cmH$_2$O above ambient air pressure in use, throughout the patient's respiratory cycle, while the patient is sleeping, to ameliorate sleep disordered breathing. The patient interface includes a cushion assembly including a seal-forming structure adapted to form a seal against the patient's airways, a positioning and stabilising structure to maintain the cushion assembly in sealing contact with an area surrounding an entrance to the patient's airways while maintaining a therapeutic pressure at the entrance to the patient's airways, a frame member to engage the cushion assembly and provide a connection to the positioning and stabilising structure, the frame member including a void defined by an anterior surface of the frame member, and an anterior wall member repeatedly engageable with and disengageable from the frame member. The anterior wall member has a predetermined surface area to seal the void of the frame member and form a gas chamber when the anterior wall member and the frame member are engaged. The anterior wall member and the frame member are magnetically engageable.

Another aspect of the present technology relates to a patient interface for sealed delivery of a flow of breathable gas at a continuously positive pressure with respect to ambient air pressure to an entrance to the patient's airways including at least entrance of a patient's nares, wherein the patient interface is configured to maintain a therapy pressure in a range of about 4cmH$_2$O to about 30 cmH$_2$O above ambient air pressure in use, throughout the patient's respiratory cycle, while the patient is sleeping, to ameliorate sleep disordered breathing. The patient interface includes a frame member including connectors operatively attachable to a positioning and stabilizing structure, a cushion assembly provided to the frame member, an anterior wall member repeatedly engageable with and disengageable from the cushion assembly, and a detachable heat and moisture exchanger (HME/HMX) cartridge. The cushion assembly includes a seal-forming structure and a void defined by an anterior surface of the cushion assembly. The anterior wall member has a predetermined surface area to seal the void of the cushion assembly and form a gas chamber when the anterior wall member and the cushion assembly are engaged. The HME/HMX cartridge is positioned within the gas chamber. The HME/HMX cartridge has a length greater than 22 mm. The anterior wall member has a length at least the same as the length of the HME/HMX cartridge to allow the HME/HMX cartridge to be detached via the void defined by the anterior surface of the cushion assembly.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

(C) BRIEF DESCRIPTION OF THE SEVERAL VIEWS OF THE DRAWINGS

The present technology is illustrated by way of example, and not by way of limitation, in the figures of the accompanying drawings, in which like reference numerals refer to similar elements including:

2.1 Treatment Systems

FIG. 1a shows a system in accordance with the present technology. A patient 1000 wearing a patient interface 3000, receives a supply of air at positive pressure from a PAP device 4000. Air from the PAP device is humidified in a humidifier 5000, and passes along a gas delivery tube 4170 to the patient 1000.

2.2 Therapy

2.2.1 Respiratory System

Figure 2A:
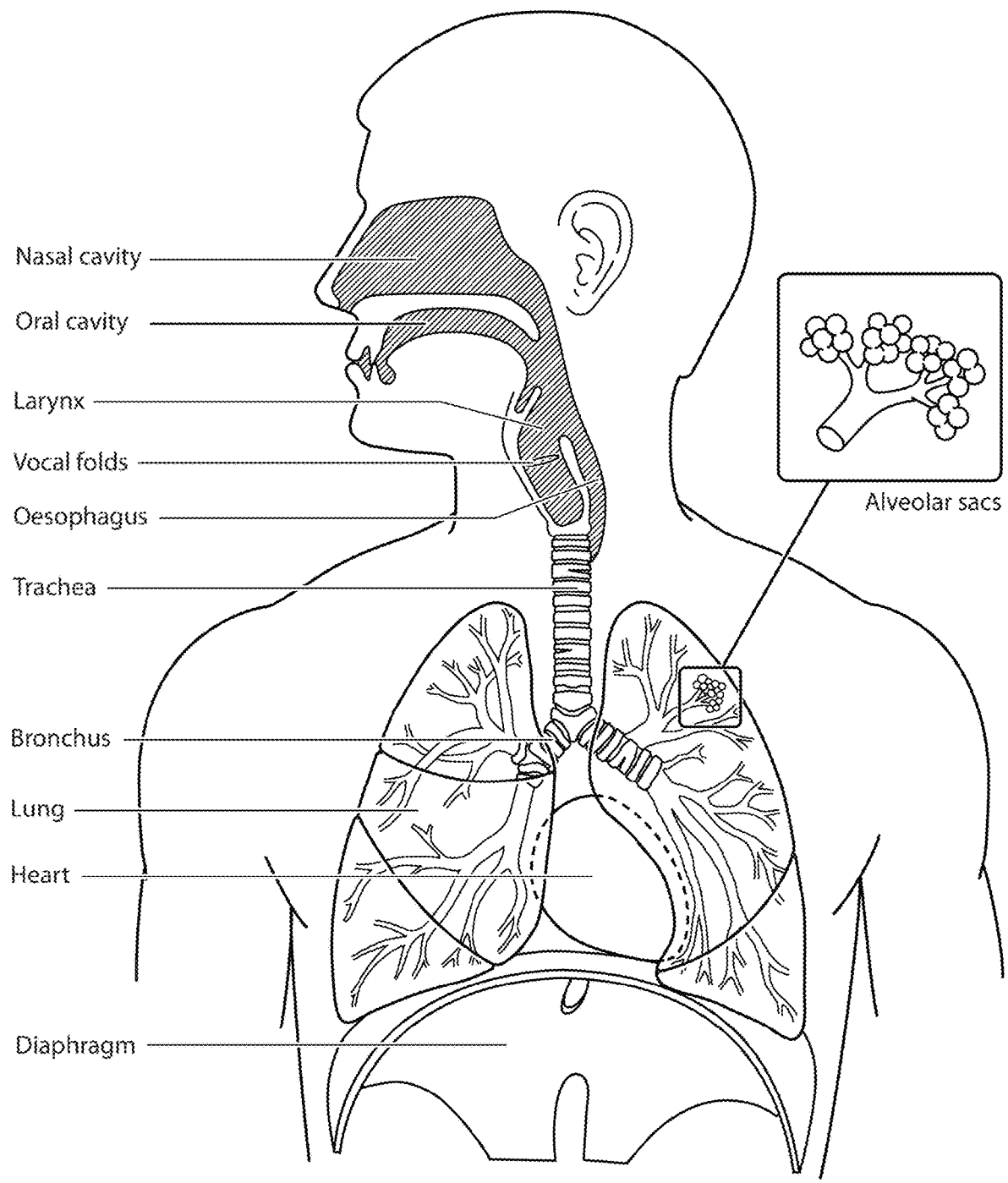

FIG. 2a shows an overview of a human respiratory system including the nasal and oral cavities, the larynx, vocal folds, oesophagus, trachea, bronchus, lung, alveolar sacs, heart and diaphragm.

Figure 2B:
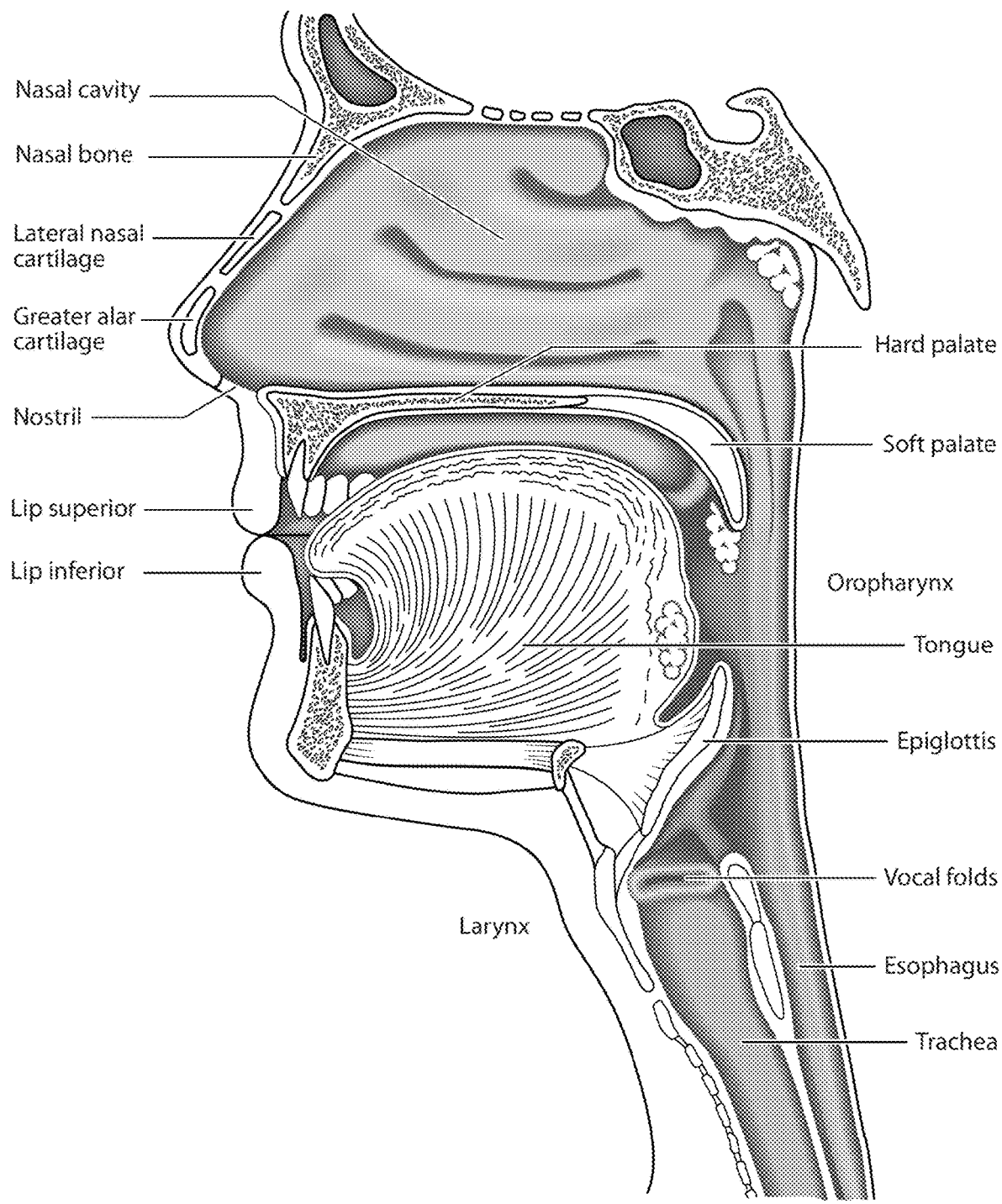

FIG. 2b shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.

2.2.2 Facial Anatomy

Figure 2C:
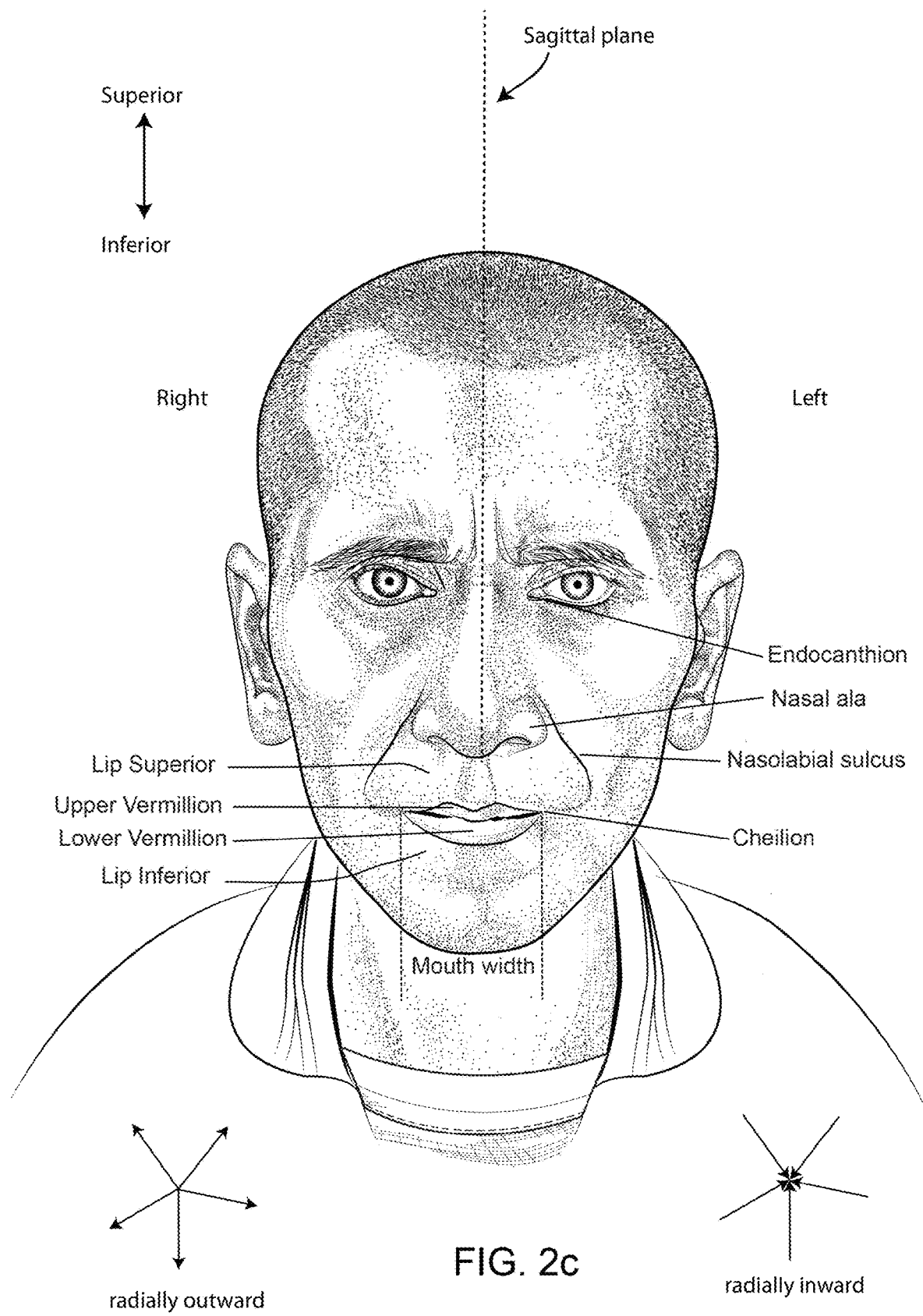

FIG. 2c is a front view of a face with several features of surface anatomy identified including the lip superior, upper vermillion, lower vermillion, lip inferior, mouth width, endocanthion, a nasal ala, nasolabial sulcus and cheilion.

Figure 2D:
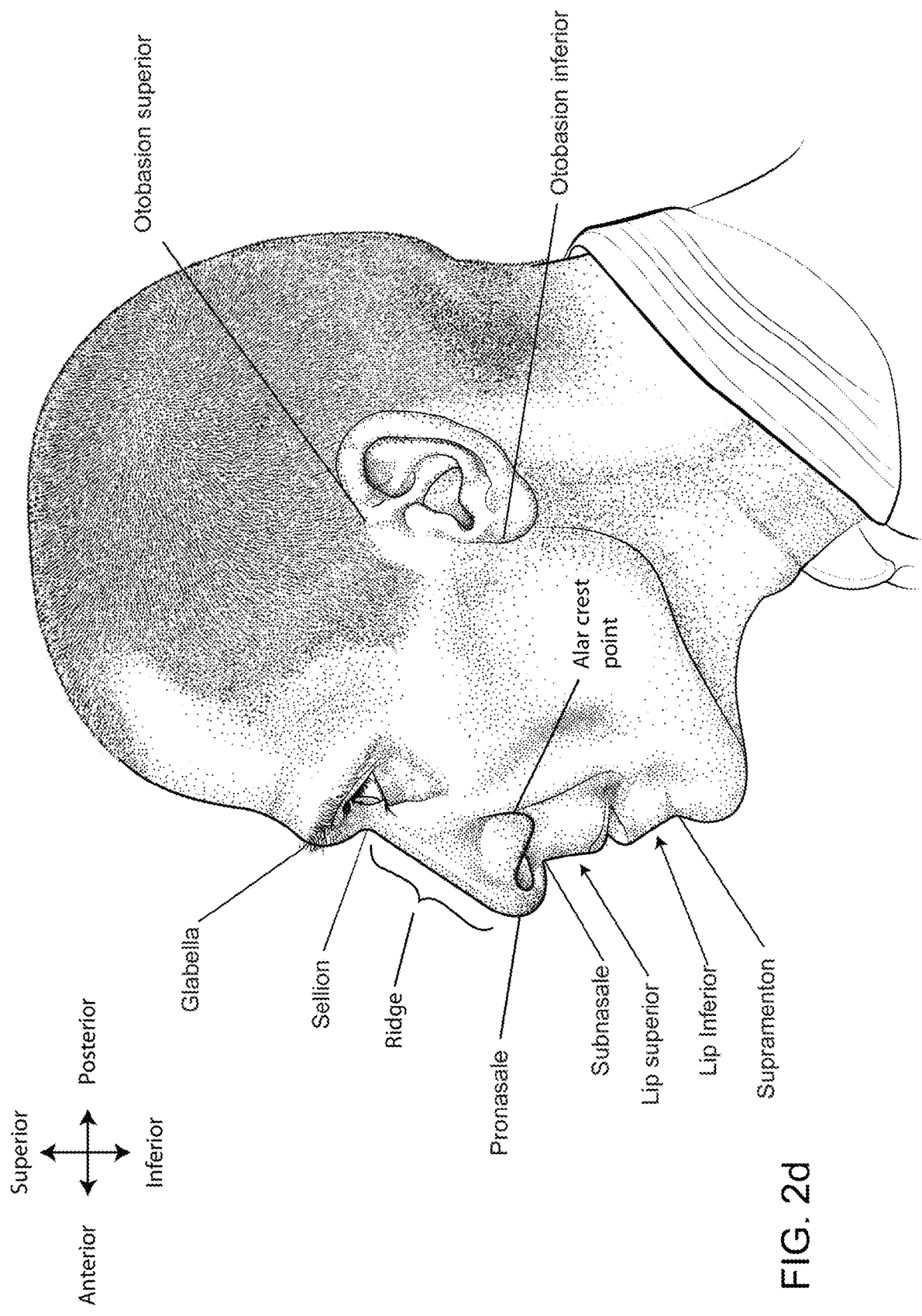

FIG. 2d is a side view of a head with several features of surface anatomy identified including glabella, sellion, pronasale, subnasale, lip superior, lip inferior, supramenton, nasal ridge, otobasion superior and otobasion inferior. Also indicated are the directions superior & inferior, and anterior & posterior.

Figure 2E:
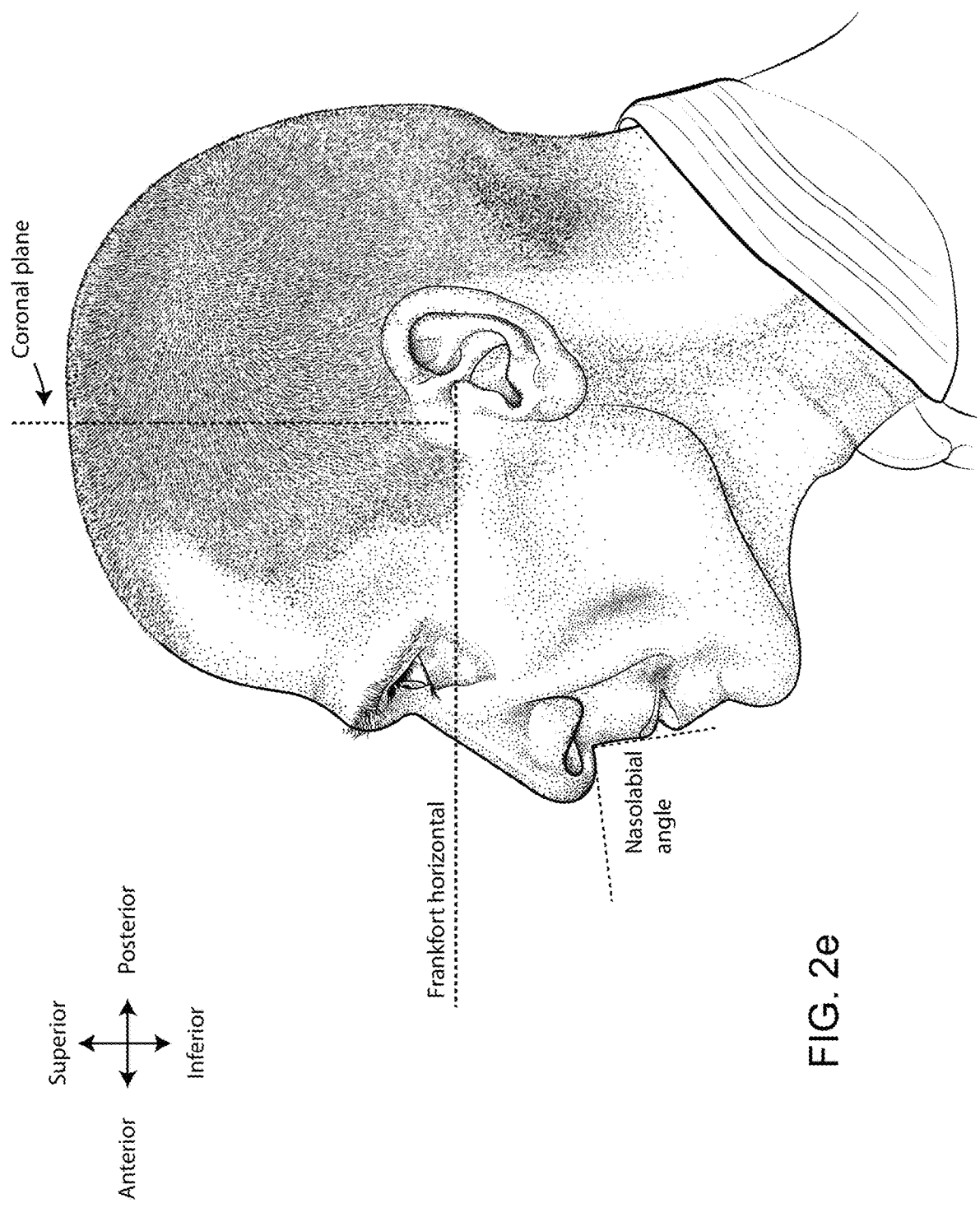

FIG. 2e is a further side view of a head. The approximate locations of the Frankfort horizontal and nasolabial angle are indicated.

Figure 2F:
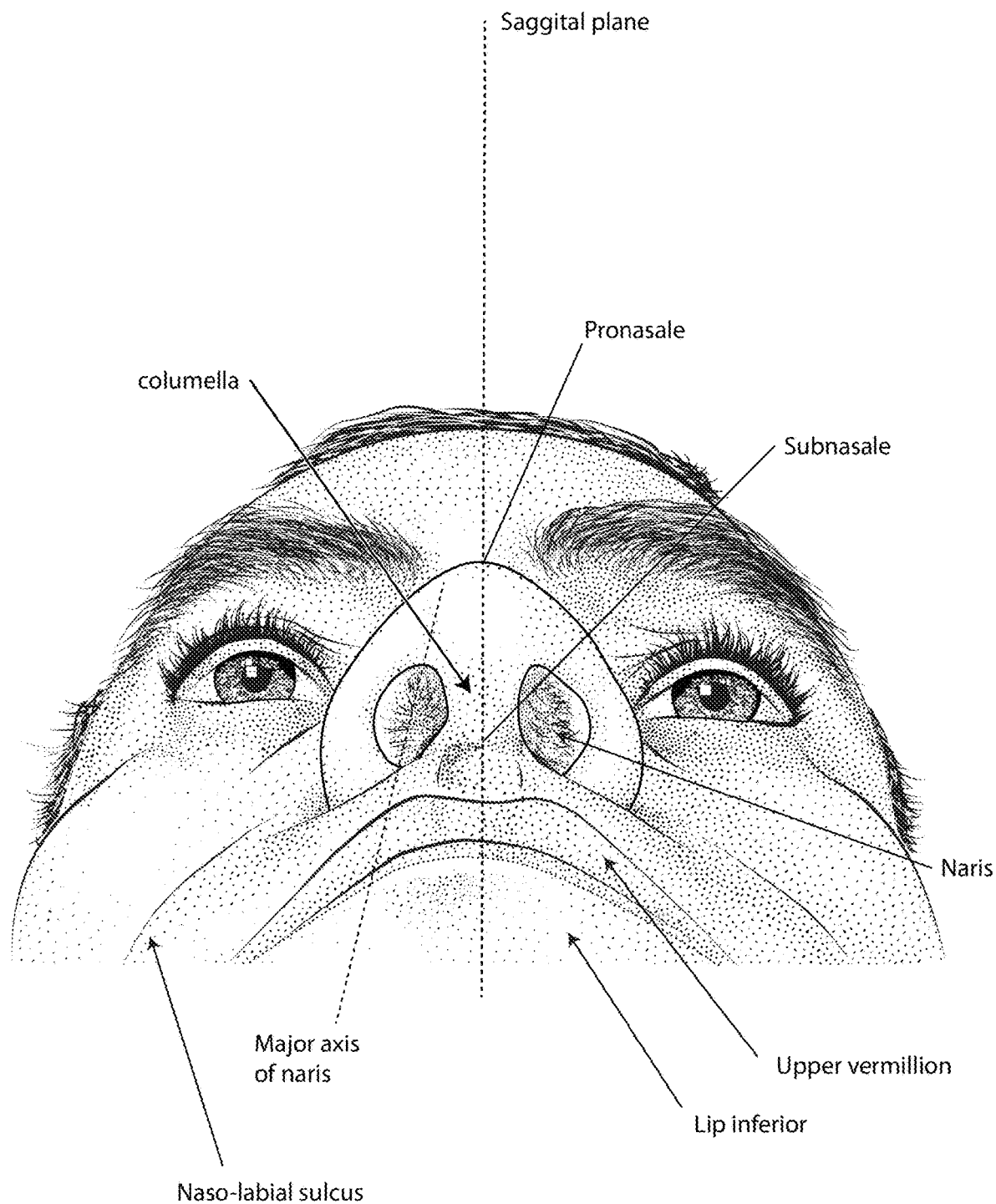

FIG. 2f shows a base view of a nose.

Figure 2I:
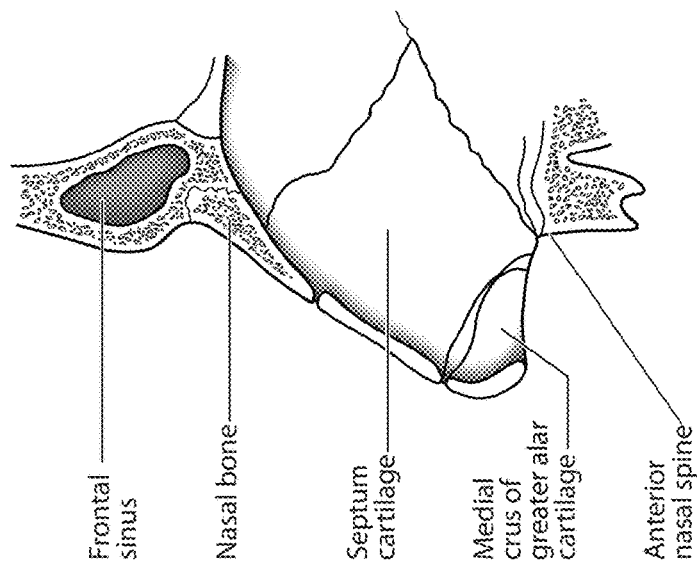
Figure 2H:
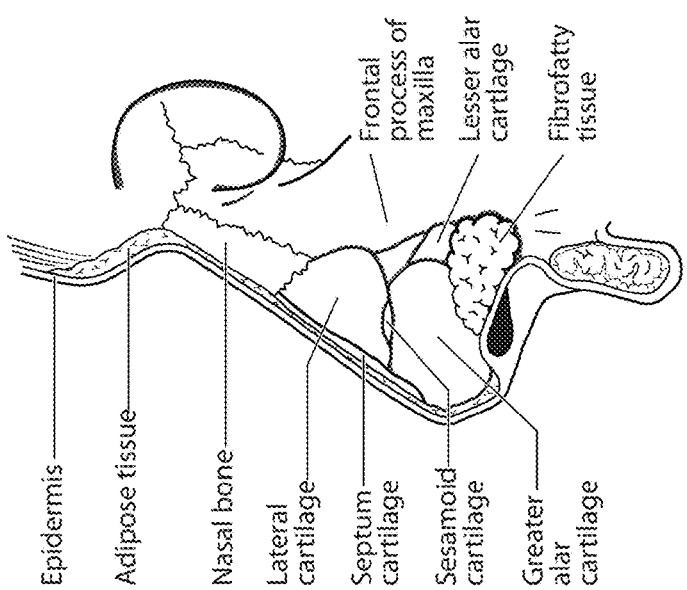
Figure 2G:
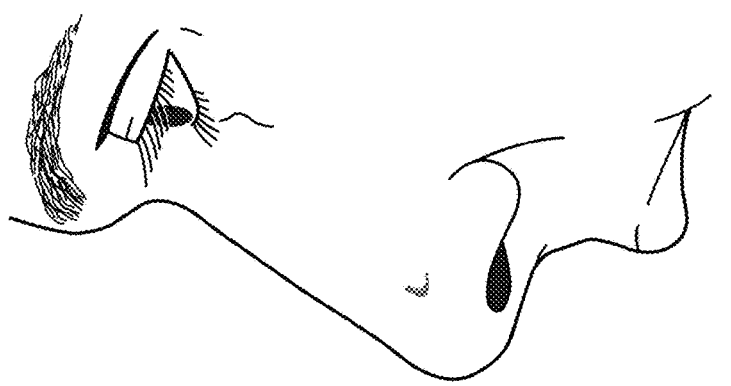

FIG. 2g shows a side view of the superficial features of a nose.

FIG. 2h shows subcutaneal structures of the nose, including lateral cartilage, septum cartilage, greater alar cartilage, lesser alar cartilage and fibrofatty tissue.

FIG. 2i shows a medial dissection of a nose, approximately several millimeters from a sagittal plane, amongst other things showing the septum cartilage and medial crus of greater alar cartilage.

Figure 2J:
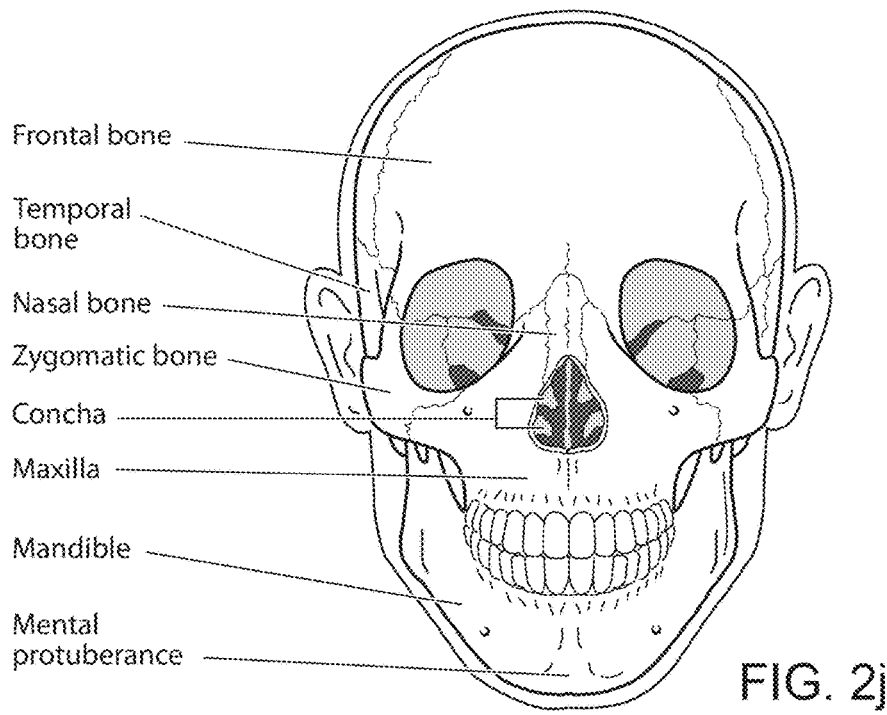

FIG. 2j shows a front view of the bones of a skull including the frontal, temporal, nasal and zygomatic bones. Nasal concha are indicated, as are the maxilla, mandible and mental protuberance.

Figure 2K:
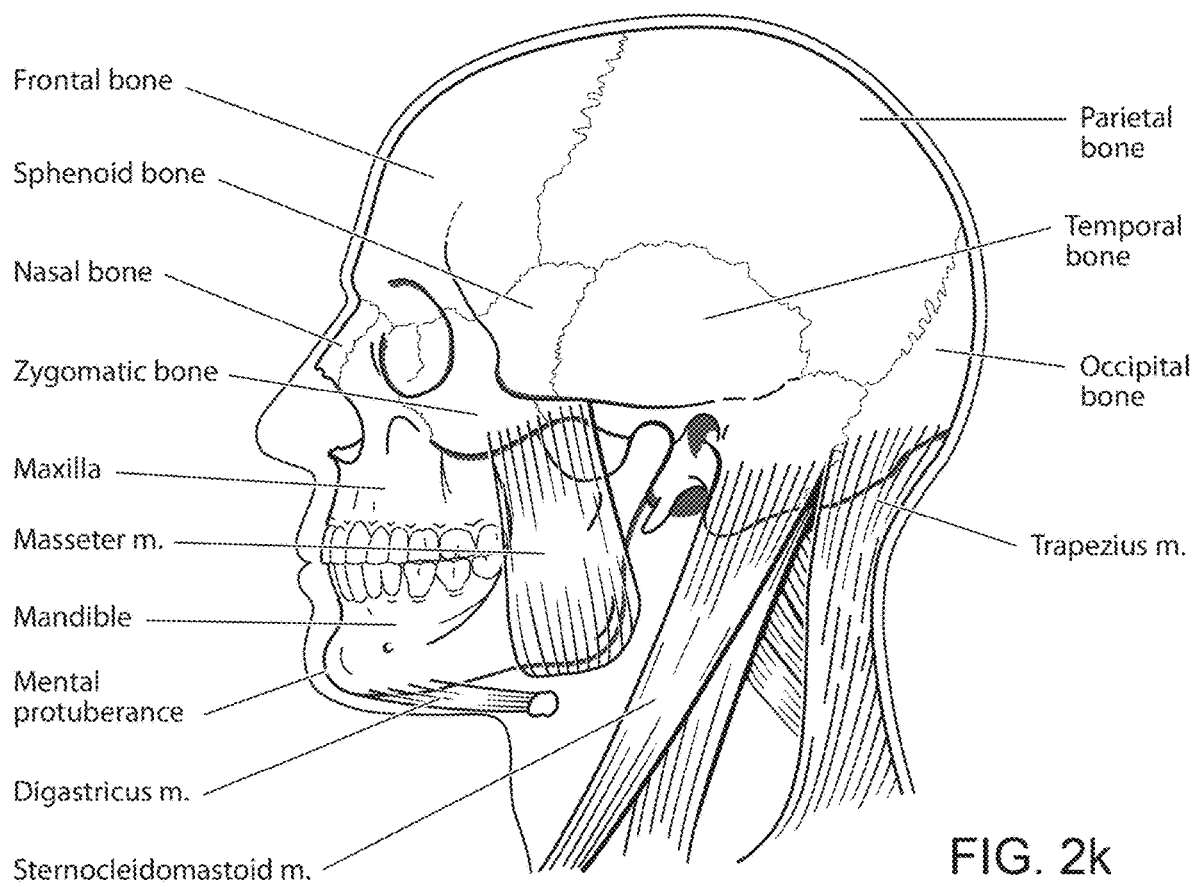

FIG. 2k shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter sternocleidomastoid and trapezius.

FIG. 2l shows an anterolateral view of the nose and skull, including bone and cartilaginous structures.

2.3 Pap Device and Humidifier

Figure 3A:
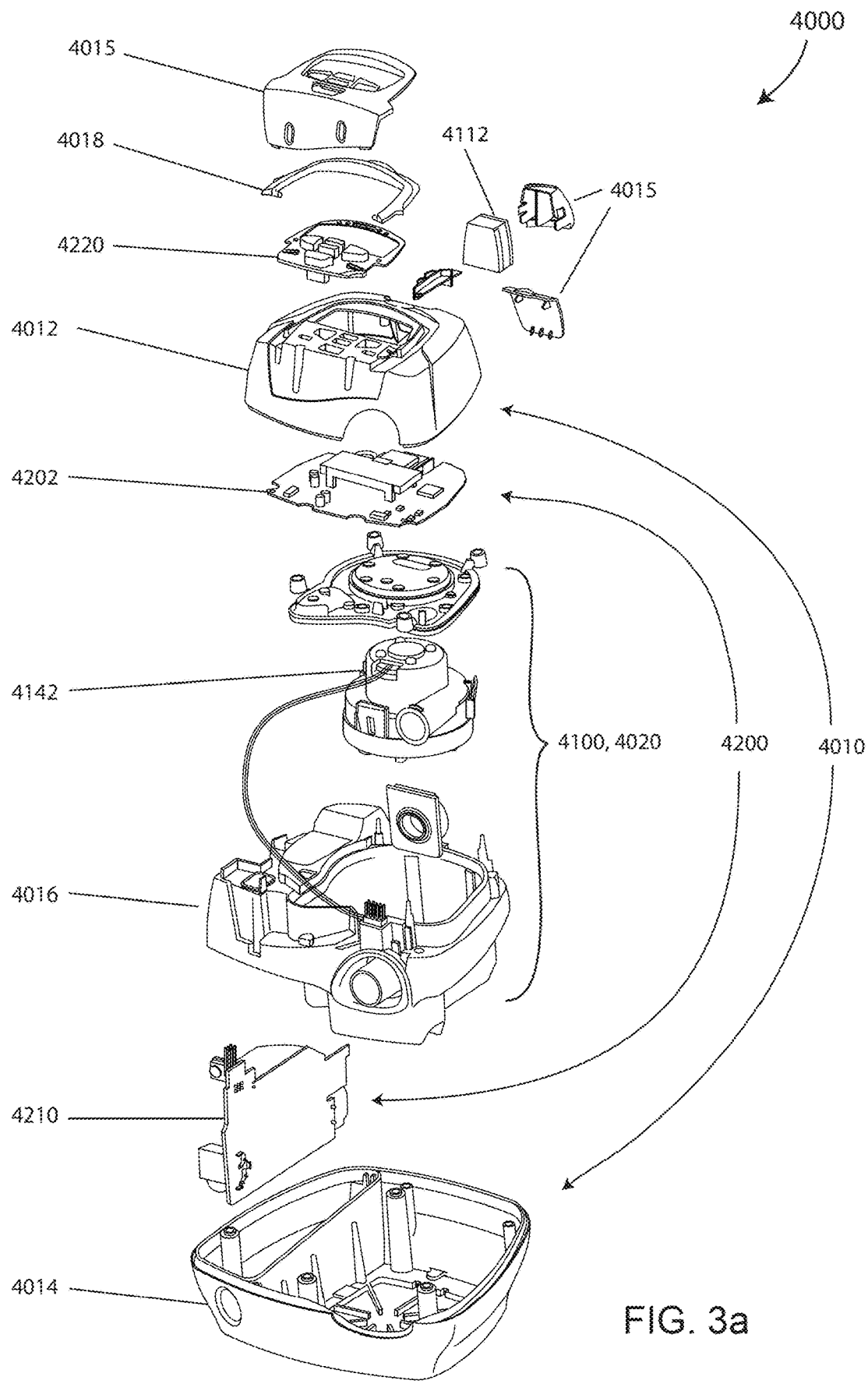

FIG. 3a shows an exploded view of a PAP device according to an example of the present technology.

Figure 3B:
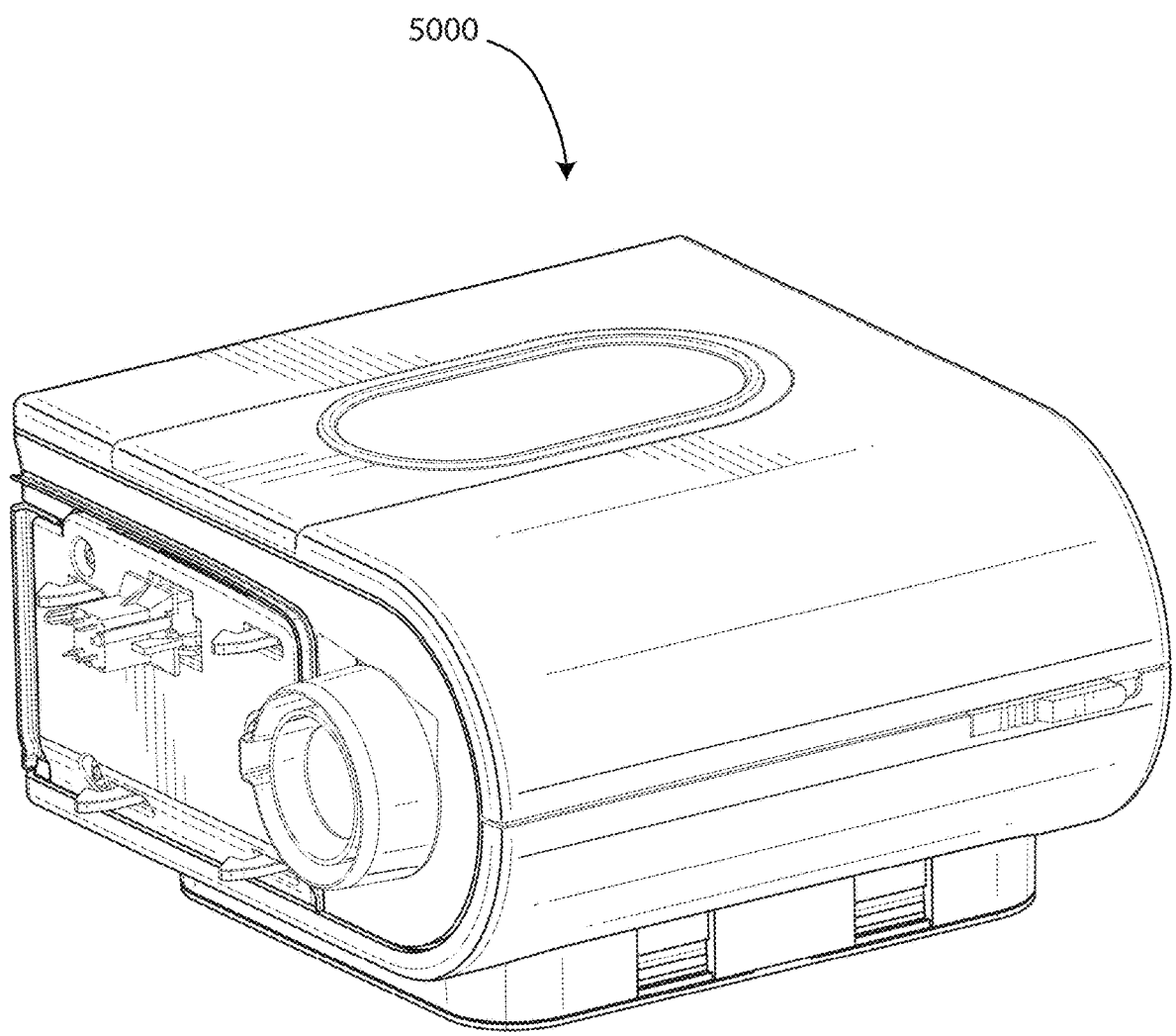

FIG. 3b shows a perspective view of a humidifier in accordance with one form of the present technology.

Figure 3C:
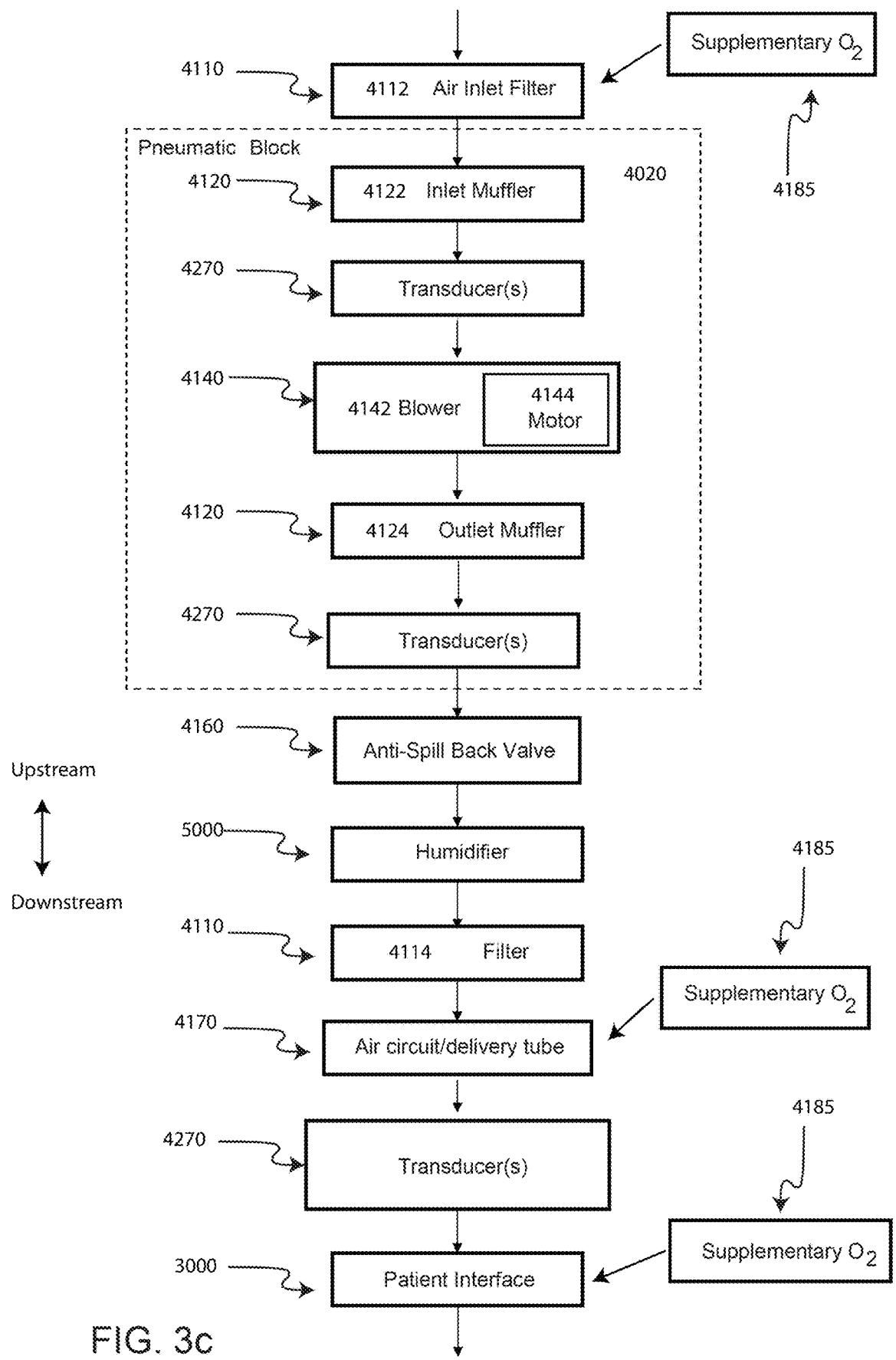

FIG. 3c shows a schematic diagram of the pneumatic circuit of a PAP device in accordance with one form of the present technology. The directions of upstream and downstream are indicated.

2.4 Patient Interface

Figure 4:
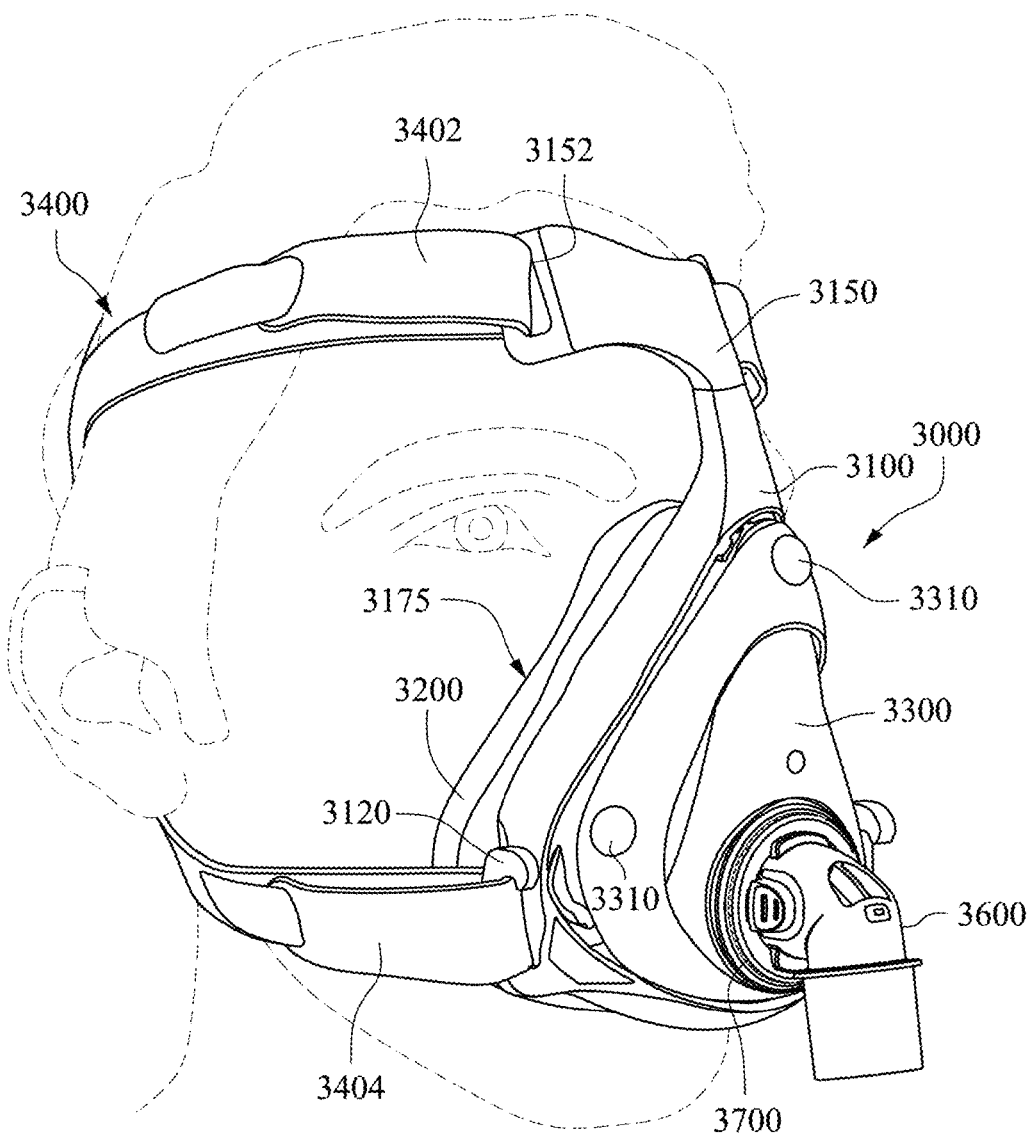

FIG. 4 is a perspective view of a patient interface shown on a patient's head according to an example of the present technology, the patient interface being shown with a removable anterior wall member engaged with the cushion assembly.

Figure 5:
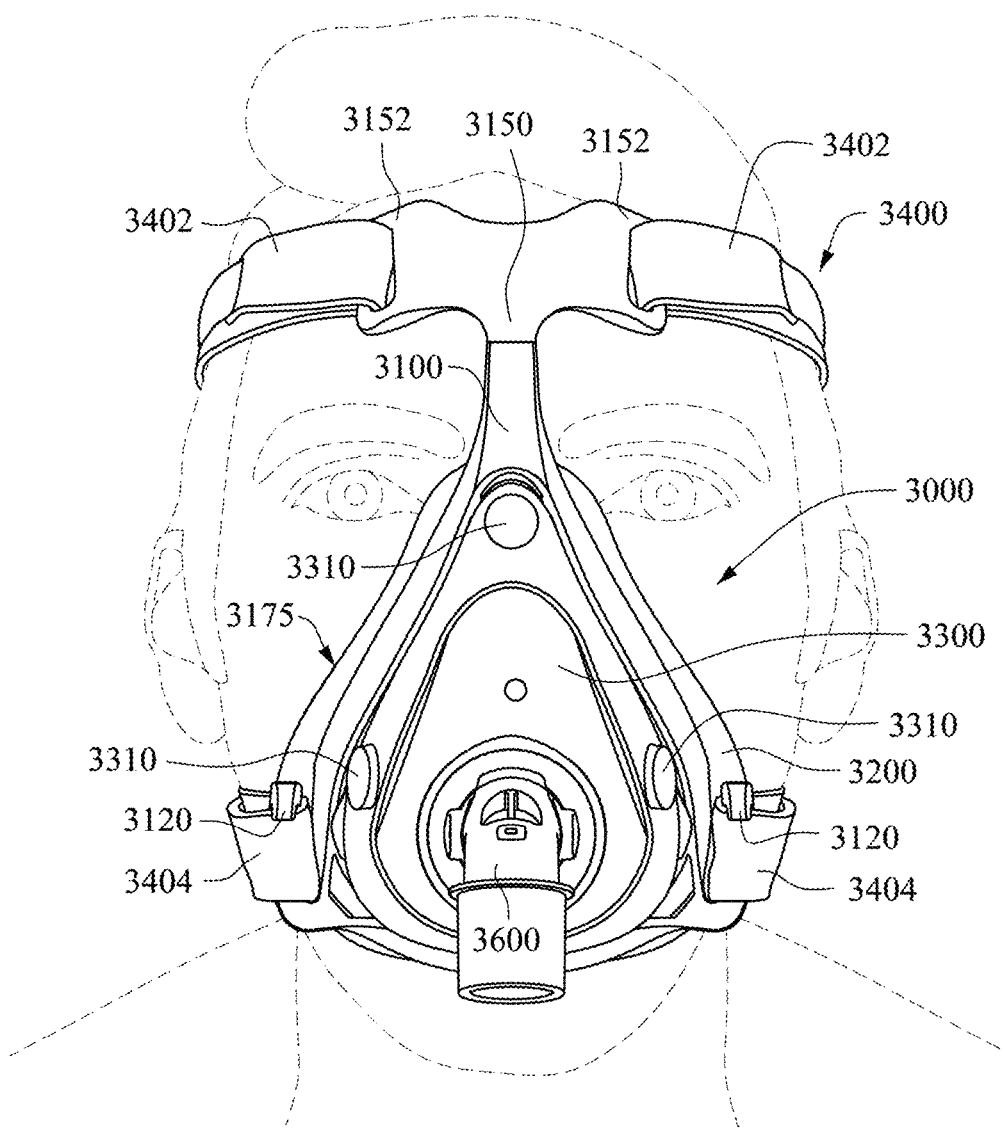

FIG. 5 is a front view of the patient interface shown in FIG. 4.

Figure 6:
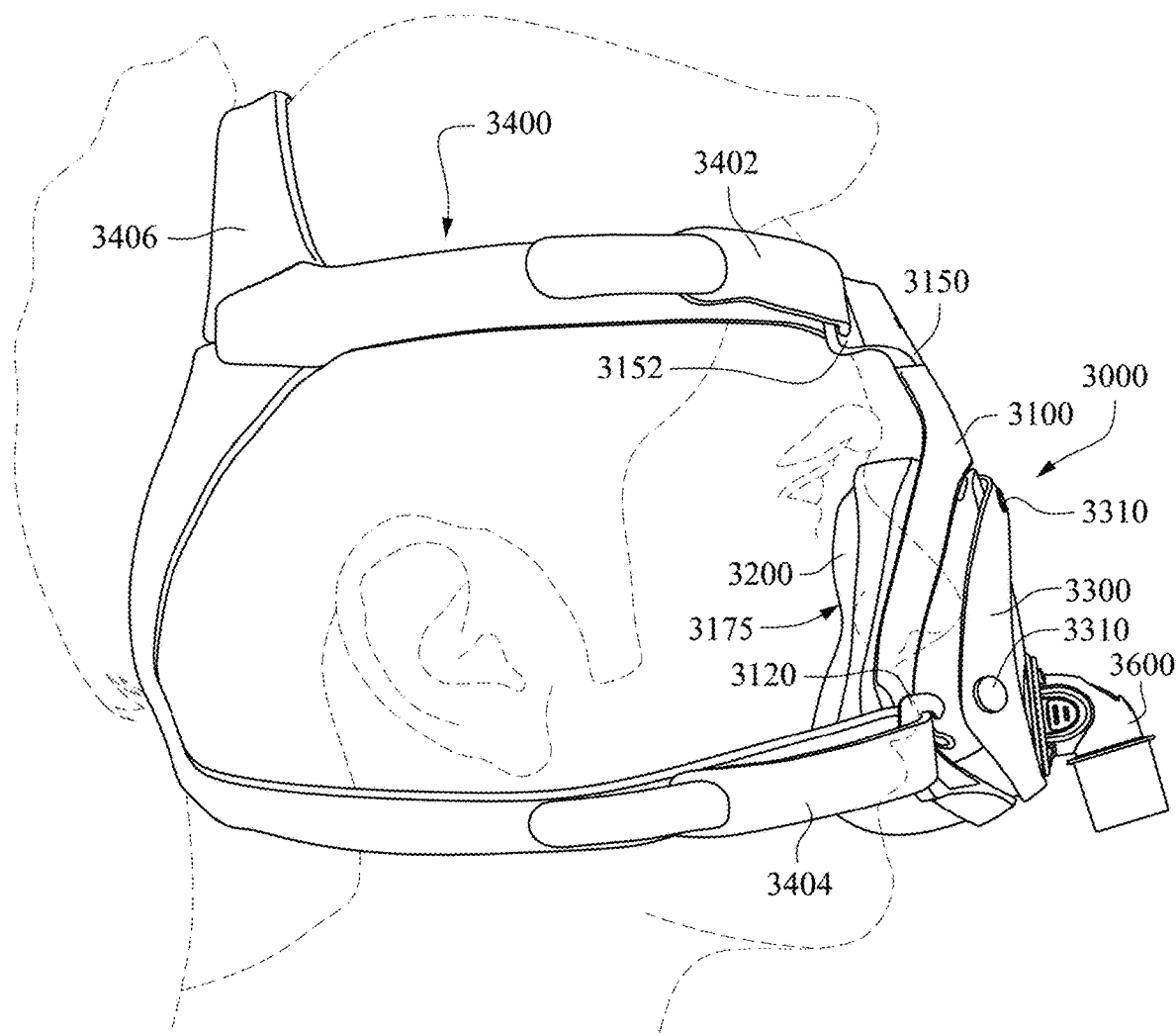

FIG. 6 is a side view of the patient interface shown in FIG. 4.

Figure 7:
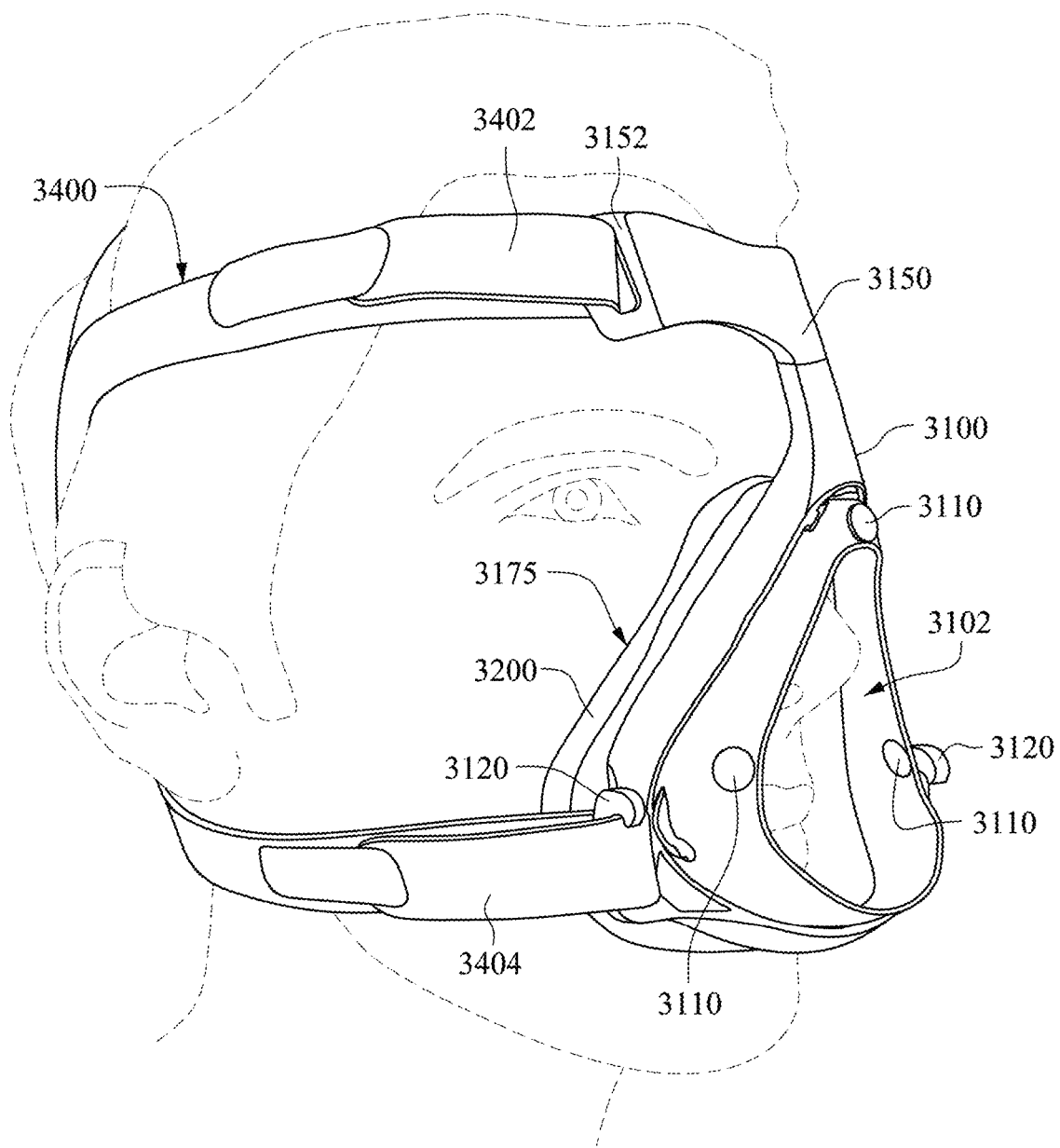

FIG. 7 is a perspective view of a patient interface shown on a patient's head according to an example of the present technology, the patient interface being shown with the anterior wall member disengaged and removed from the cushion assembly.

Figure 8:
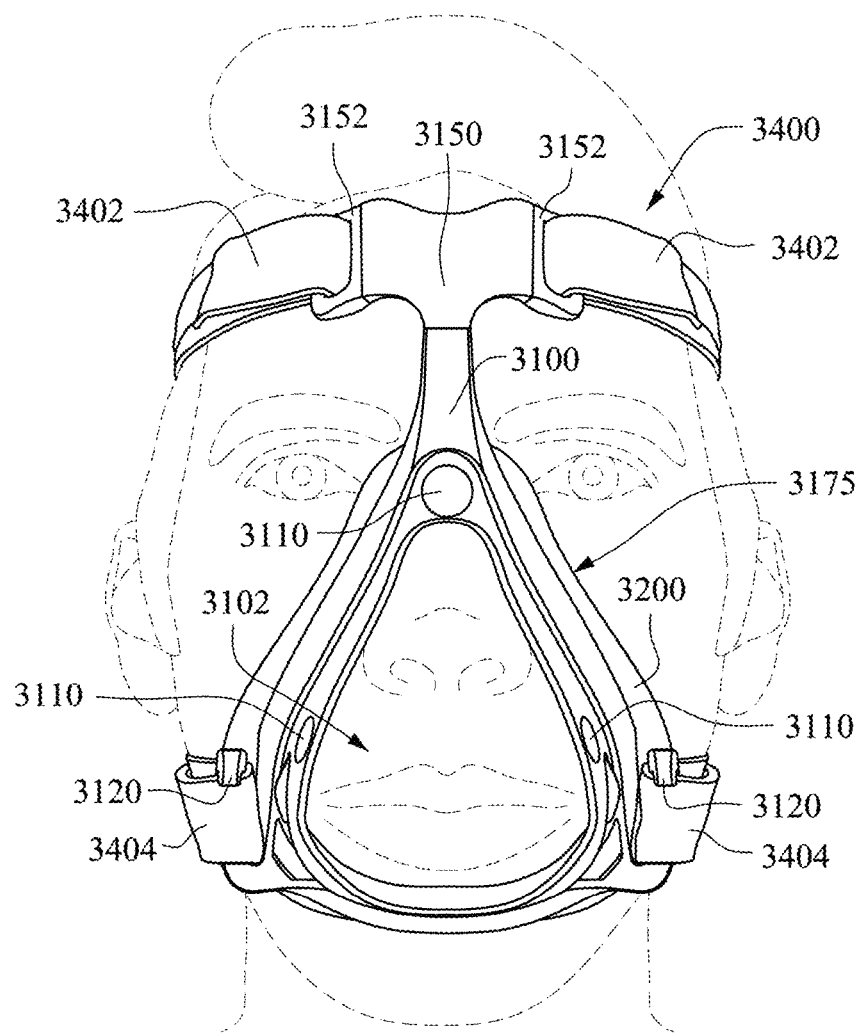

FIG. 8 is a front view of the patient interface shown in FIG. 7.

Figure 9:
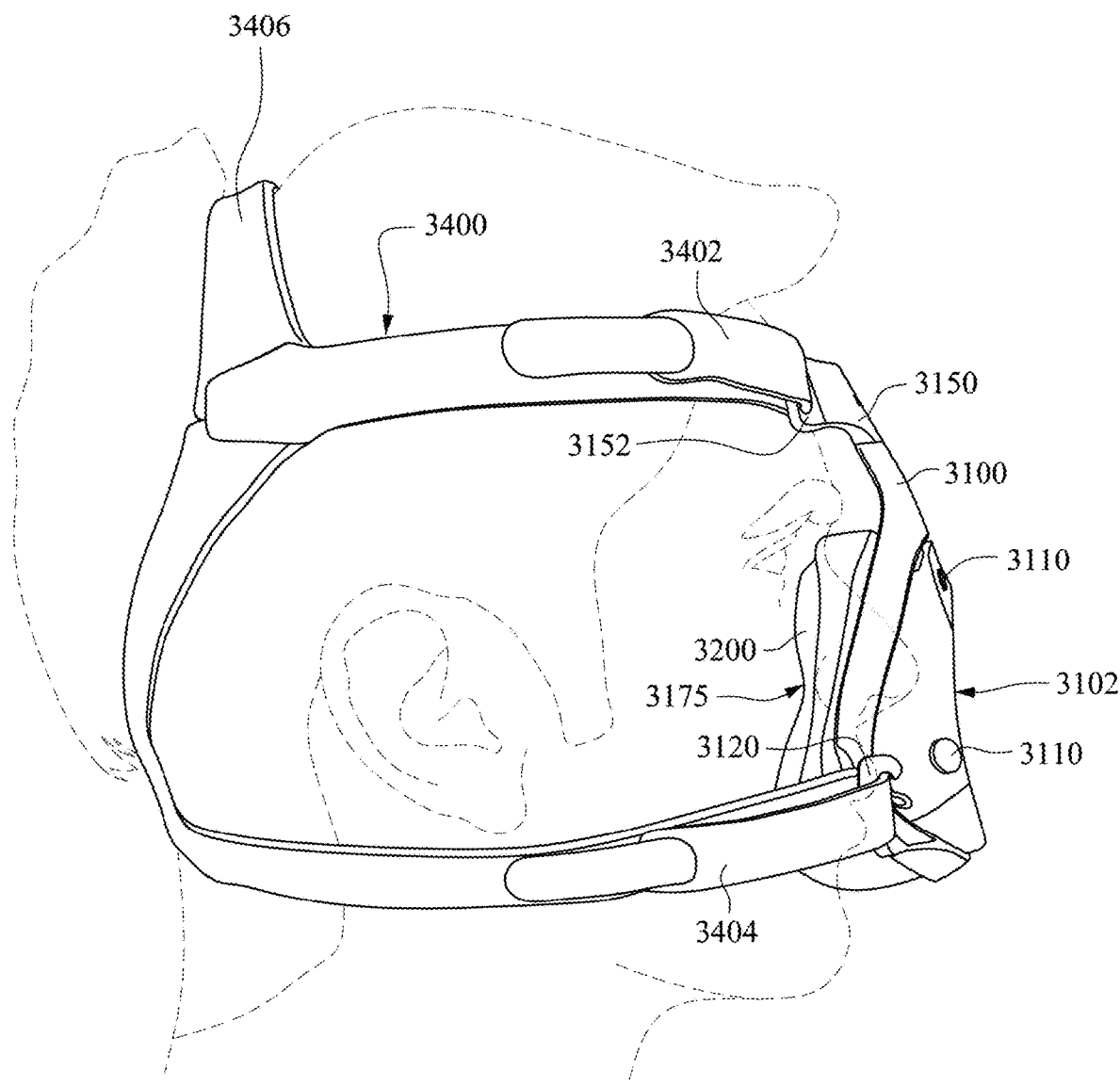

FIG. 9 is a side view of the patient interface shown in FIG. 7.

Figure 10:
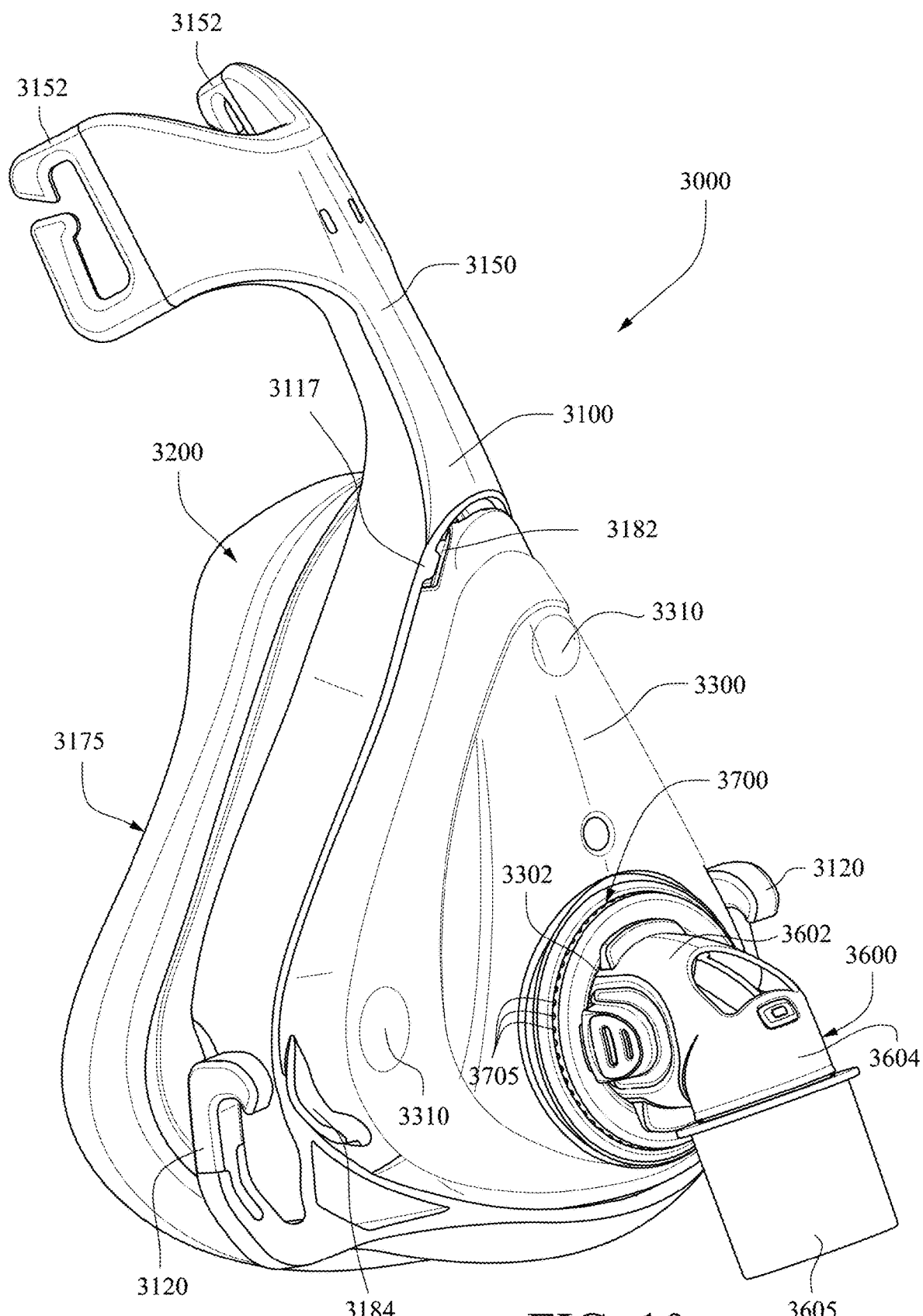

FIG. 10 is a perspective view of a patient interface according to an example of the present technology, the patient interface being shown with the anterior wall member engaged with the cushion assembly.

Figure 11A:
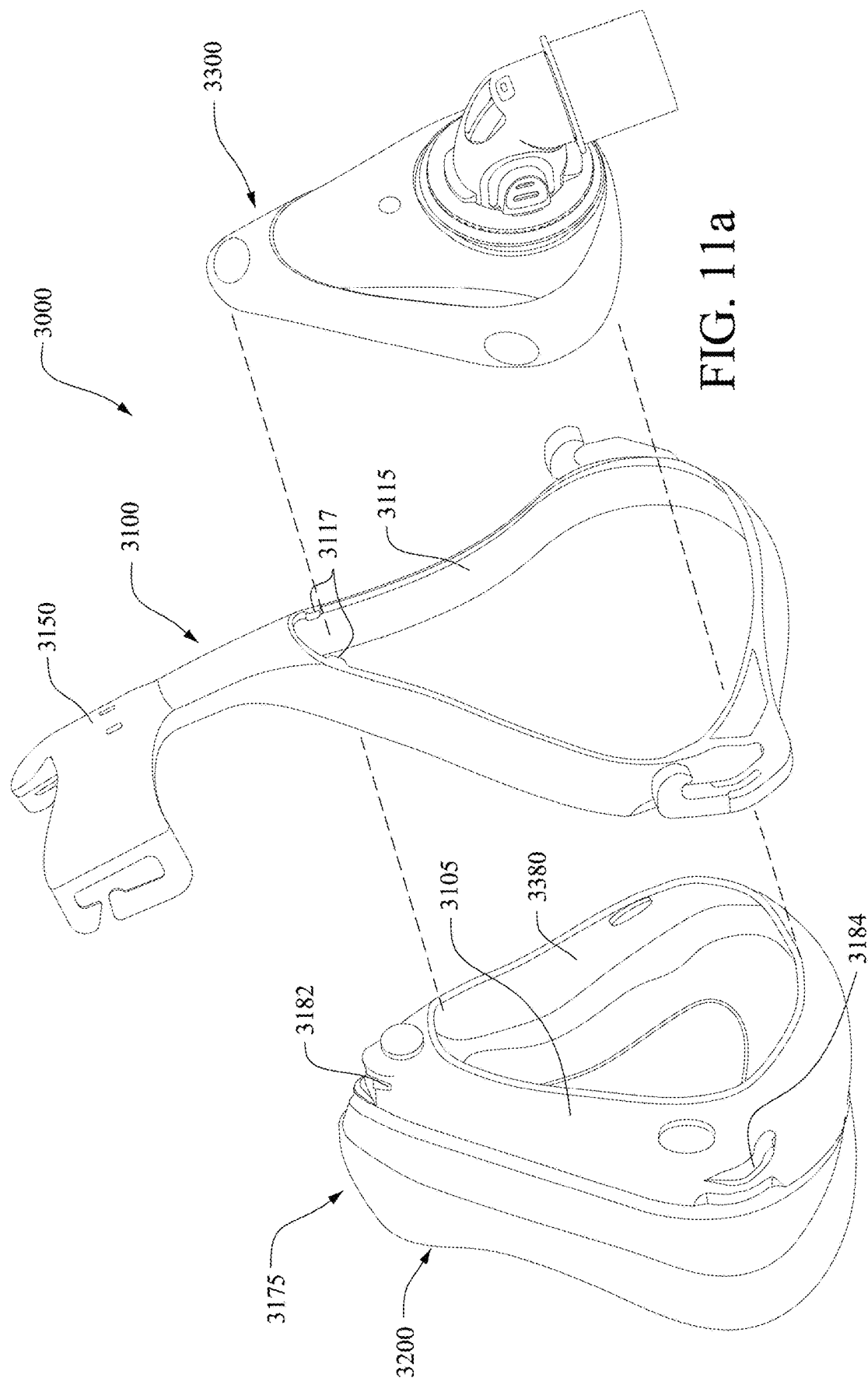

FIG. 11a is an exploded view of the patient interface shown in FIG. 10.

Figure 11B:
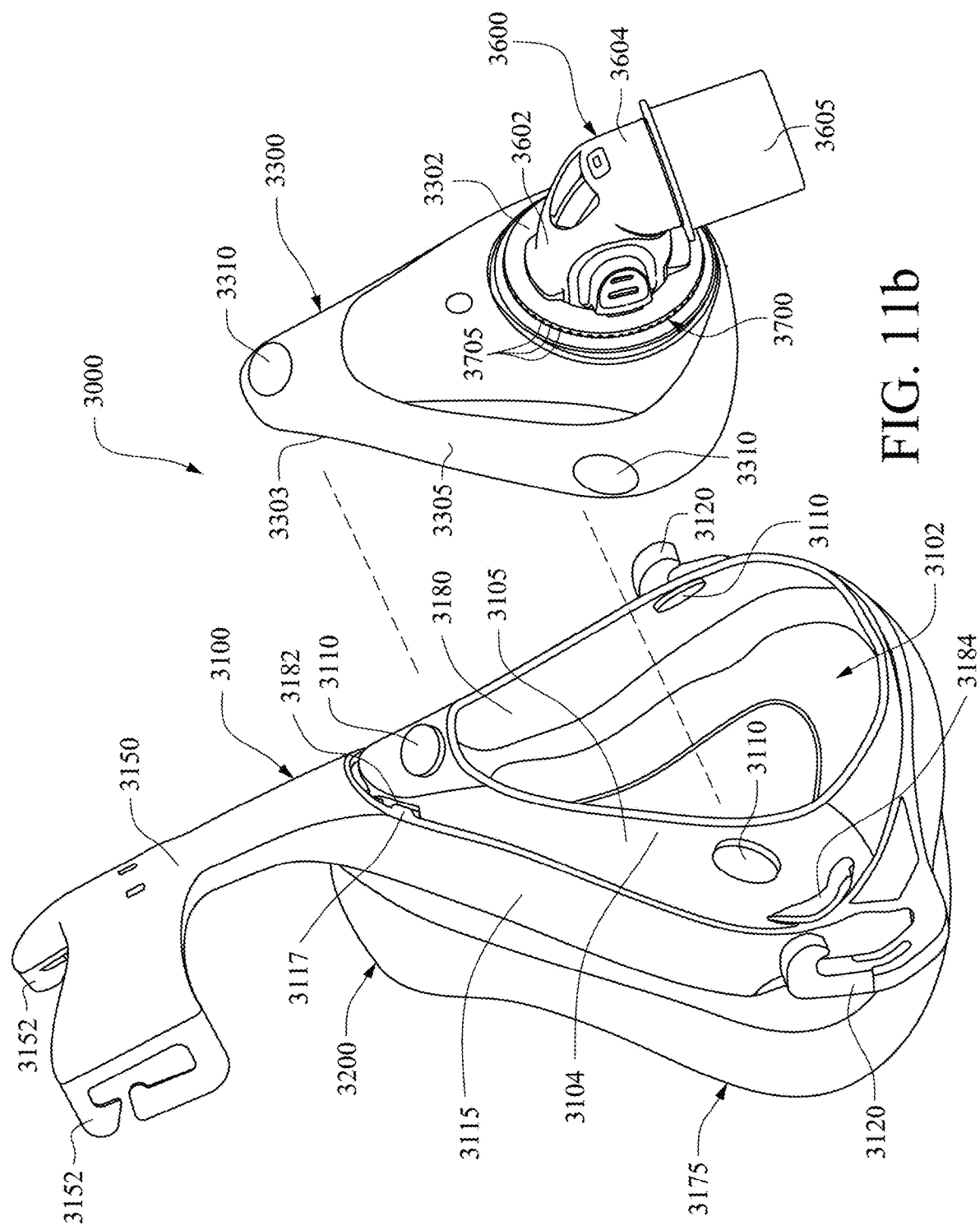

FIG. 11b is another exploded view of the patient interface shown in FIG. 10 showing the frame member engaged with the cushion assembly and the anterior wall member disengaged and removed from the cushion assembly.

Figure 12:
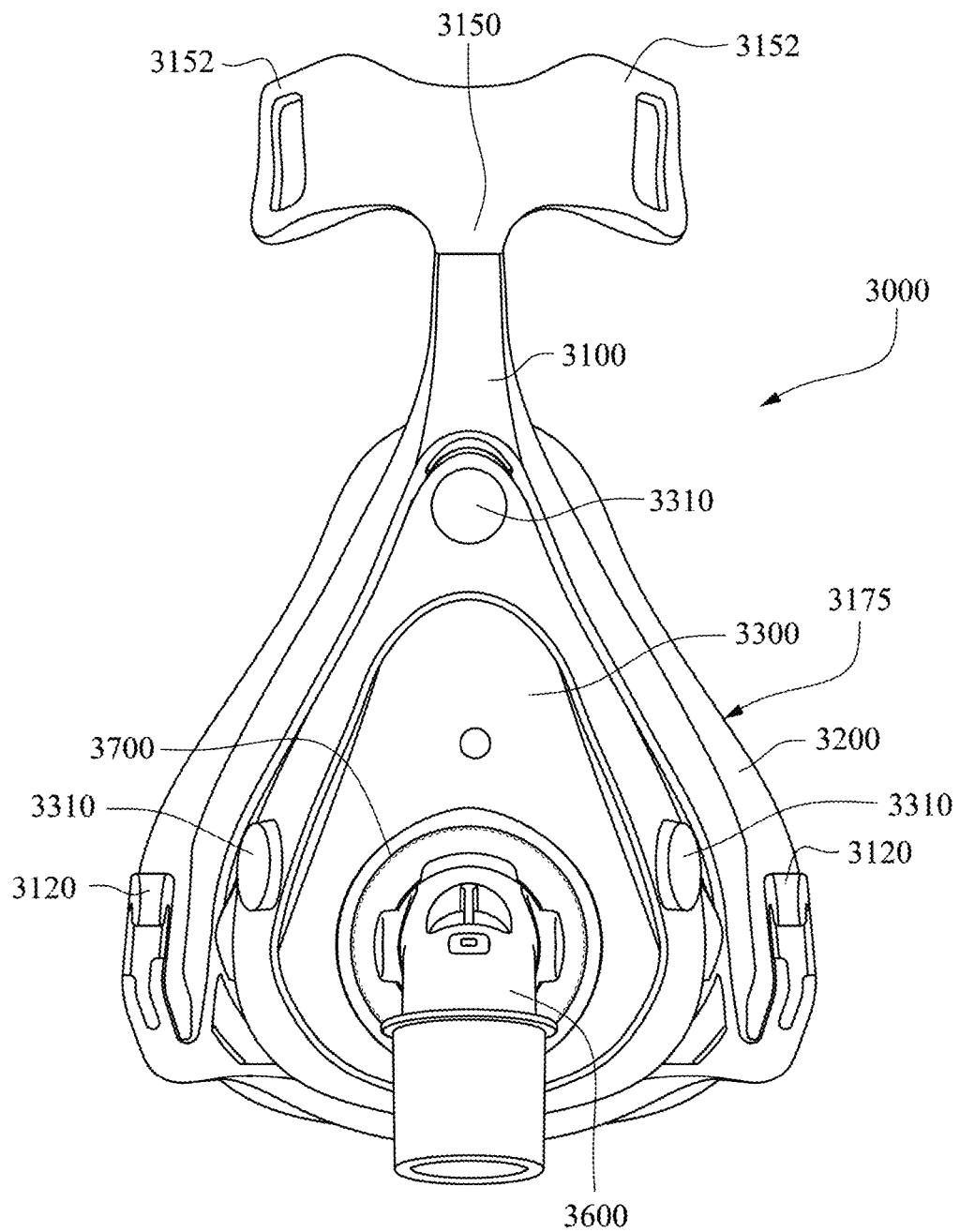

FIG. 12 is a front view of the patient interface shown in FIG. 10.

Figure 13:
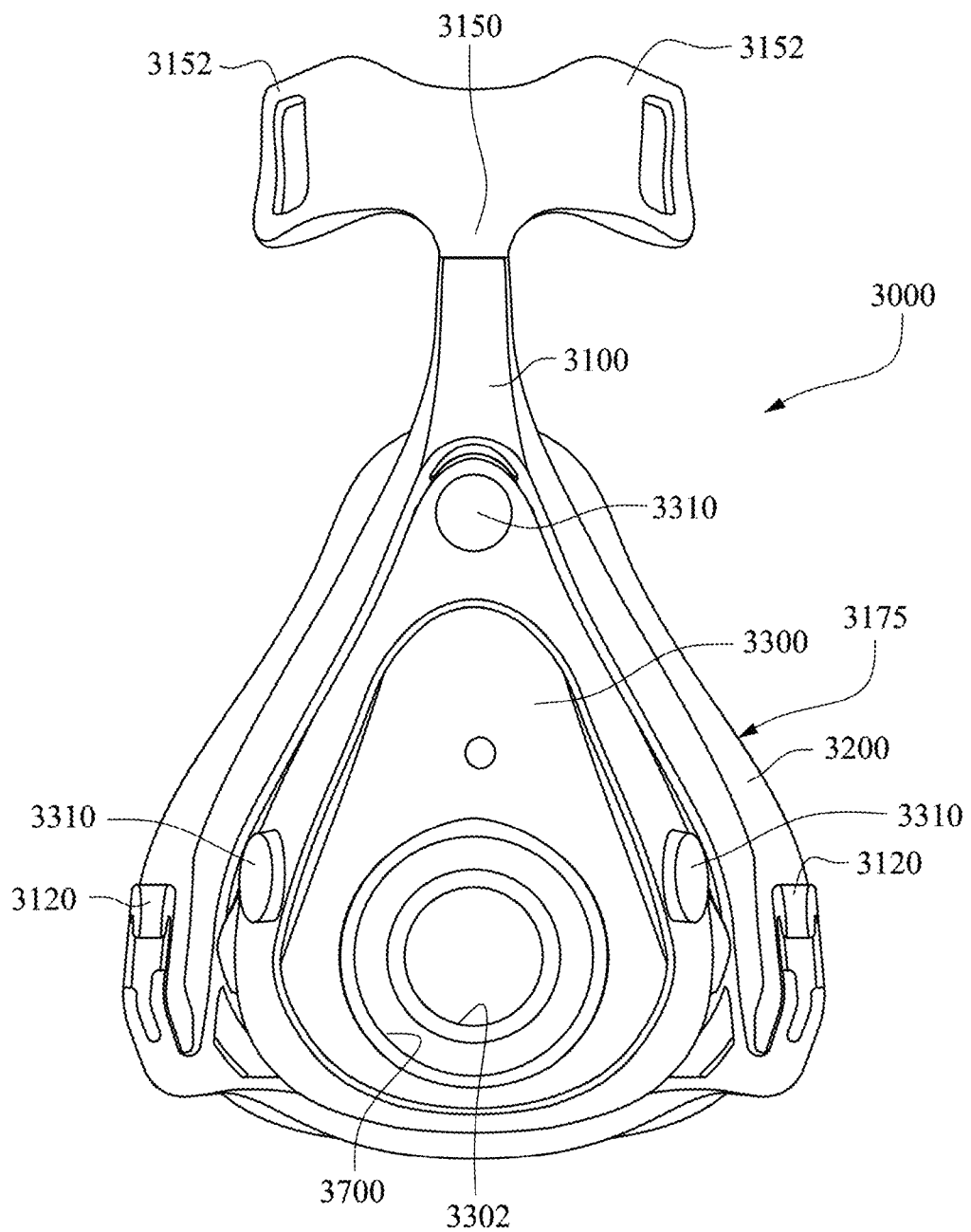

FIG. 13 is a front view of the patient interface shown in FIG. 10, the patient interface being shown with a swivel elbow disengaged from the anterior wall member.

Figure 14:
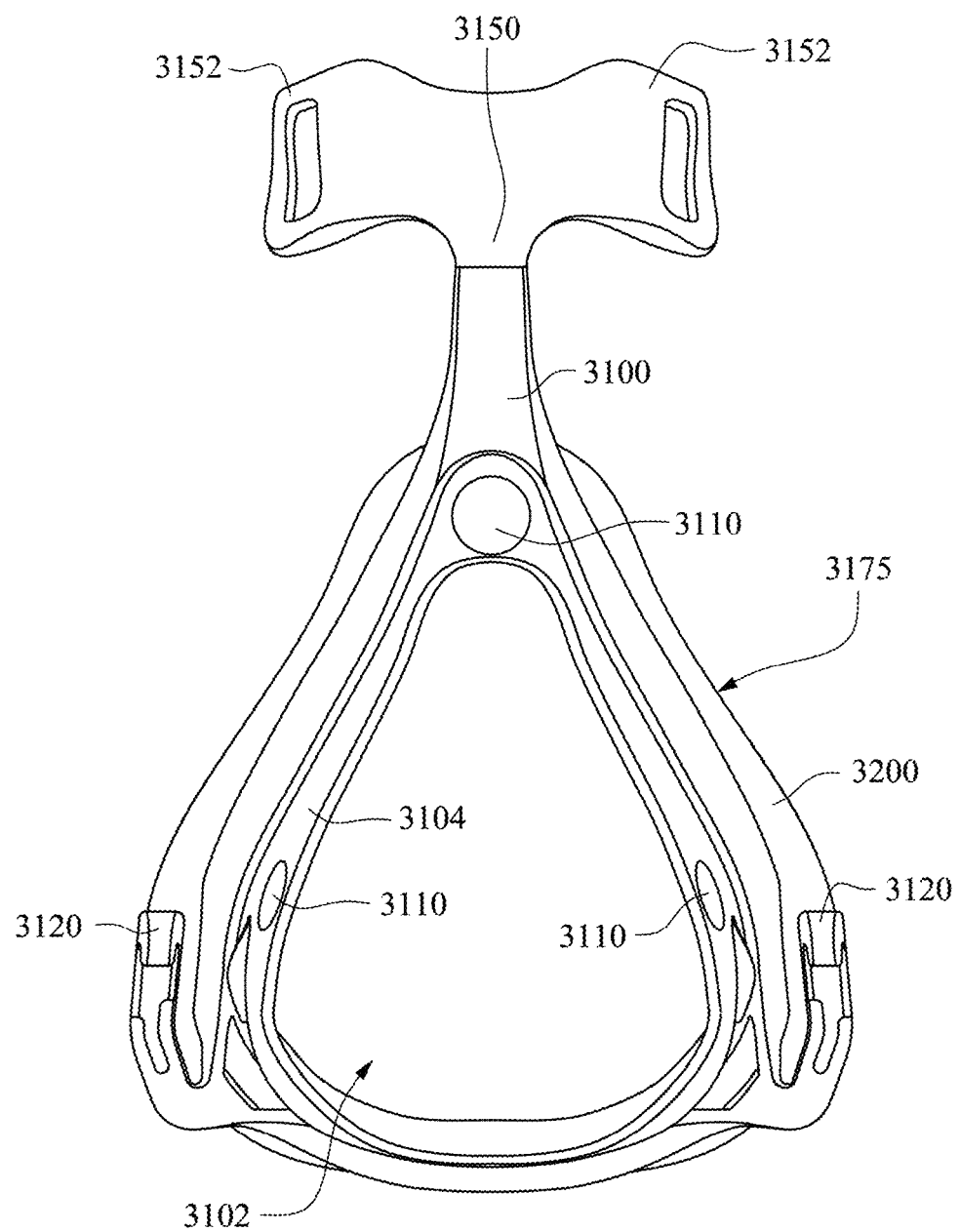

FIG. 14 is a front view of a frame member and cushion assembly of a patient interface shown in FIG. 10.

Figure 15:
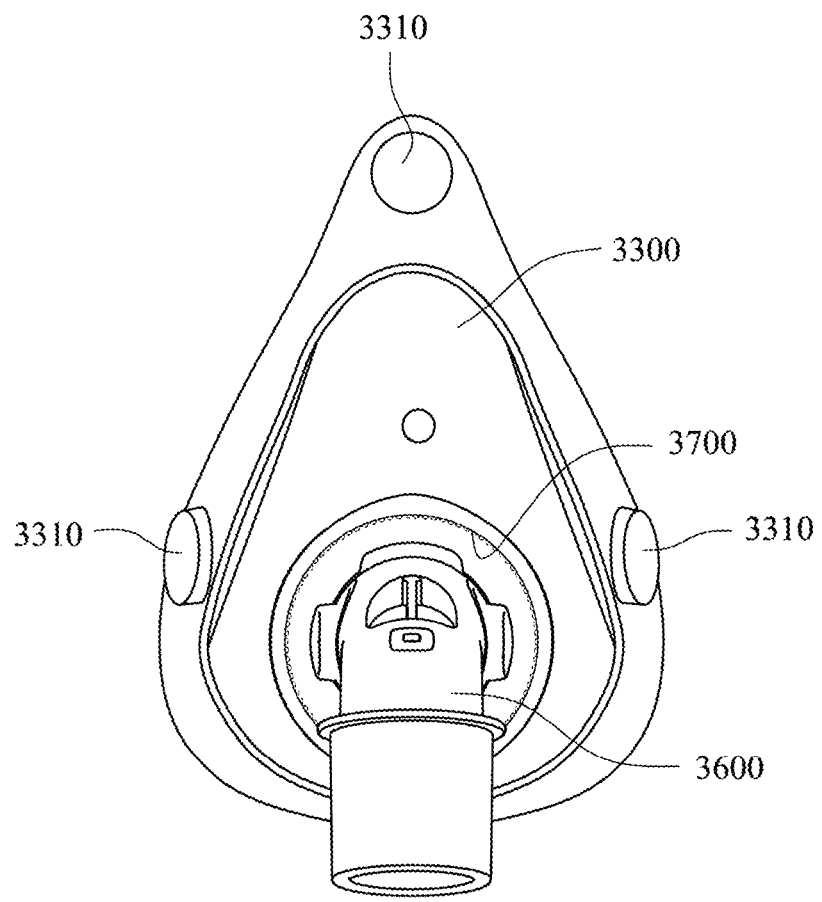

FIG. 15 is a front view of an anterior wall member and a swivel elbow of a patient interface shown in FIG. 10.

Figure 16:
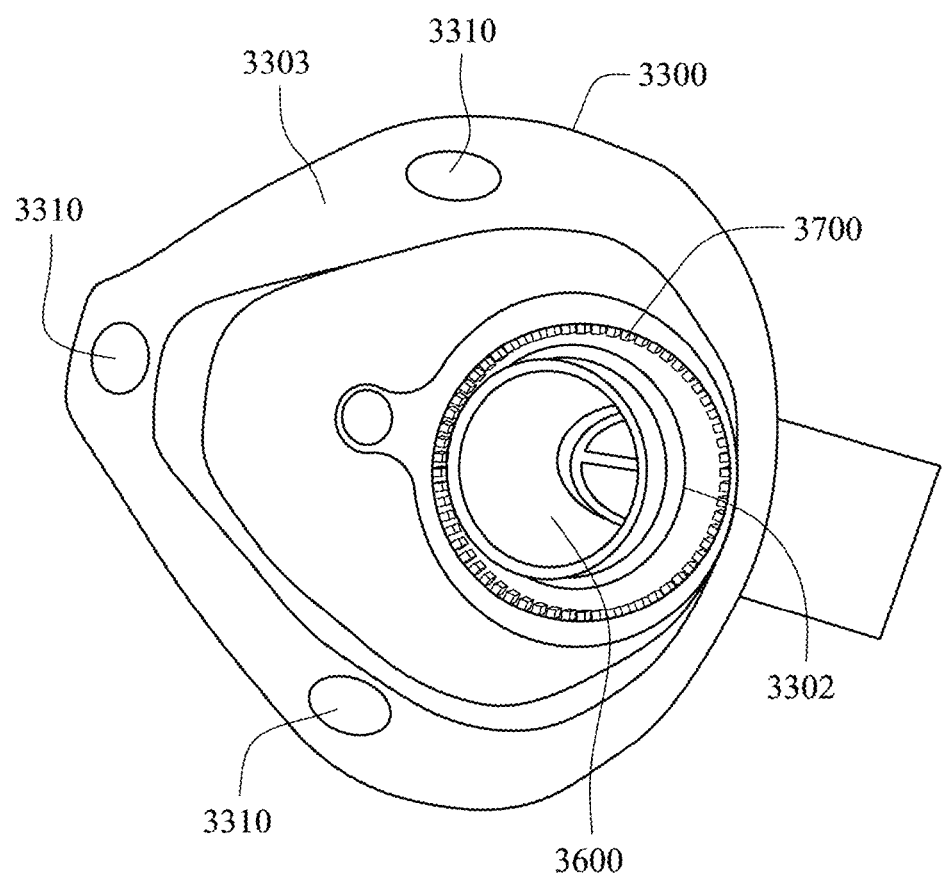

FIG. 16 is a rear perspective view of the anterior wall member and the swivel elbow shown in FIG. 15.

Figure 17:
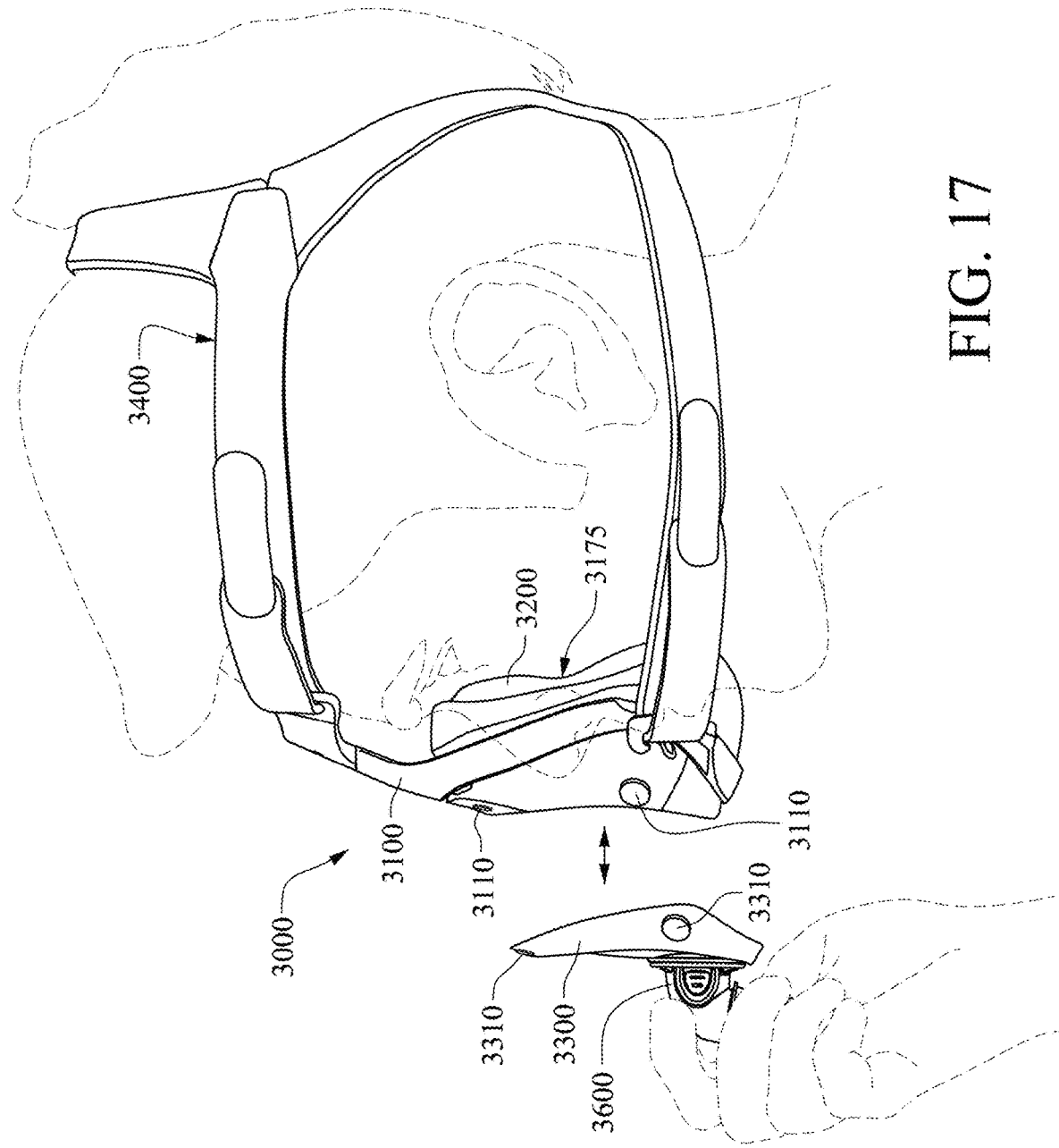

FIG. 17 is a side view showing the act of engaging an anterior wall member with a cushion assembly of a patient interface shown on a patient's head according to an example of the present technology.

Figure 18:
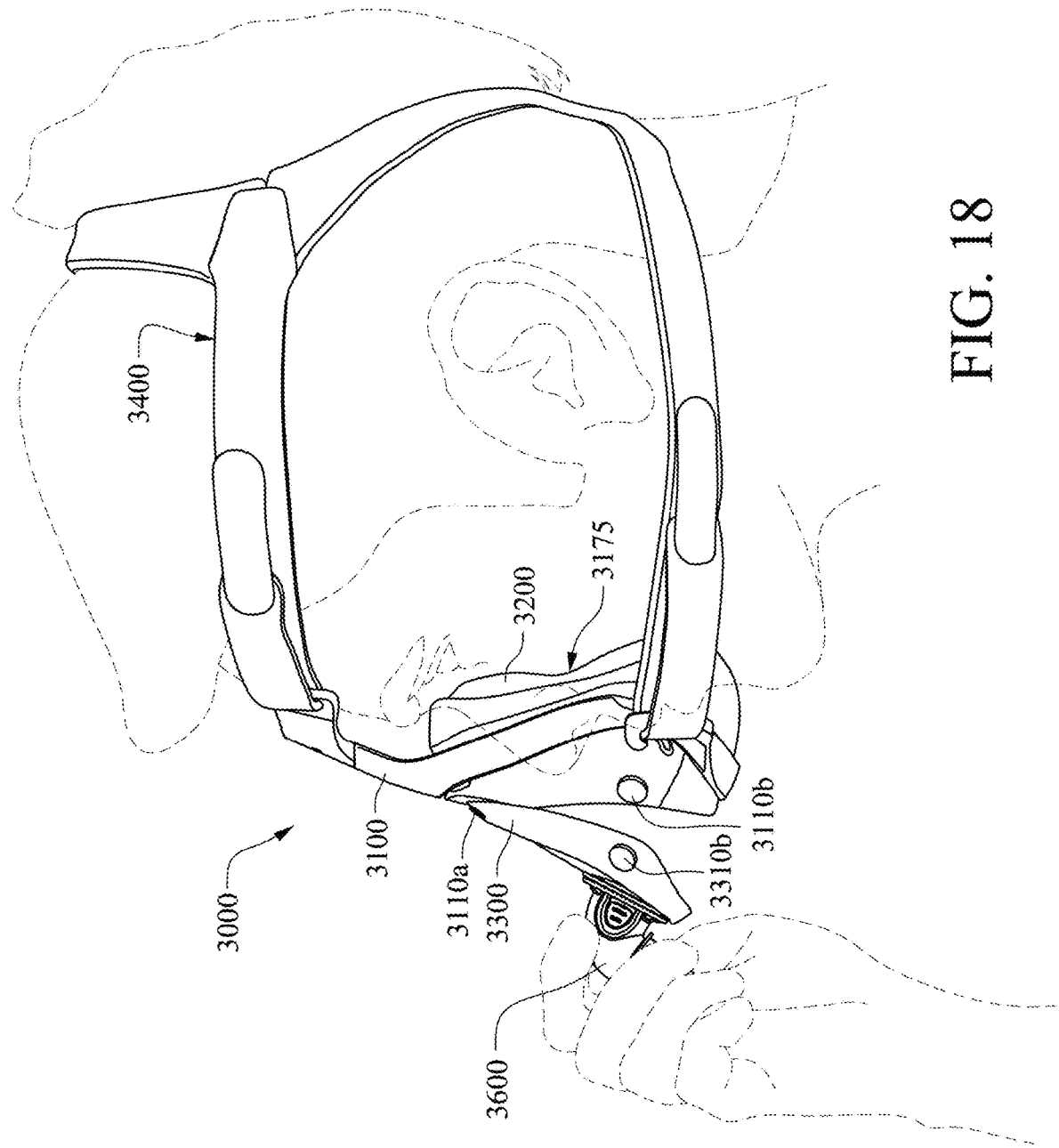
Figure 21:
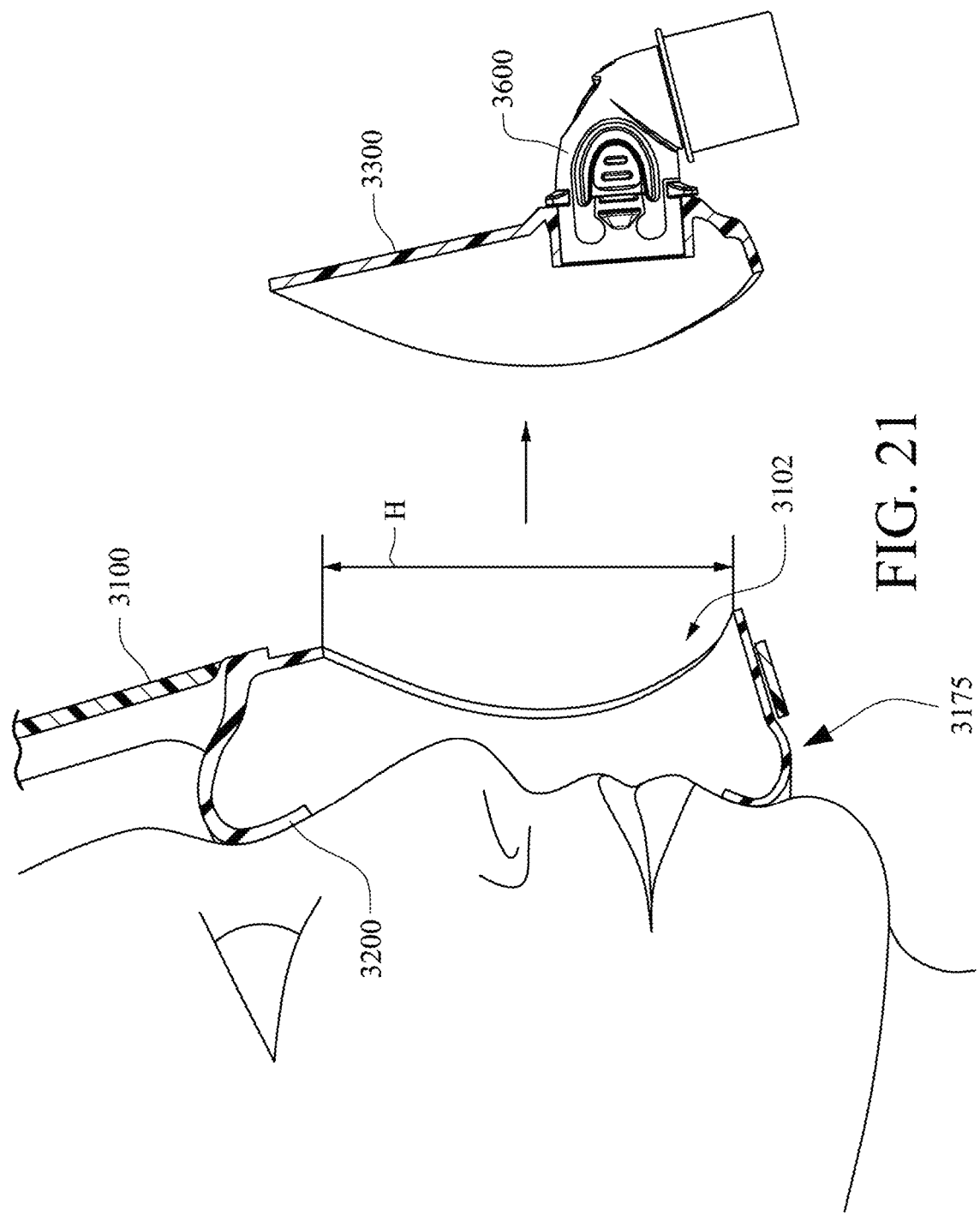

FIG. 18 is a side view showing the act of engaging an anterior wall member with a cushion assembly of a patient interface shown on a patient's head according to another example of the present technology.

FIGS. 19a and 19b are side views showing the act of engaging an anterior wall member with a cushion assembly of a patient interface according to an example of the present technology.

FIG. 19c is a schematic top view showing the act of engaging an anterior wall member with a cushion assembly of a patient interface according to an example of the present technology.

FIG. 20a is a cross-sectional view of a patient interface according to an example of the present technology, the patient interface being shown with the anterior wall member engaged with the cushion assembly.

FIG. 20b is an exploded cross-sectional view of the patient interface shown in FIG. 20a showing the anterior wall member disengaged from the cushion assembly.

Figure 21:
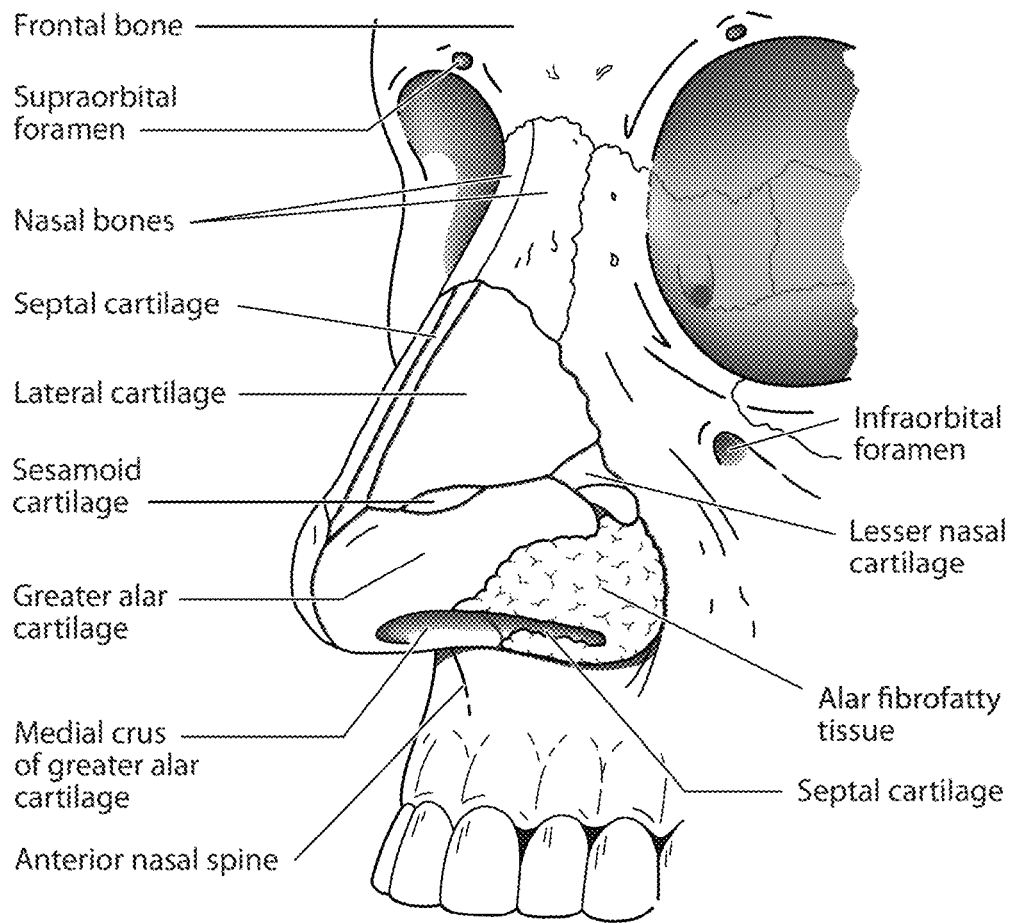

FIG. 21 is a cross-sectional view of a patient interface according to an example of the present technology, the patient interface being shown with the anterior wall member disengaged from the cushion assembly to show the size of the opening provided by the cushion assembly.

Figure 22:
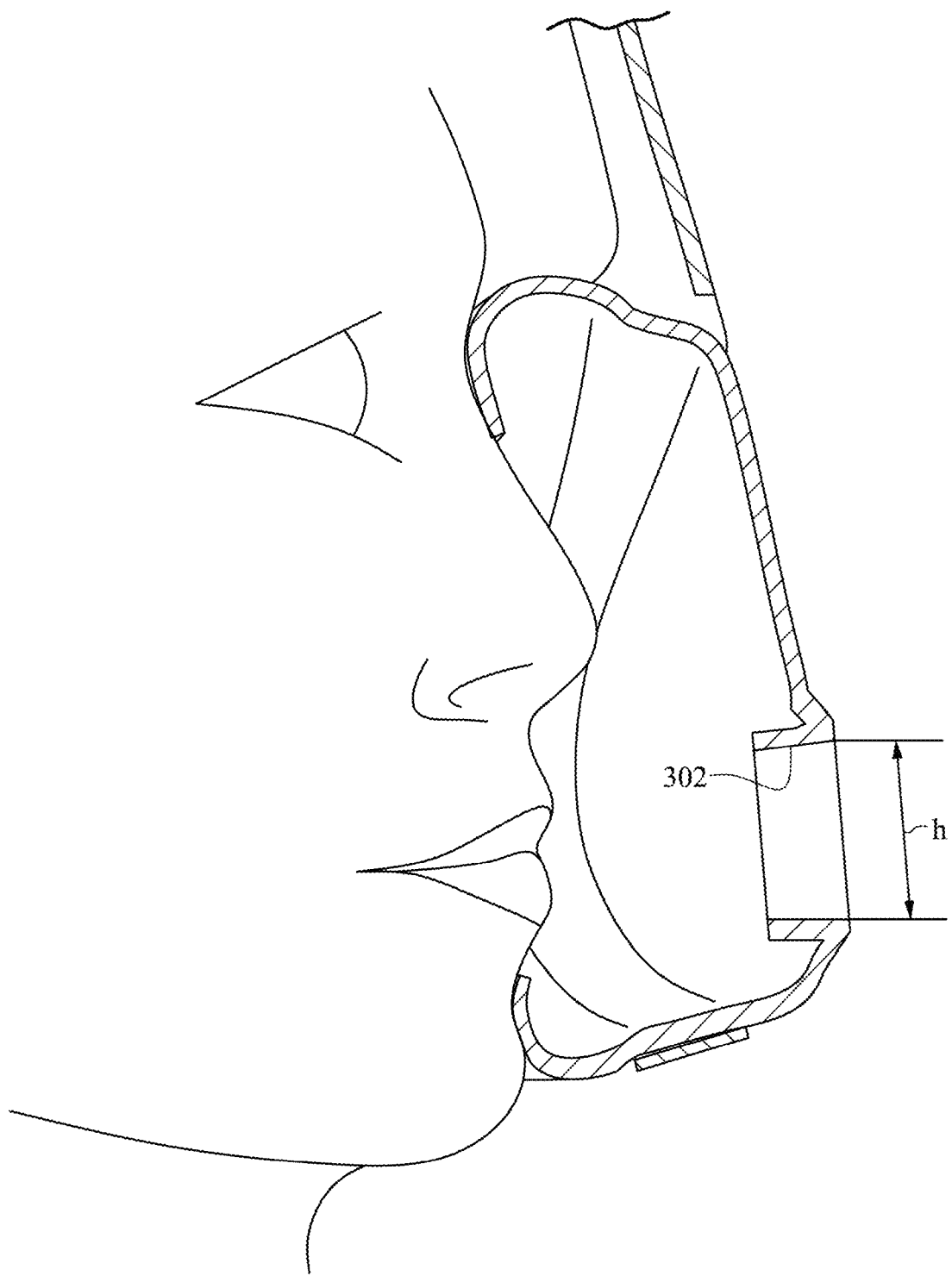

FIG. 22 is a cross-sectional view of a patient interface including a cushion assembly without a disengageable anterior wall member to show the size of the opening provided by the cushion assembly.

Figure 23:
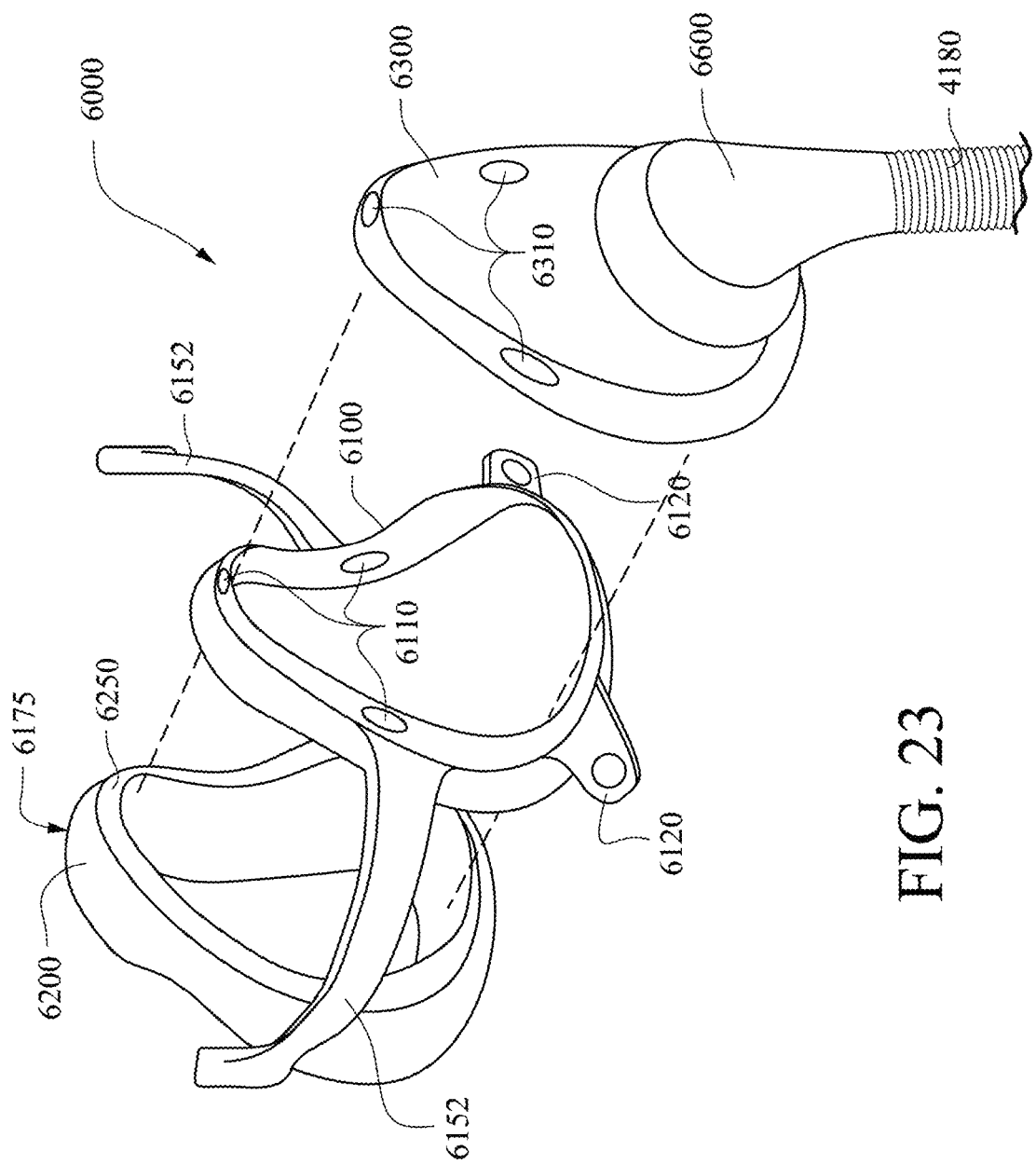

FIG. 23 is an exploded perspective view of a patient interface according to another example of the present technology.

Figure 24A:
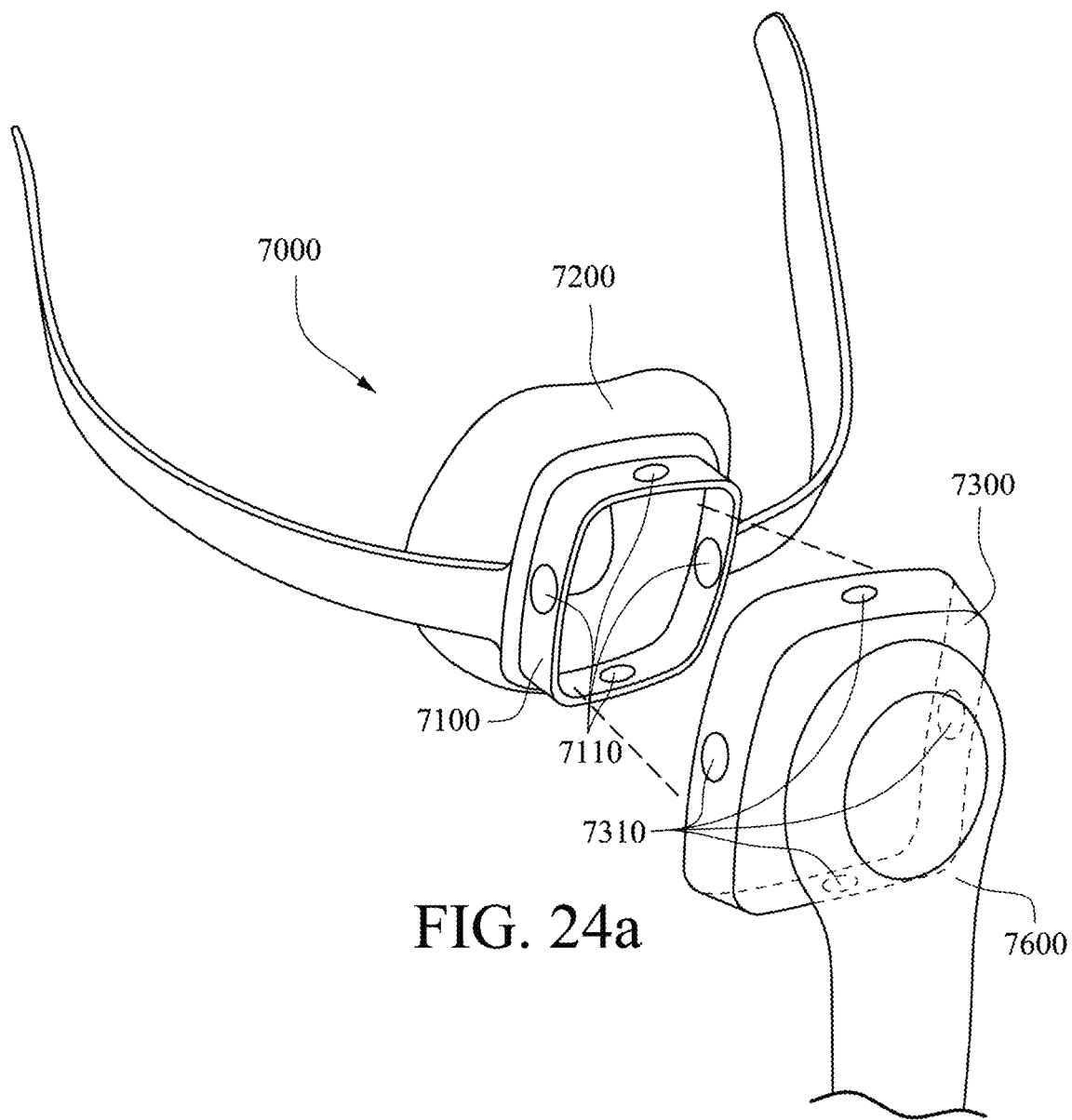

FIG. 24a is an exploded perspective view of a patient interface according to another example of the present technology.

Figure 24B:
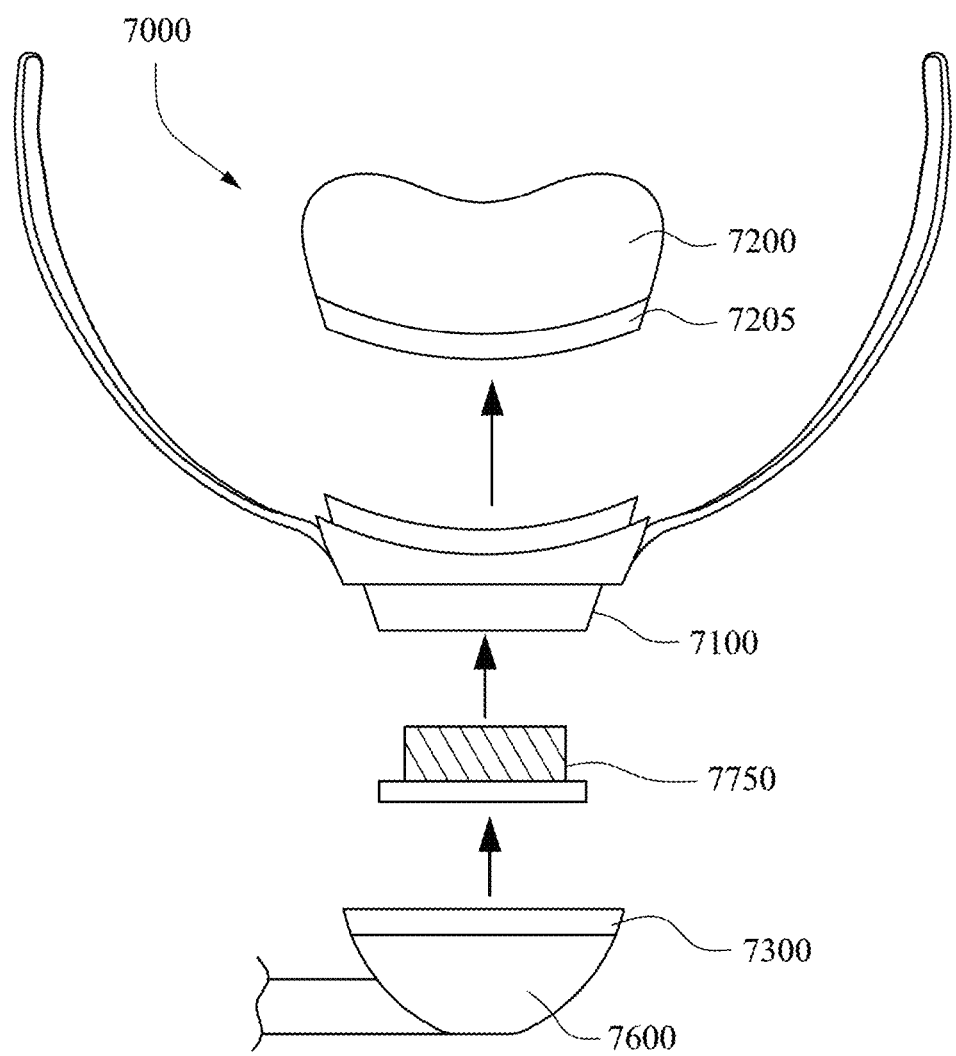

FIG. 24b is an exploded plan view of the patient interface of FIG. 24a according to an example of the present technology.

Figure 25A:
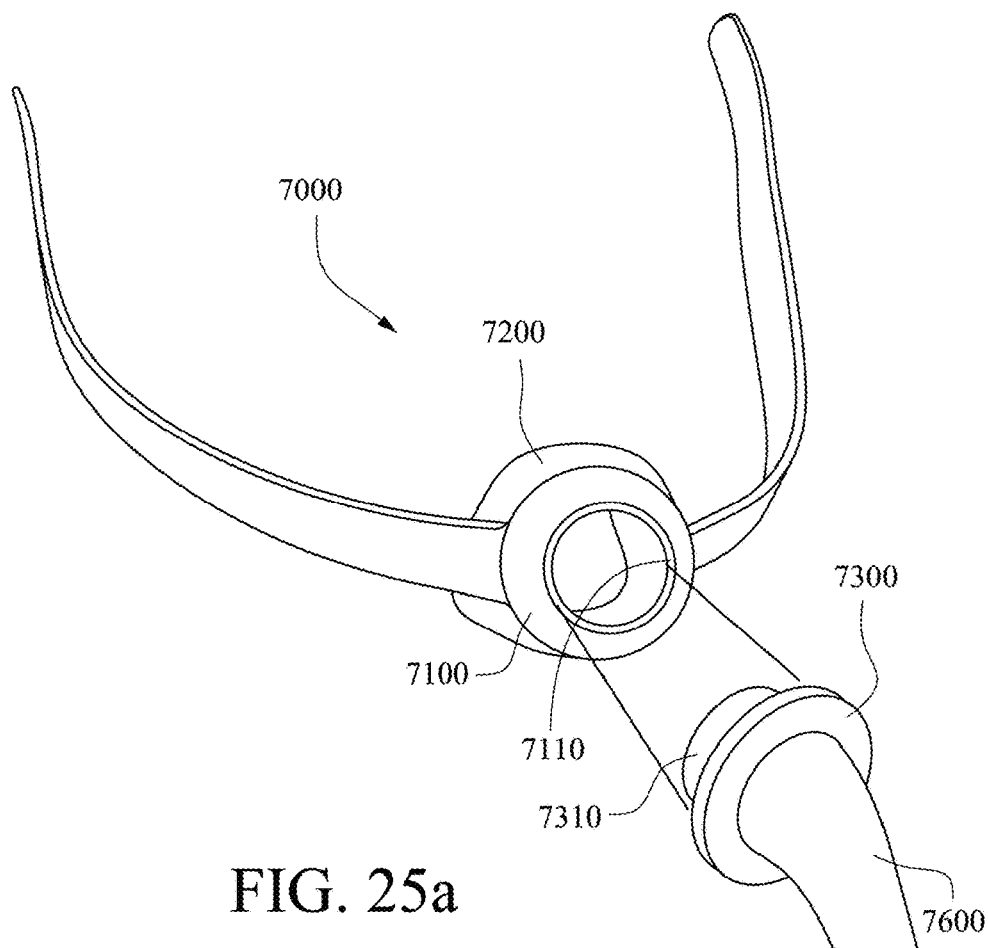

FIG. 25a is an exploded perspective view of a patient interface according to another example of the present technology.

Figure 25B:
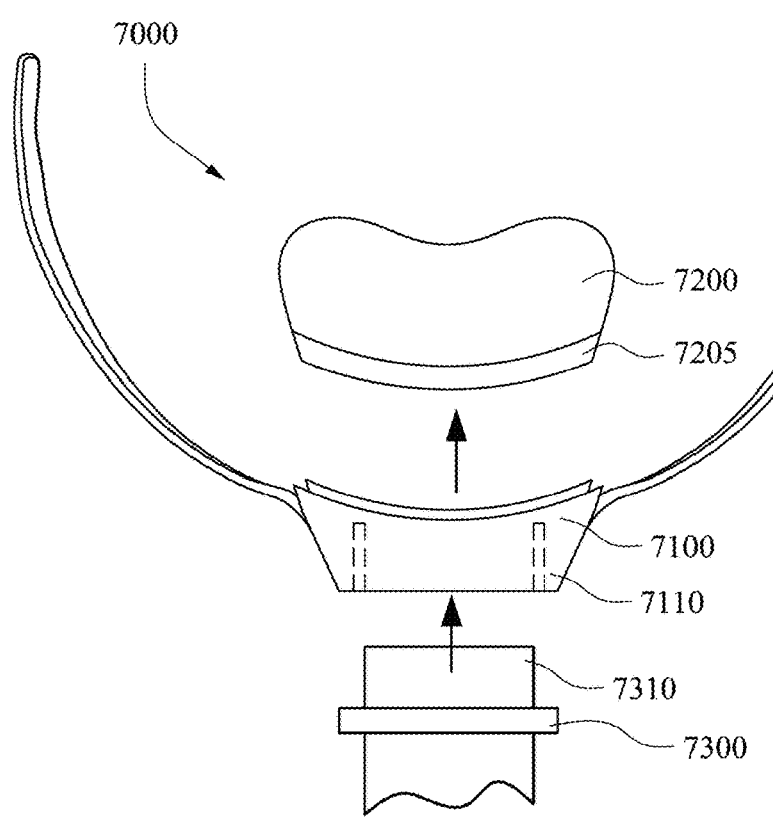

FIG. 25b is an exploded plan view of the patient interface of FIG. 25a according to an example of the present technology.

Figure 26A:
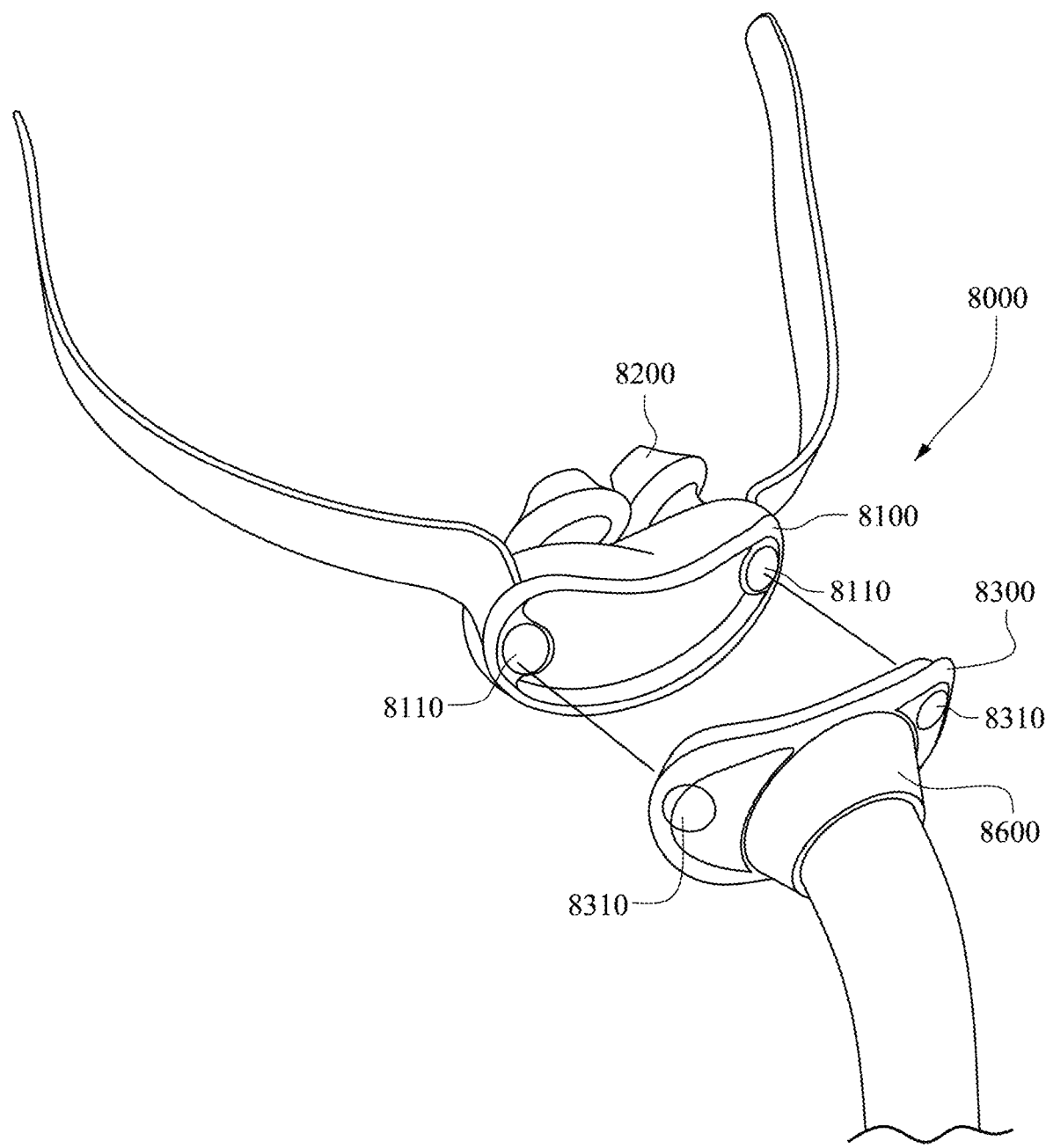

FIG. 26a is an exploded perspective view of a patient interface according to another example of the present technology.

Figure 26B:
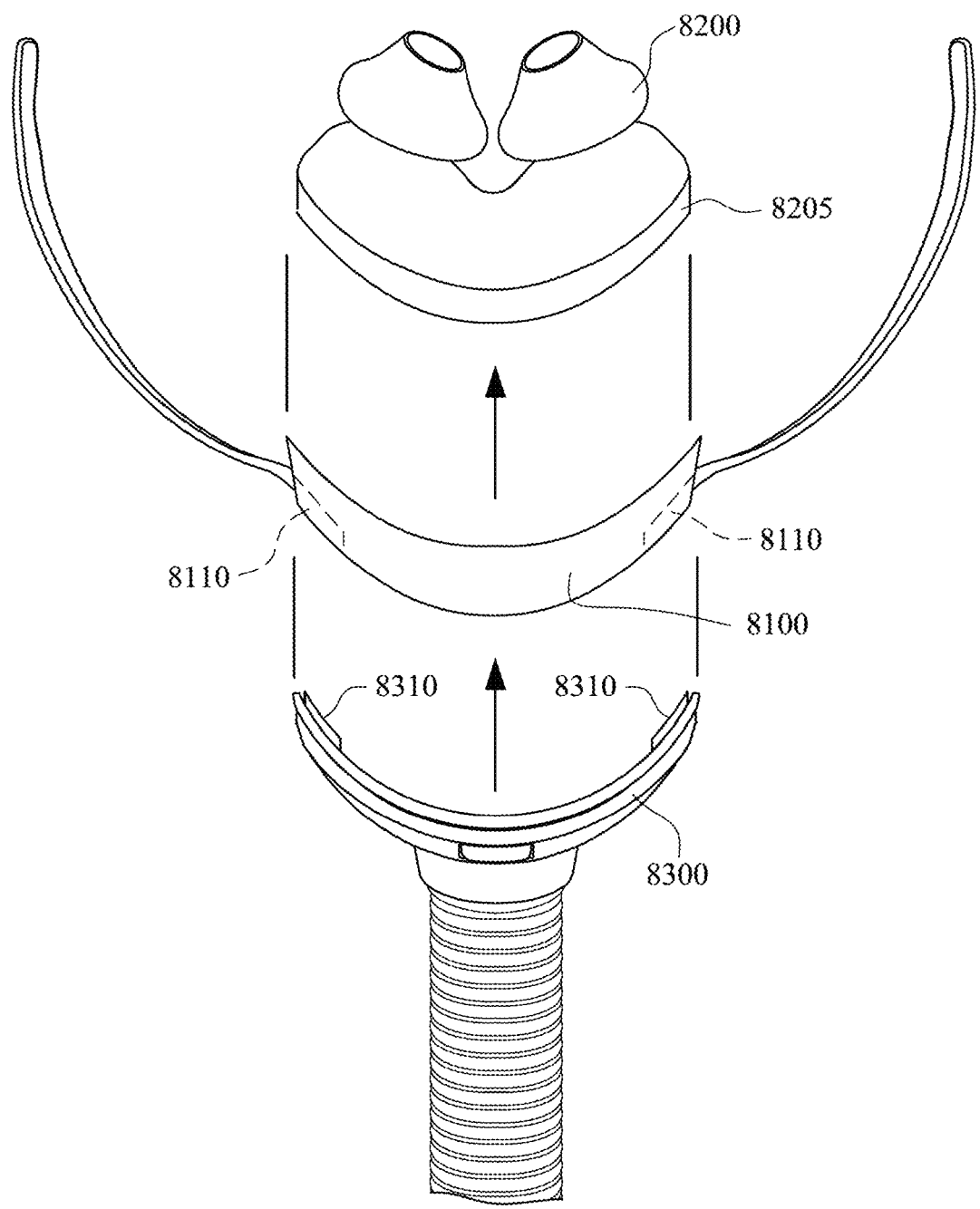

FIG. 26b is an exploded plan view of the patient interface of FIG. 26a according to an example of the present technology.

Figure 27:
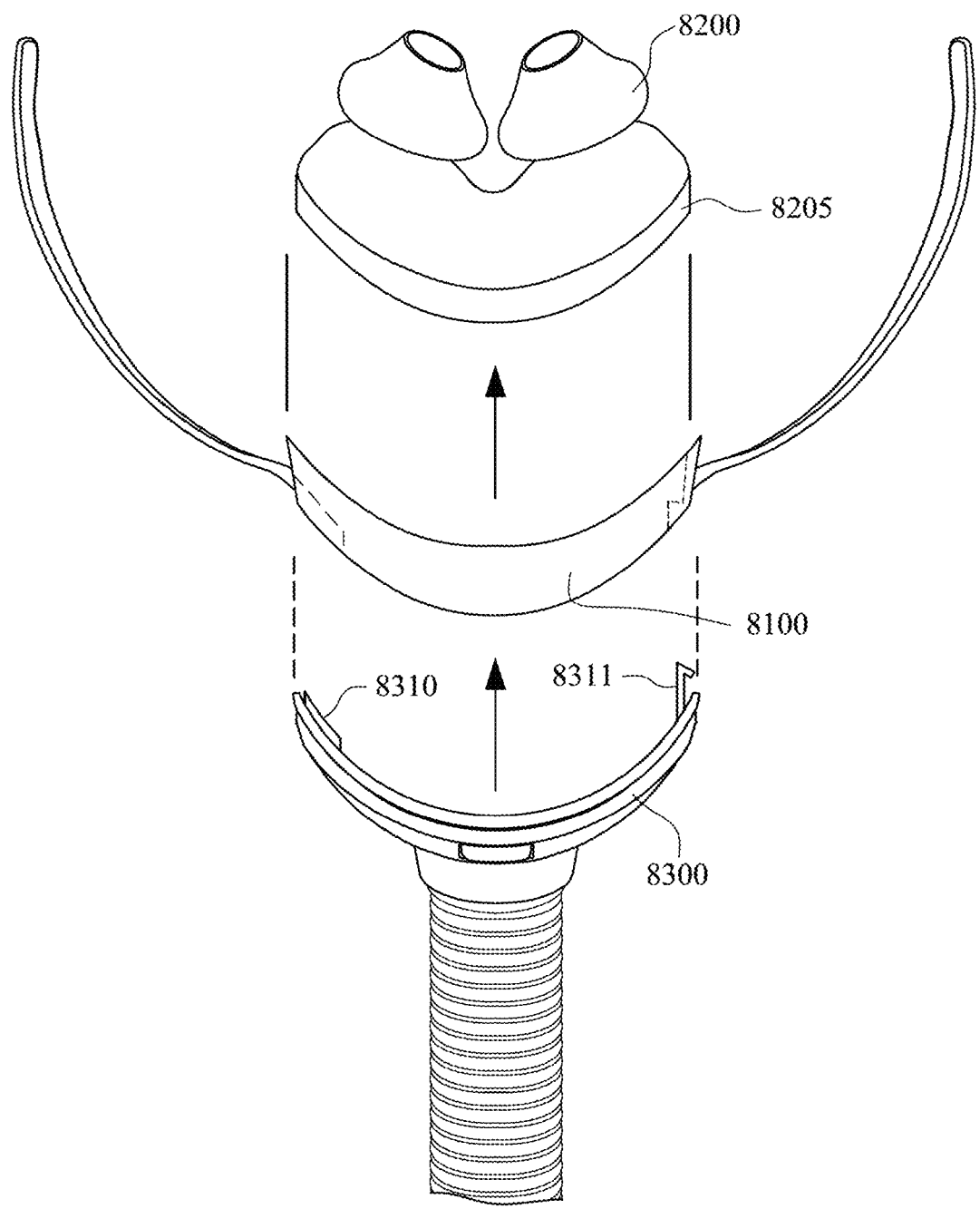

FIG. 27 is an exploded plan view of a patient interface according to another example of the present technology.

Figure 28:
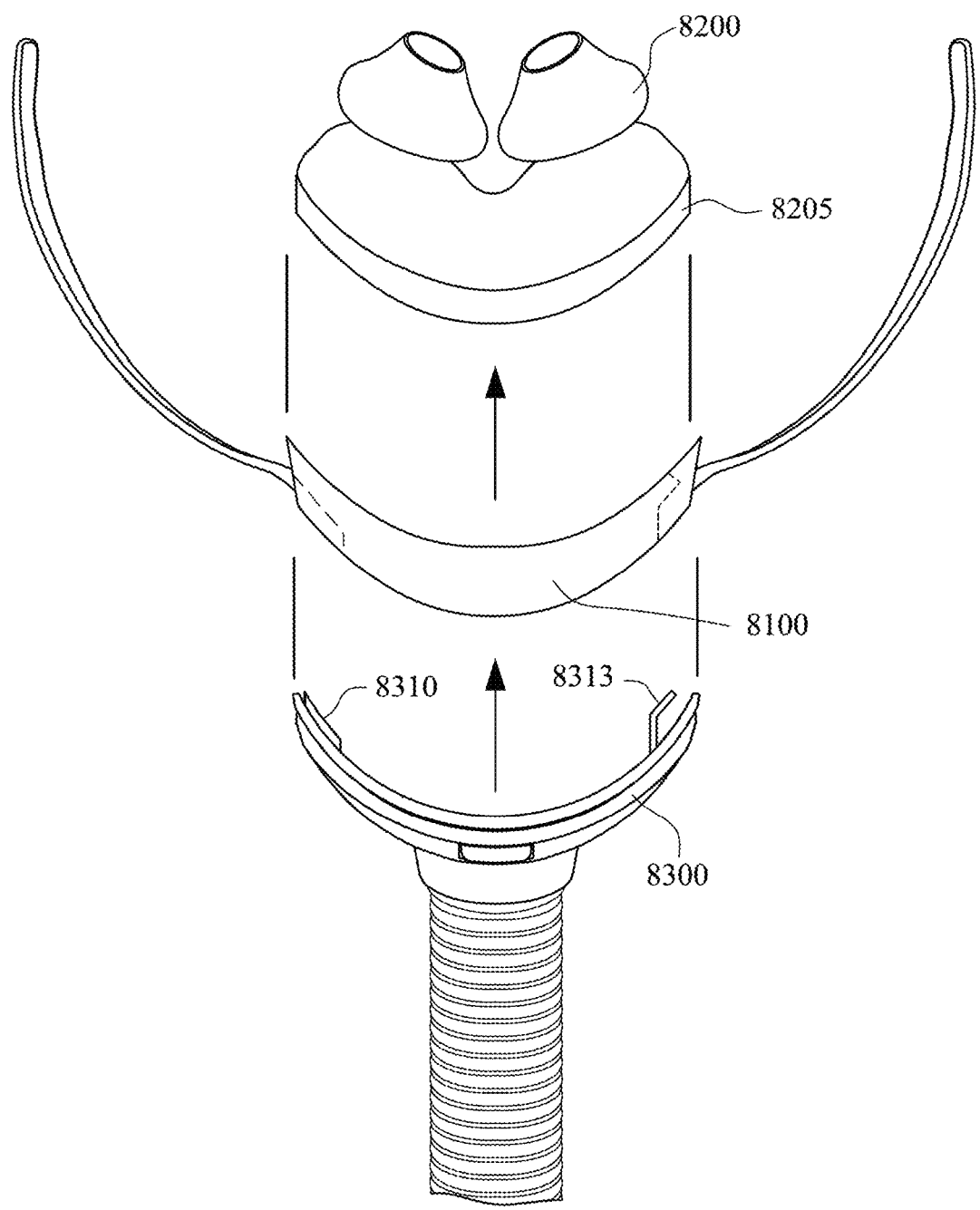

FIG. 28 is an exploded plan view of a patient interface according to another example of the present technology.

Figure 29:
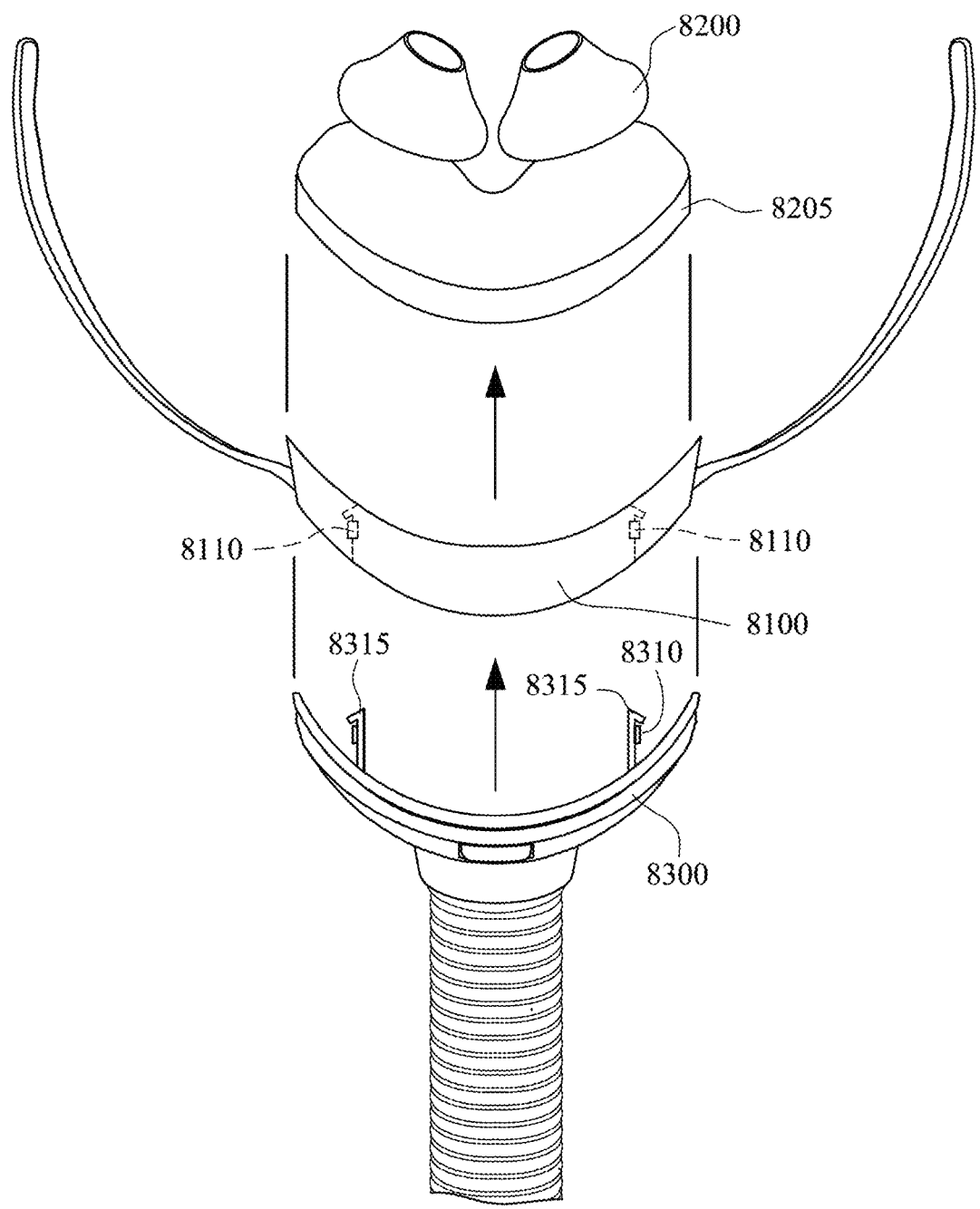

FIG. 29 is an exploded plan view of the patient interface of FIG. 26 according to an example of the present technology.

Figure 30:
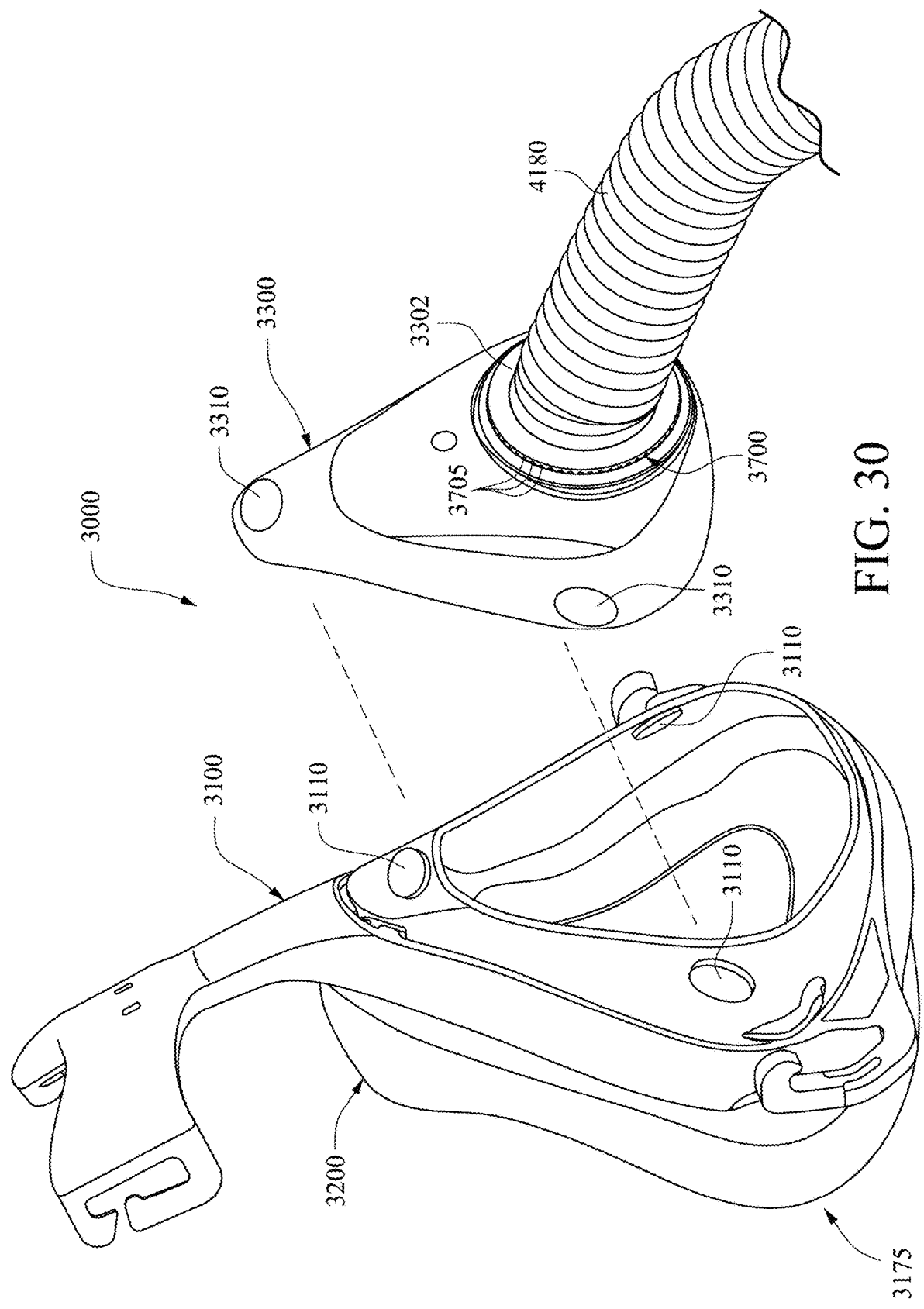

FIG. 30 is an exploded view of a patient interface according to an example of the present technology showing the anterior wall member disengaged and removed from the cushion assembly.

Figure 31:
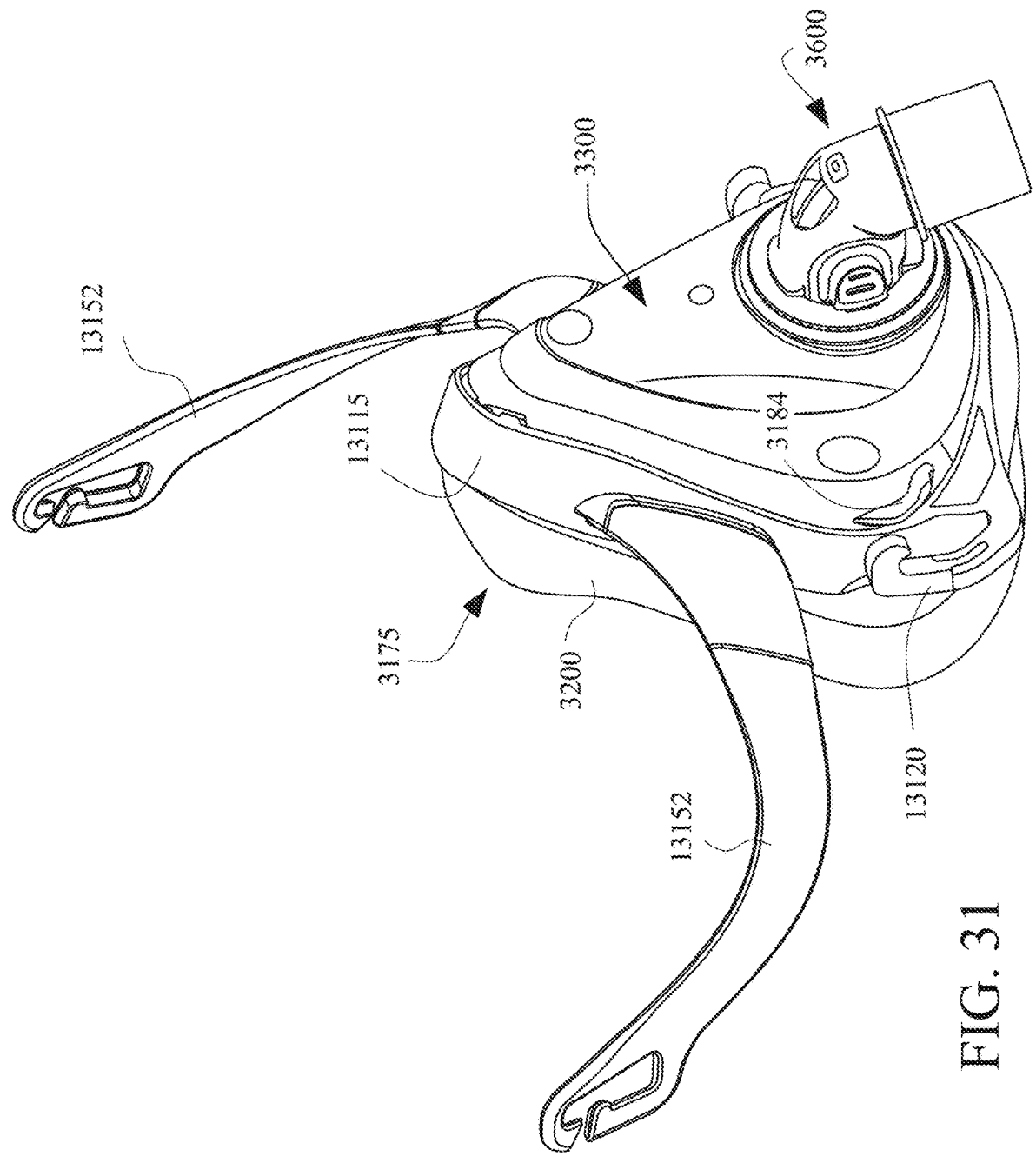

FIG. 31 is a perspective view of a patient interface according to another example of the present technology, the patient interface being shown with the anterior wall member engaged with the cushion assembly.

Figure 32:
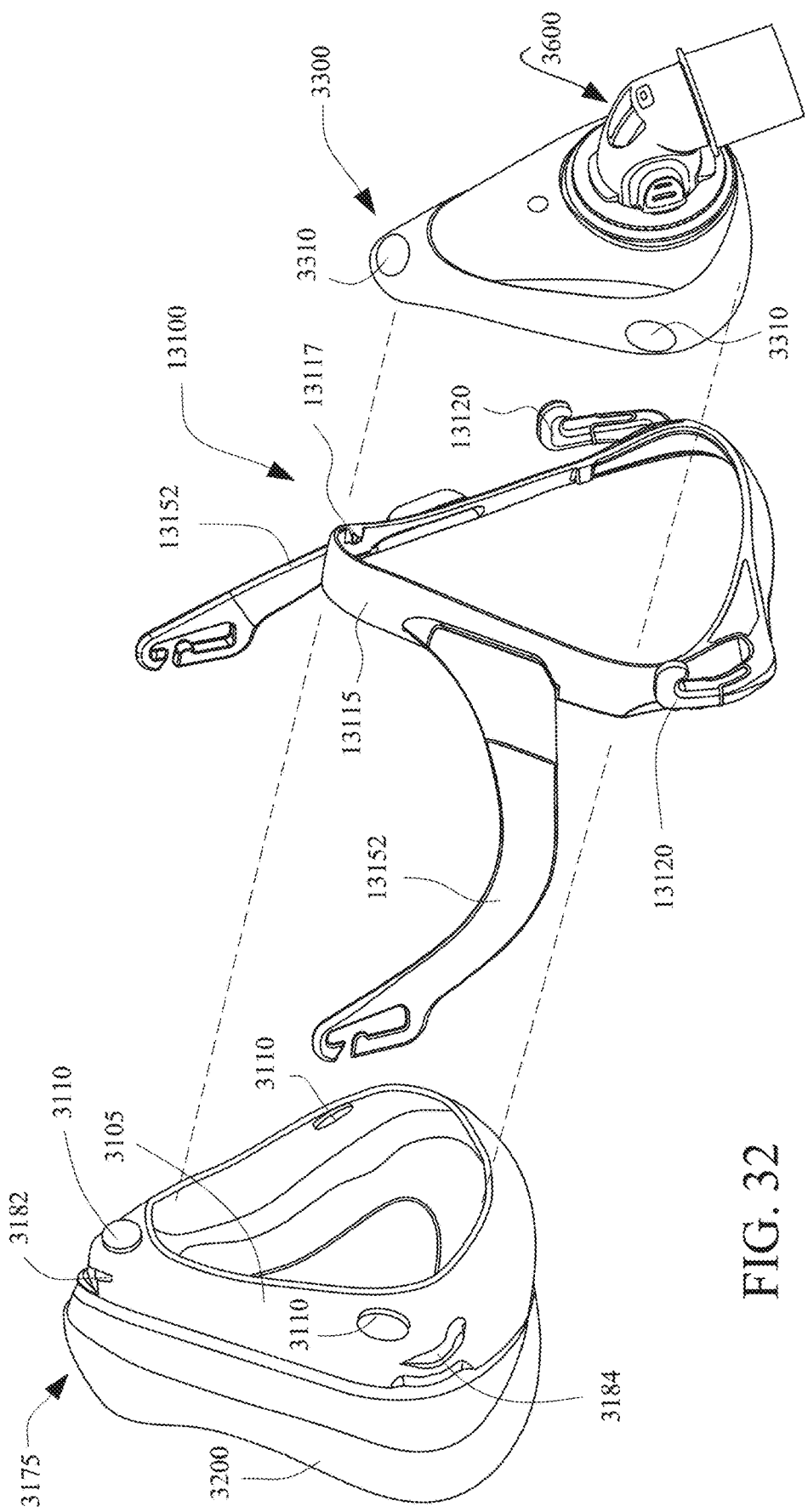

FIG. 32 is an exploded view of the patient interface shown in FIG. 31.

Figure 33:
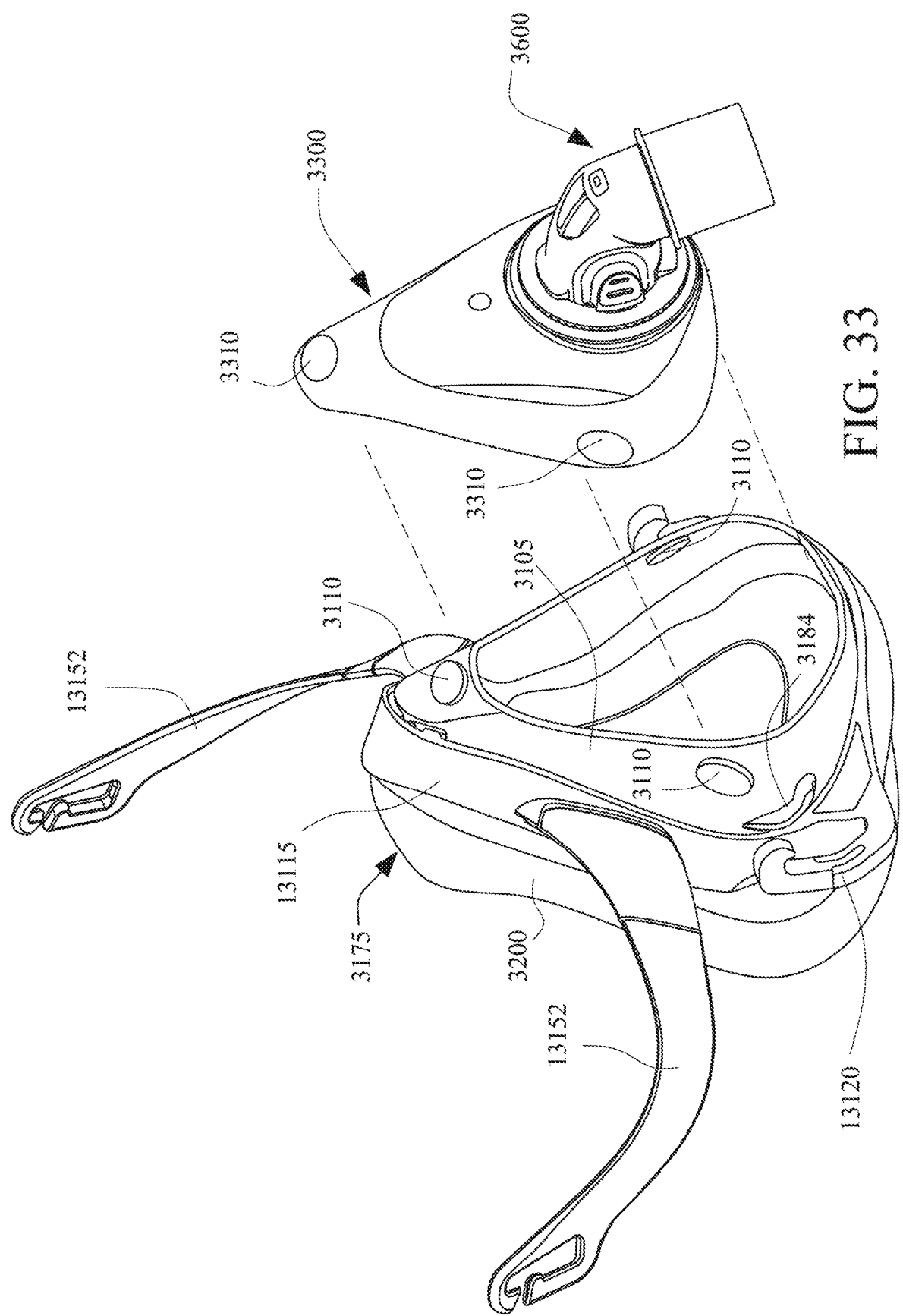

FIG. 33 is another exploded view of the patient interface shown in FIG. 31 showing the frame member engaged with the cushion assembly and the anterior wall member disengaged and removed from the cushion assembly.

Figure 34:
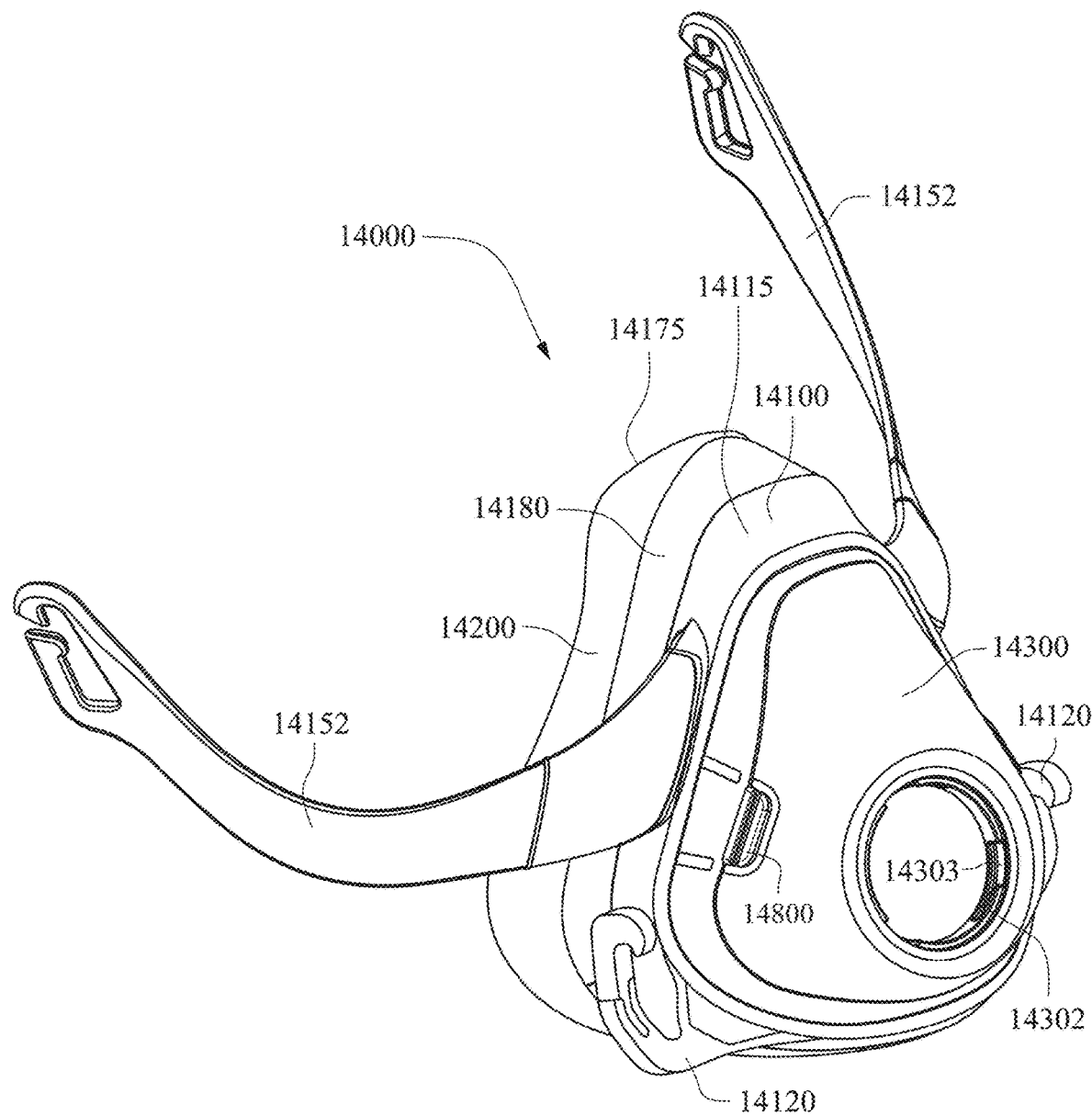

FIG. 34 is a perspective view of a patient interface according to another example of the present technology, the patient interface being shown with the anterior wall member engaged with the cushion assembly.

Figure 35:
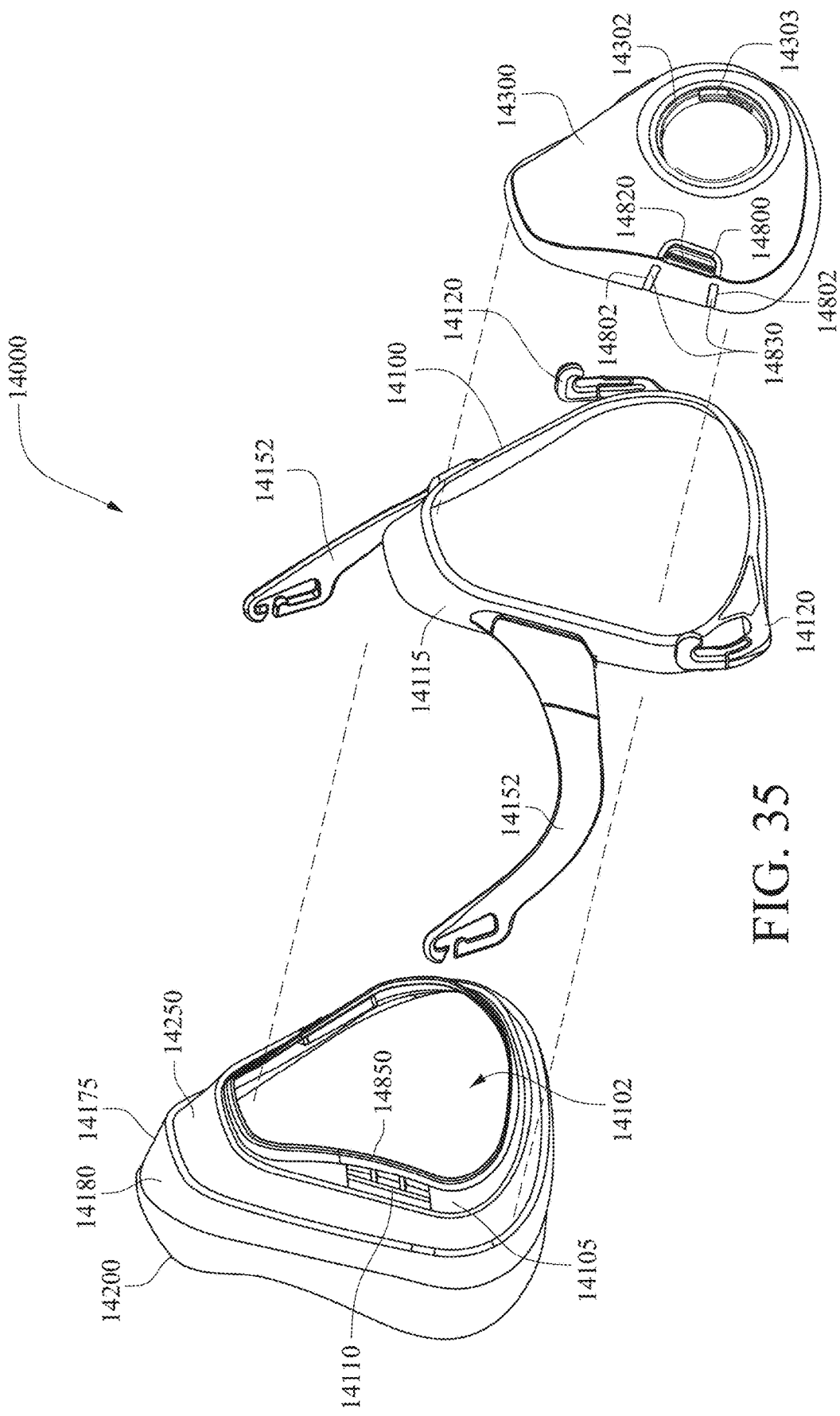

FIG. 35 is an exploded view of the patient interface shown in FIG. 34.

Figure 36:
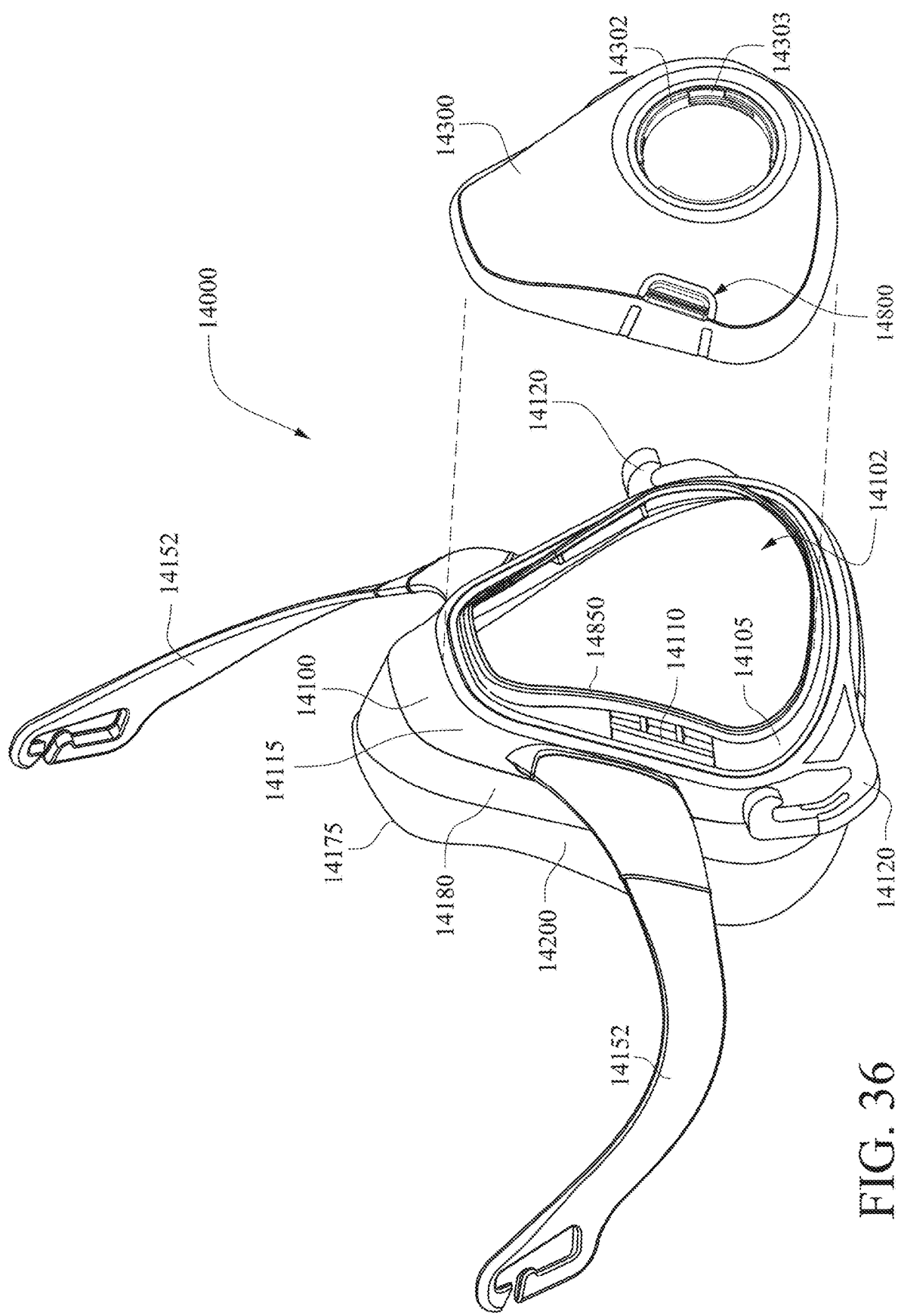

FIG. 36 is another exploded view of the patient interface shown in FIG. 34 showing the frame member engaged with the cushion assembly and the anterior wall member disengaged and removed from the cushion assembly.

Figure 37:
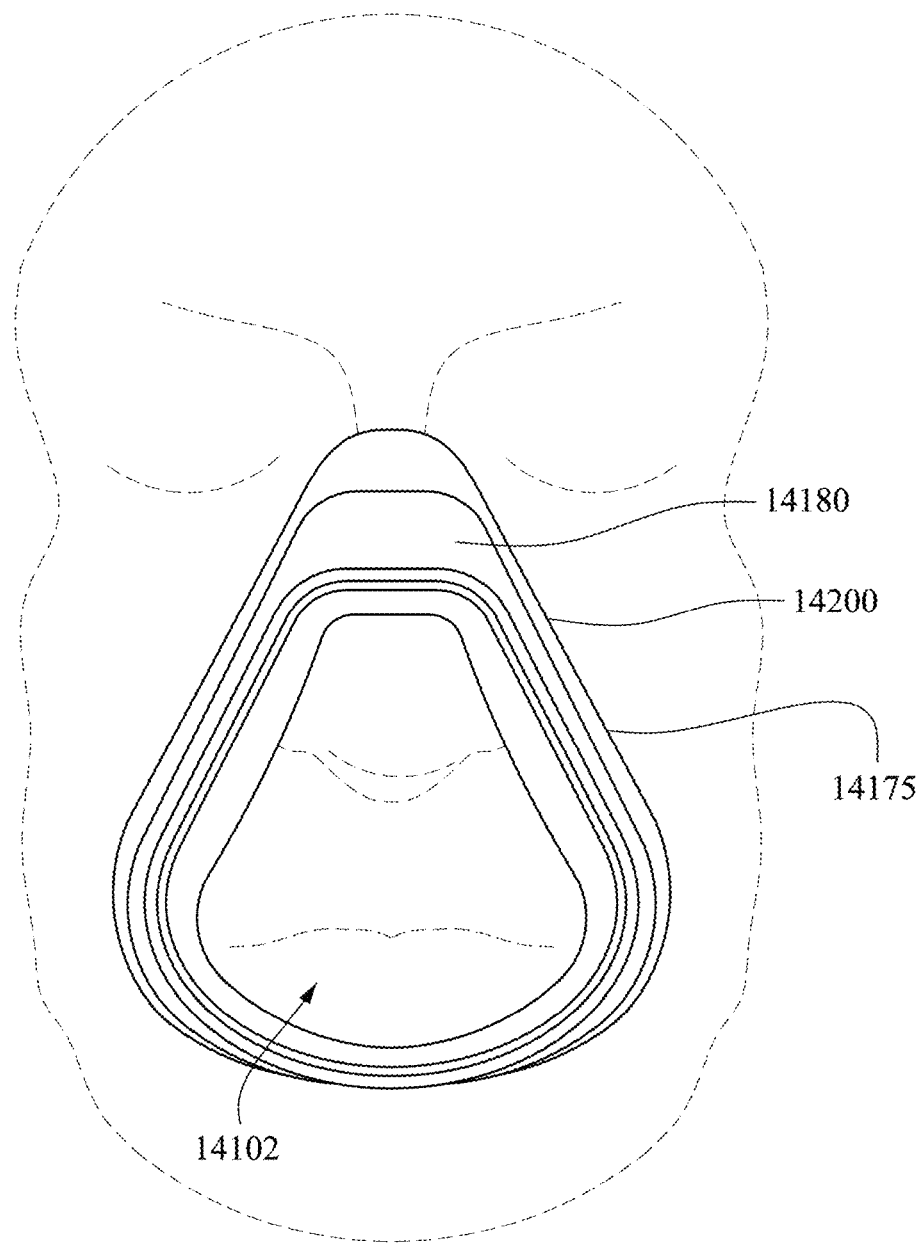

FIG. 37 is a front view of the patient interface shown in FIG. 34 shown on a patient's head according to an example of the present technology, the patient interface being shown with the anterior wall member disengaged and removed from the cushion assembly.

Figure 38:
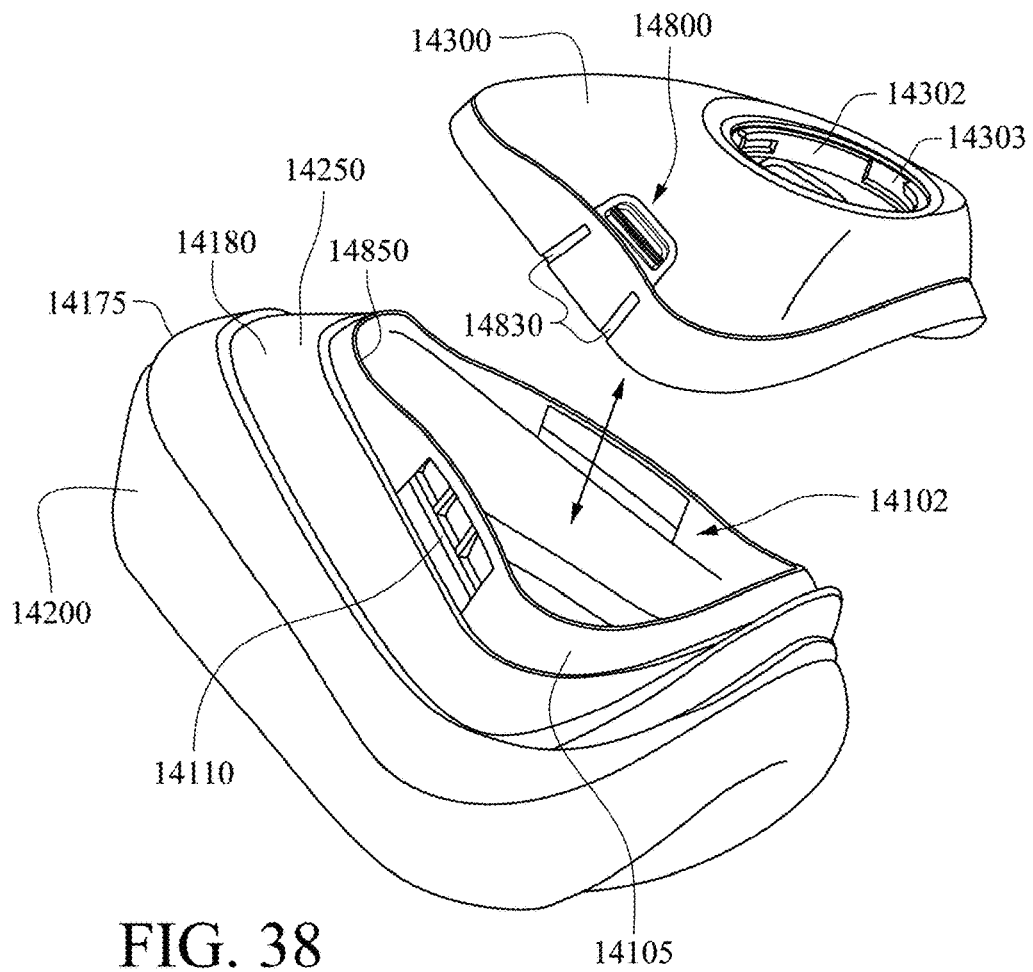

FIG. 38 is an exploded view of the patient interface shown in FIG. 34 showing assembly of the cushion assembly and the anterior wall member.

Figure 39:
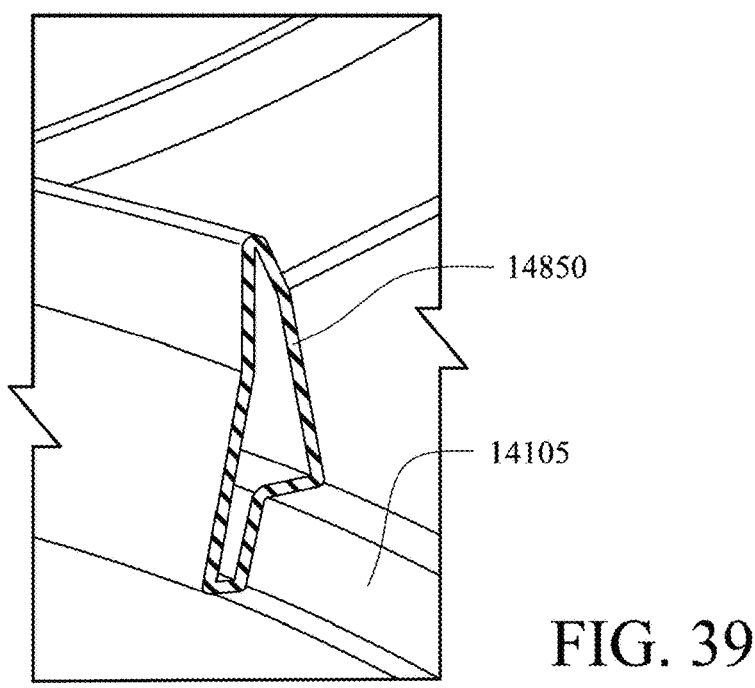

FIG. 39 is an enlarged cross-section view showing a lip seal of the cushion assembly according to an example of the present technology.

Figure 40:
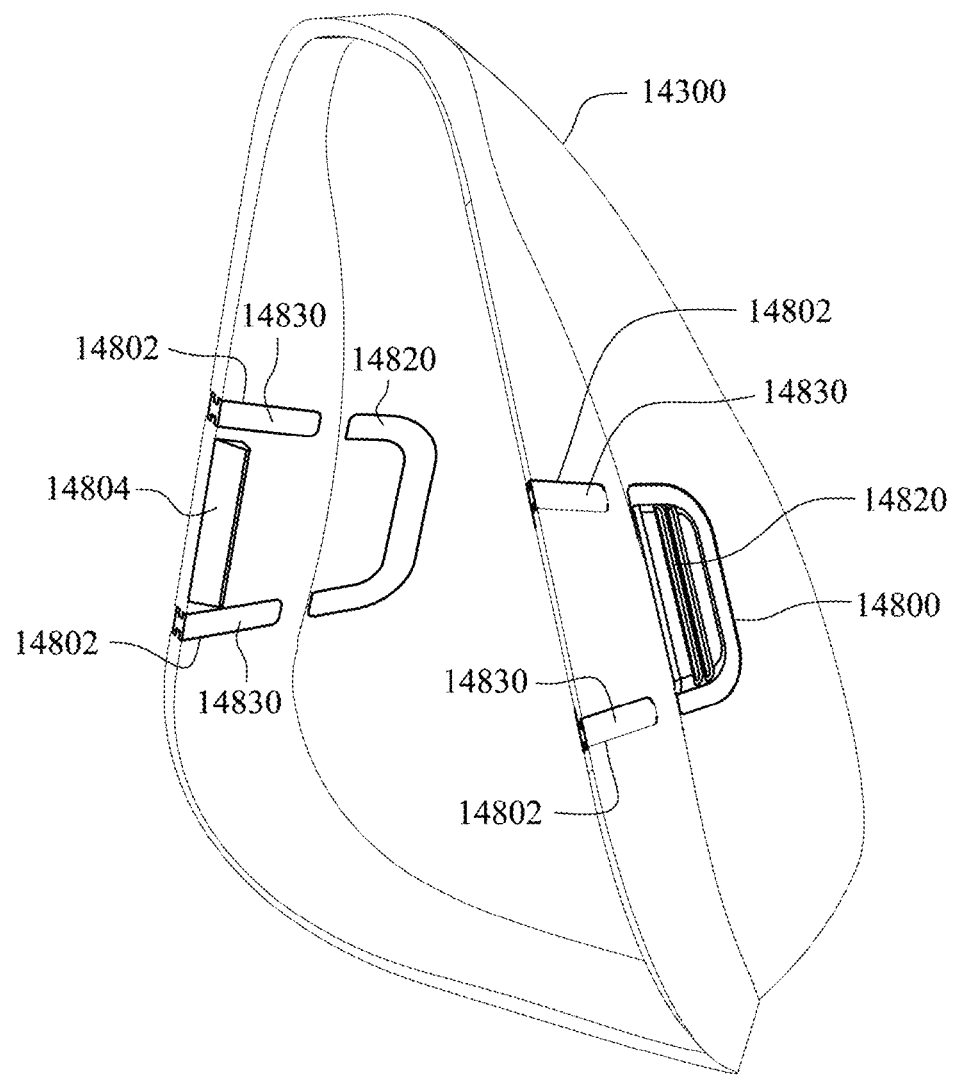

FIG. 40 is a perspective view of the anterior wall member of the patient interface shown in FIG. 34.

Figure 41:
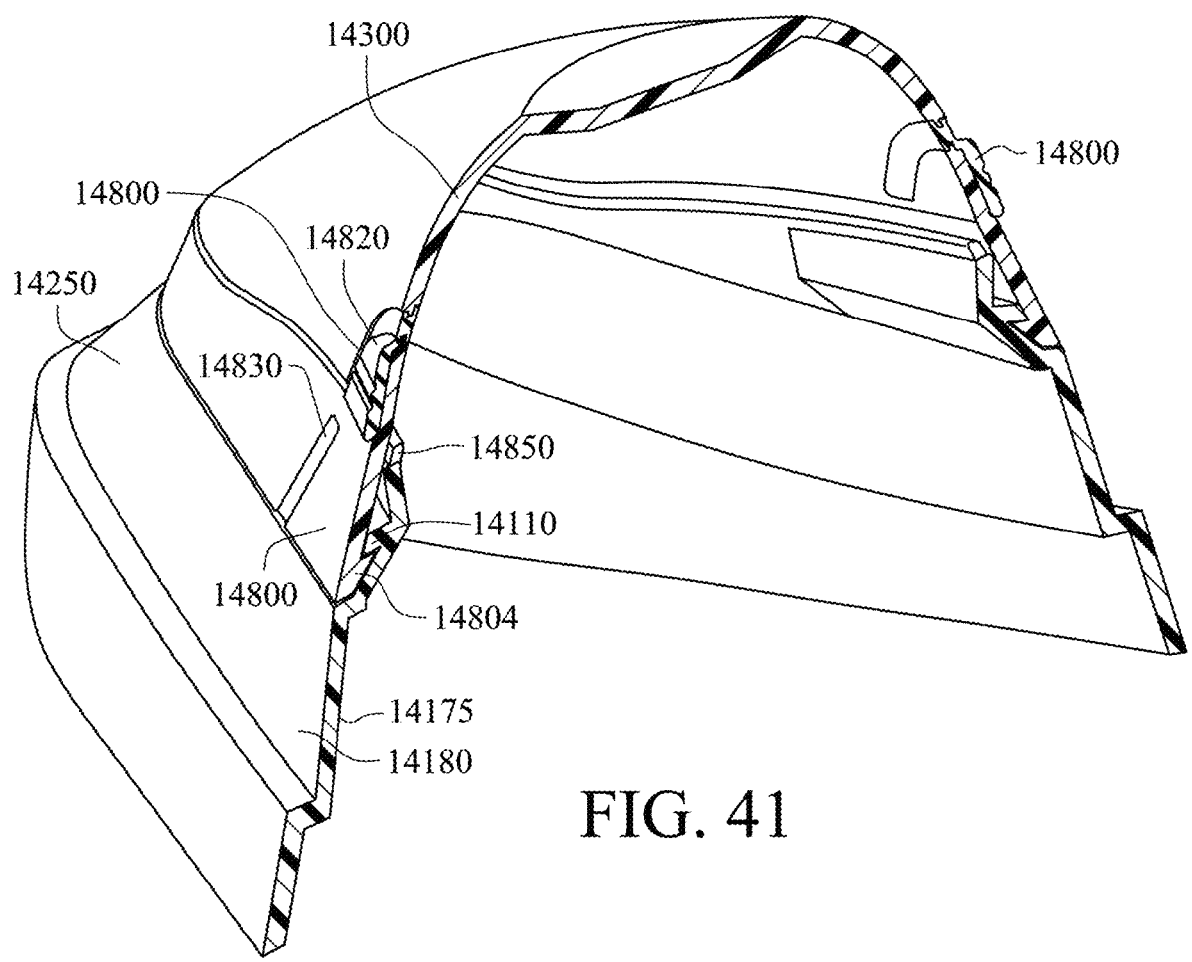

FIG. 41 is a cross-sectional view of the patient interface shown in FIG. 34 showing engagement between the cushion assembly and the anterior wall member.

Figure 42:
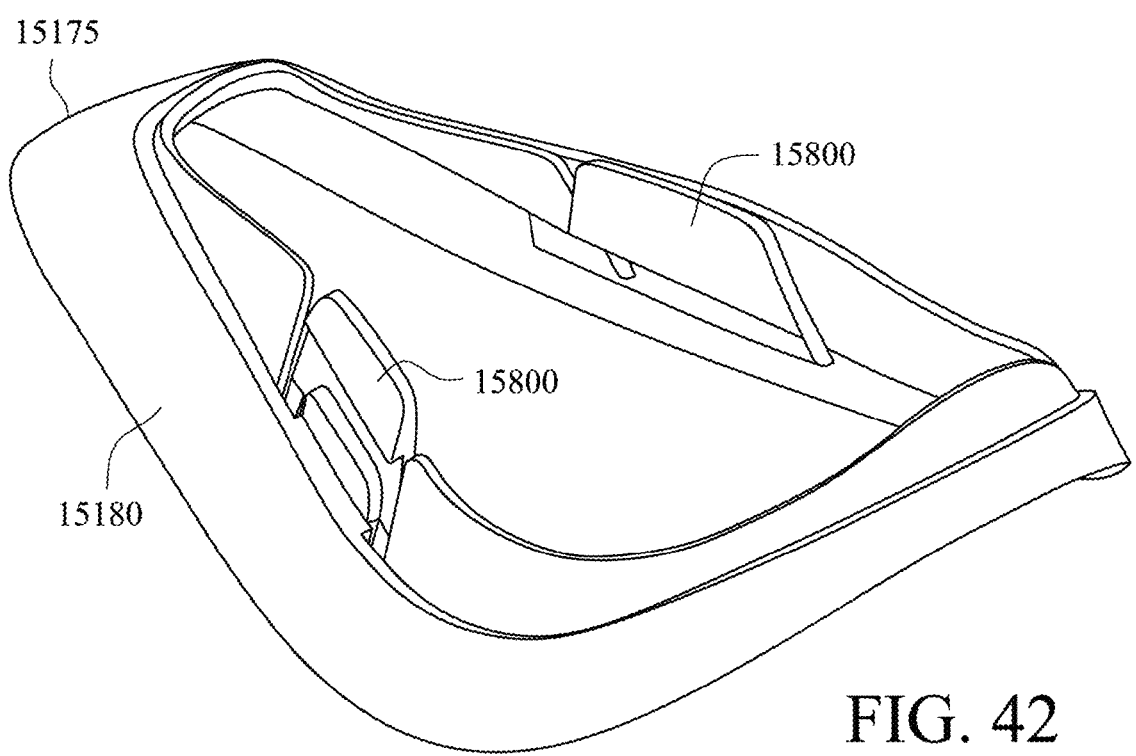

FIG. 42 is a perspective view of a cushion assembly according to another example of the present technology.

Figure 43:
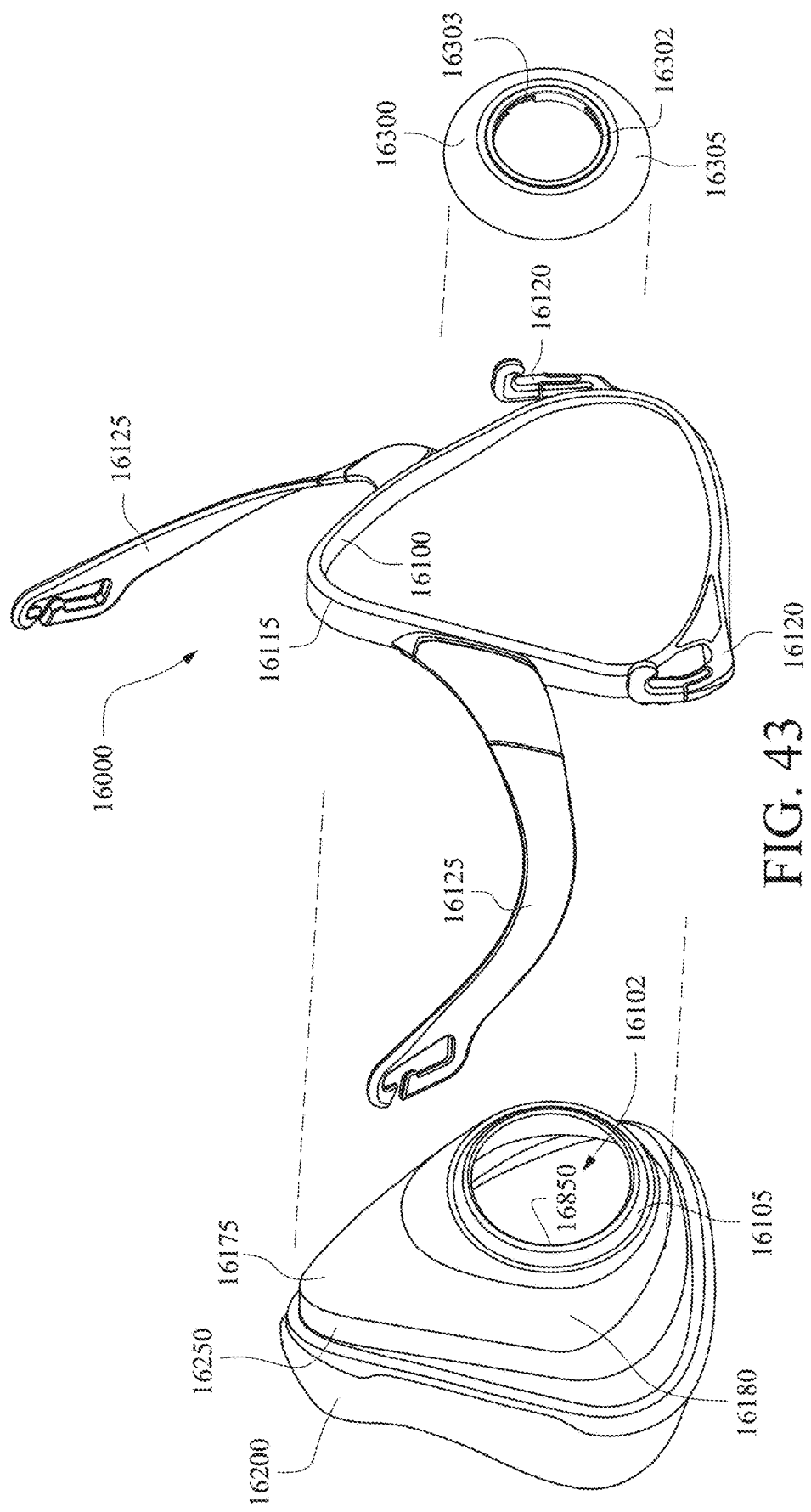

FIG. 43 is an exploded view of a patient interface according to another example of the present technology.

Figure 44:
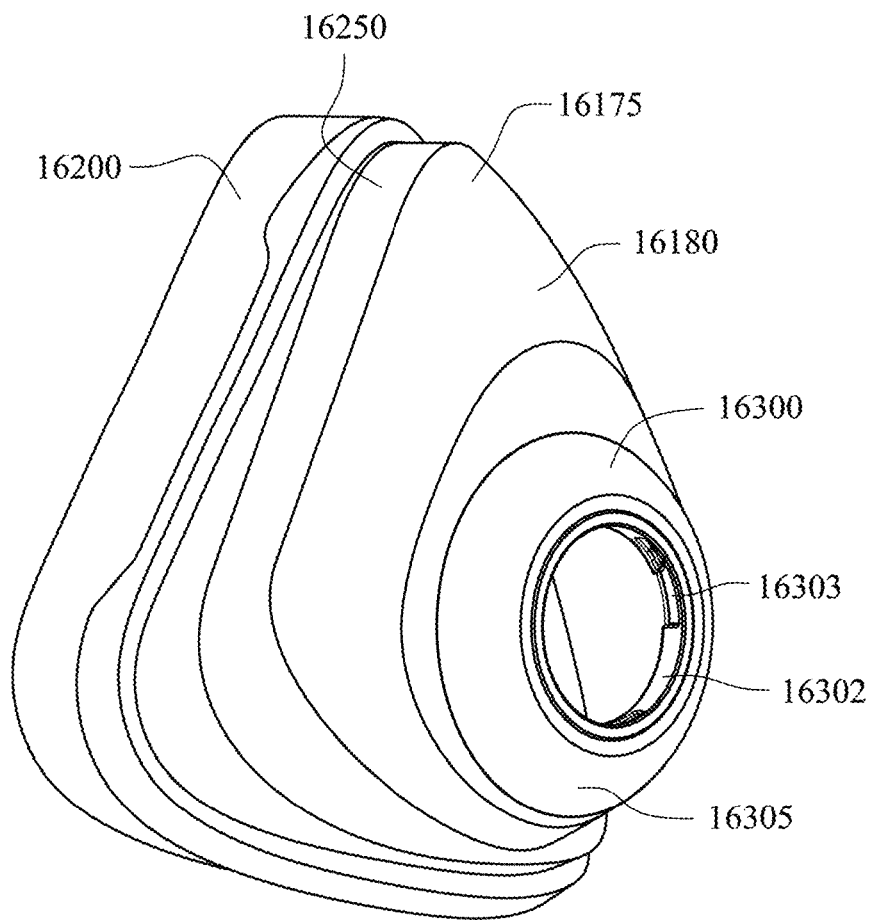

FIG. 44 is a perspective view of the patient interface shown in FIG. 43 showing the anterior wall member engaged with the cushion assembly.

Figure 45:
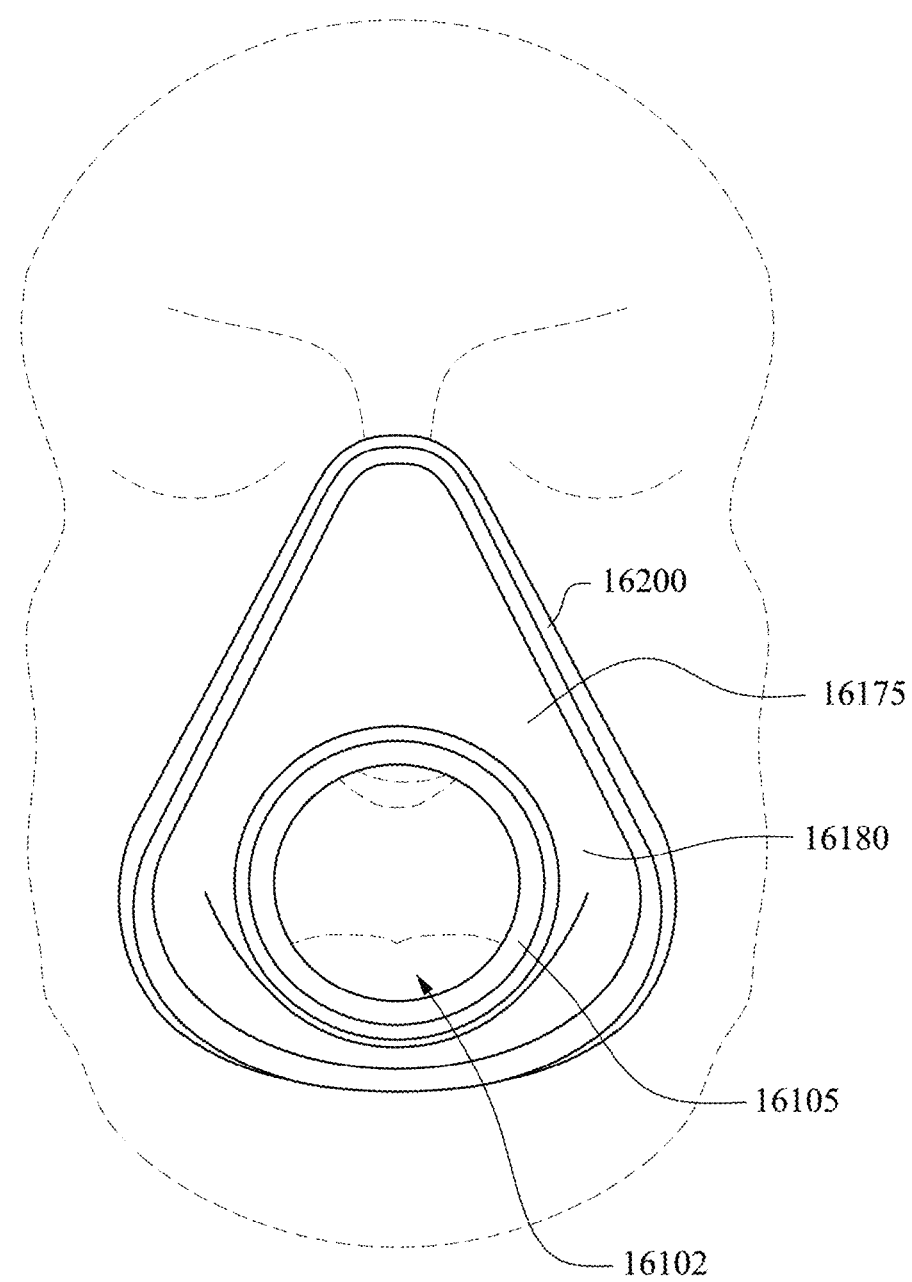

FIG. 45 is a front view of the patient interface shown in FIG. 43 shown on a patient's head according to an example of the present technology, the patient interface being shown with the anterior wall member disengaged and removed from the cushion assembly.

Figure 46:
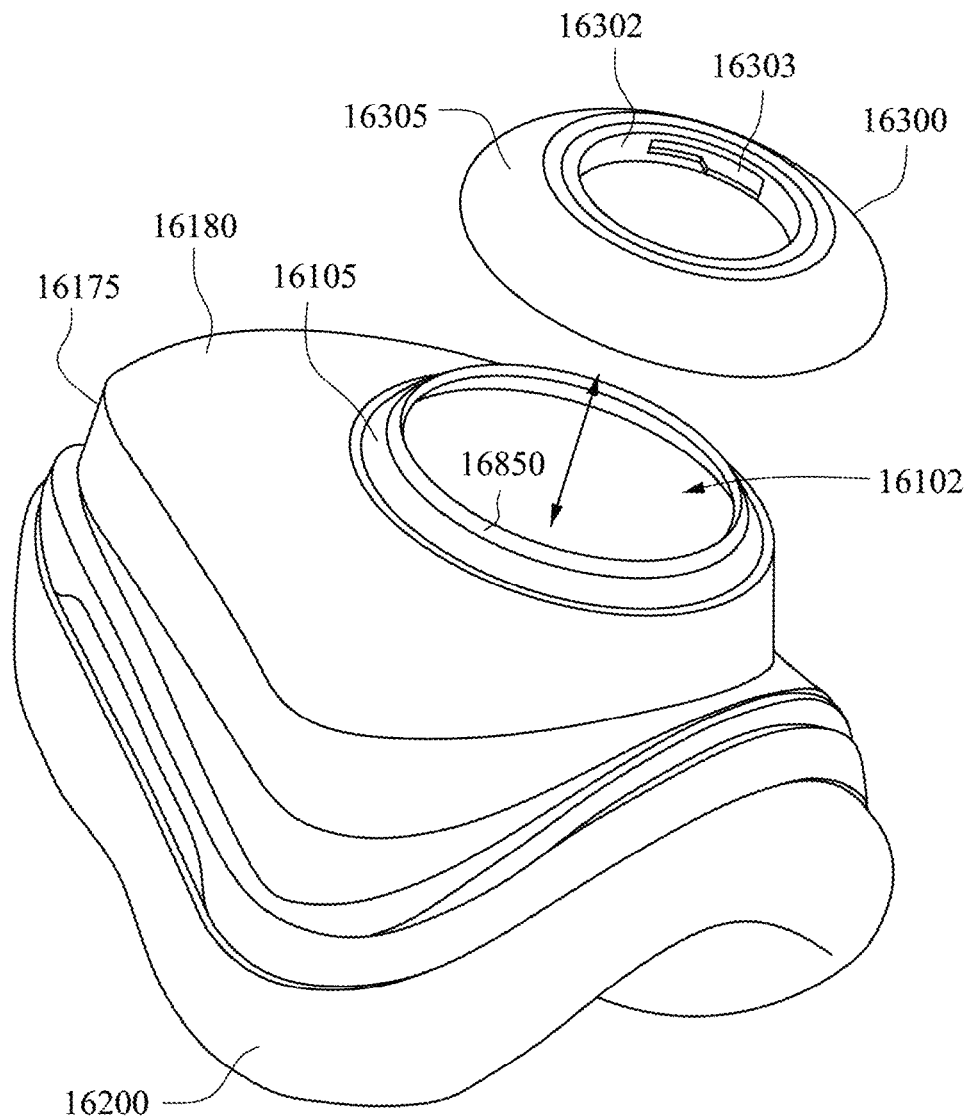

FIG. 46 is an exploded view of the patient interface shown in FIG. 43 showing assembly of the cushion assembly and the anterior wall member.

Figure 47:
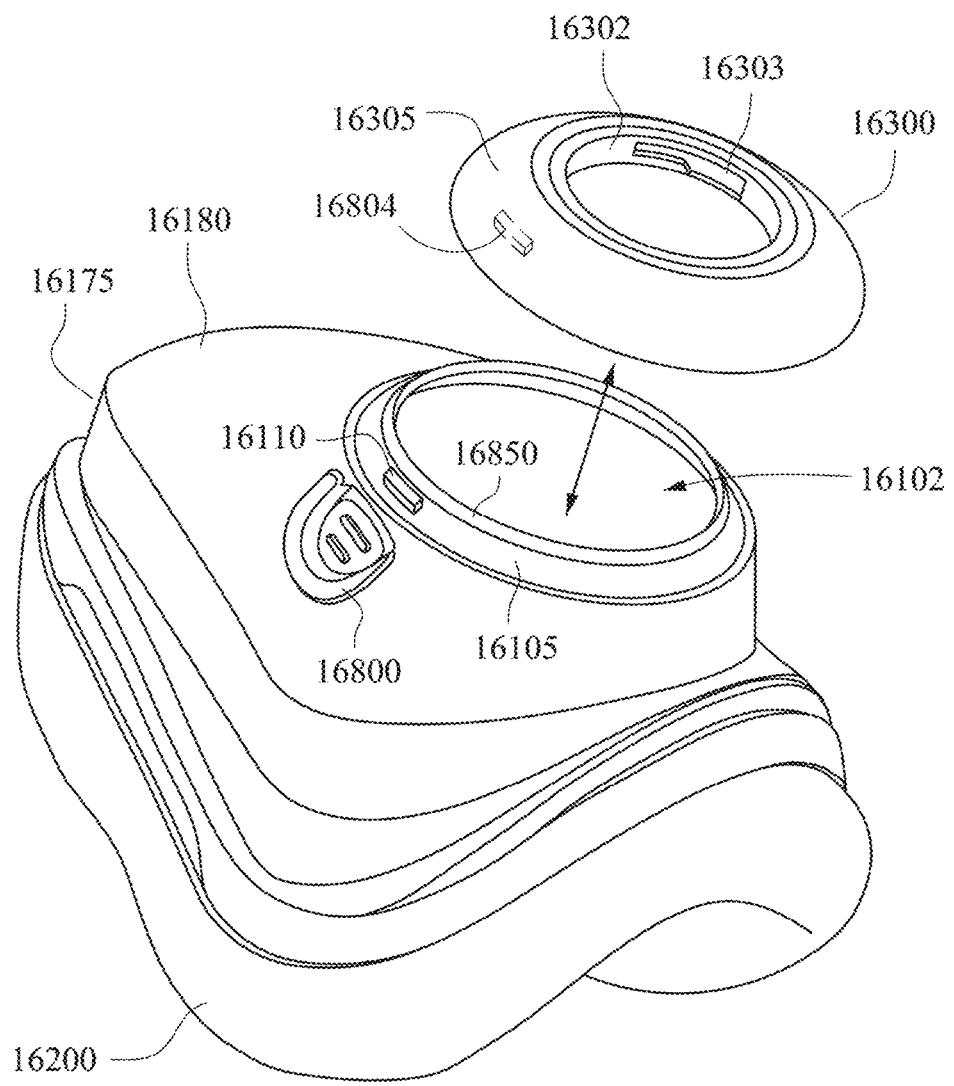

FIG. 47 is an exploded view of the patient interface shown in FIG. 43 showing a mechanical interlock between the cushion assembly and the anterior wall member according to an example of the present technology.

Figure 48:
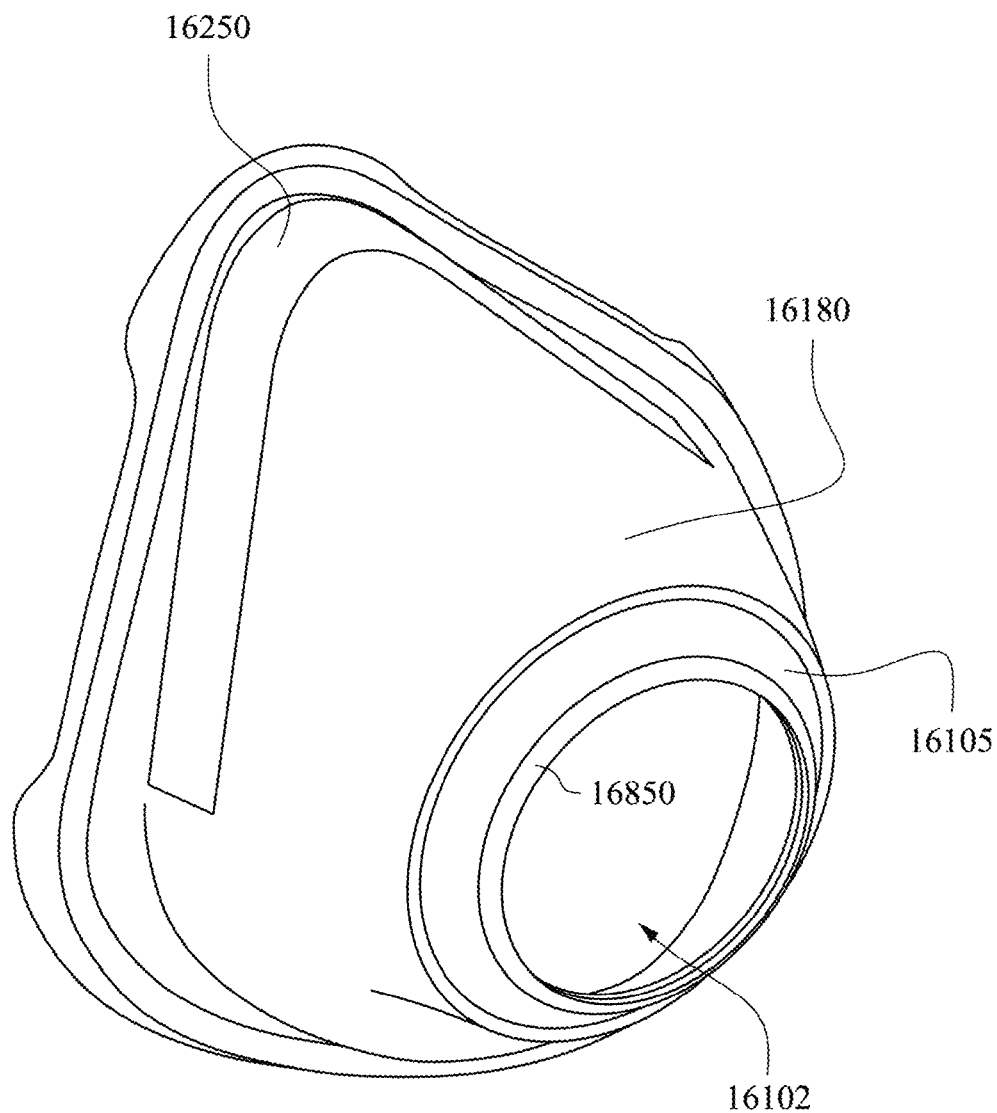

FIG. 48 is a perspective view showing a common frame interface for the main body of a cushion assembly according to an example of the present technology.

Figure 49C:
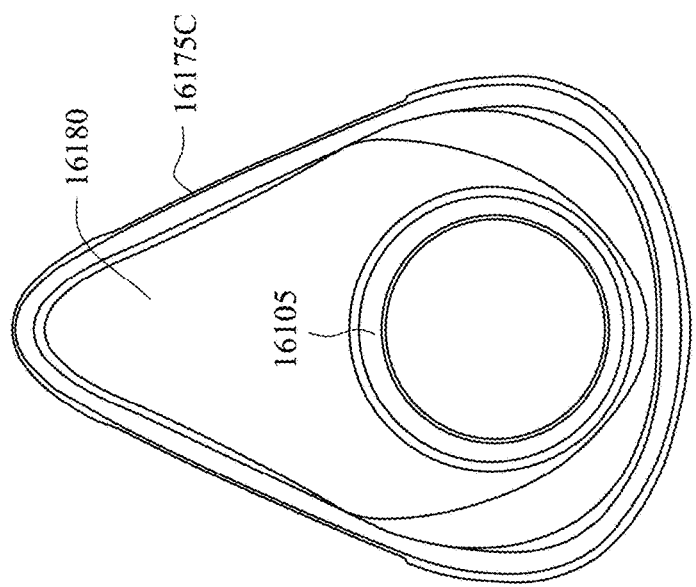
Figure 49B:
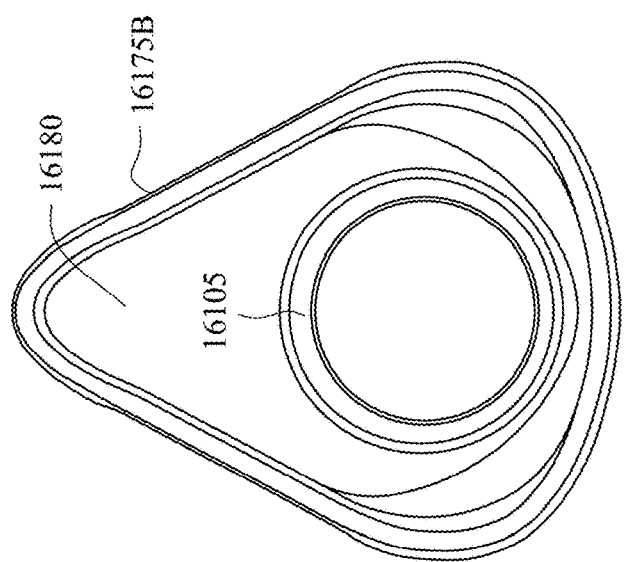
Figure 49A:
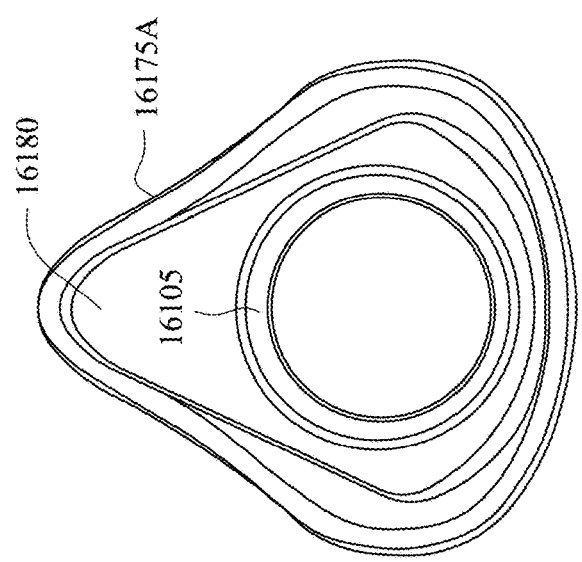

FIGS. 49A, 49B, and 49C are front views of small, medium, and large cushion assemblies according to an example of the present technology.

Figure 50C:
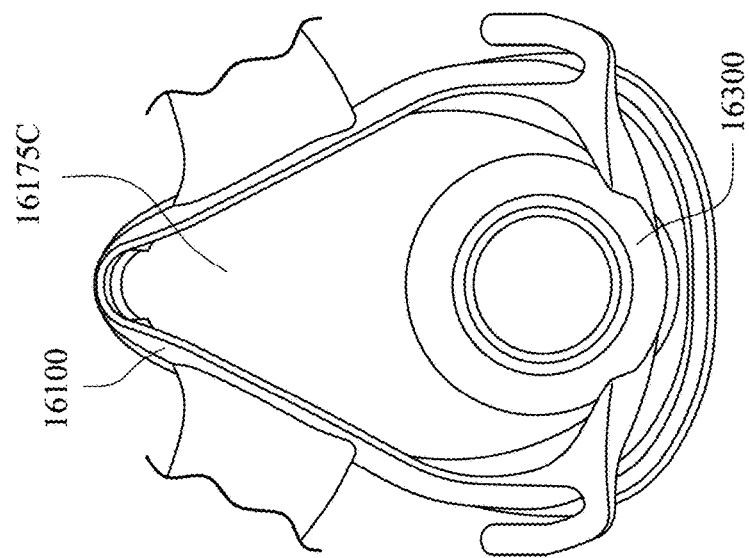
Figure 50B:
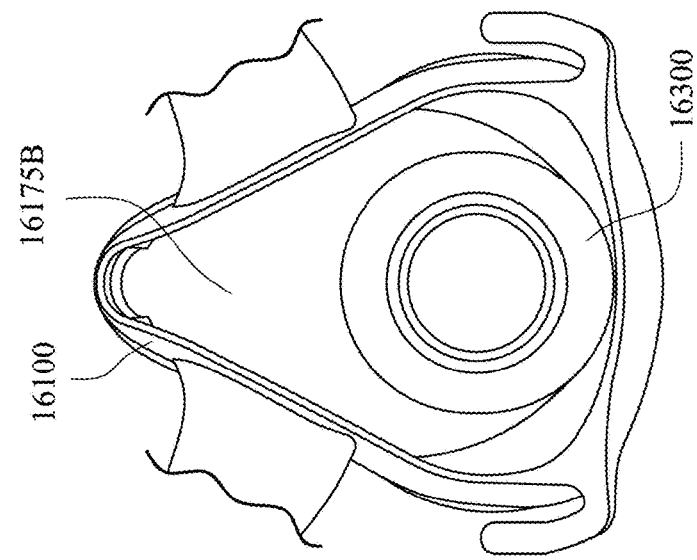
Figure 50A:
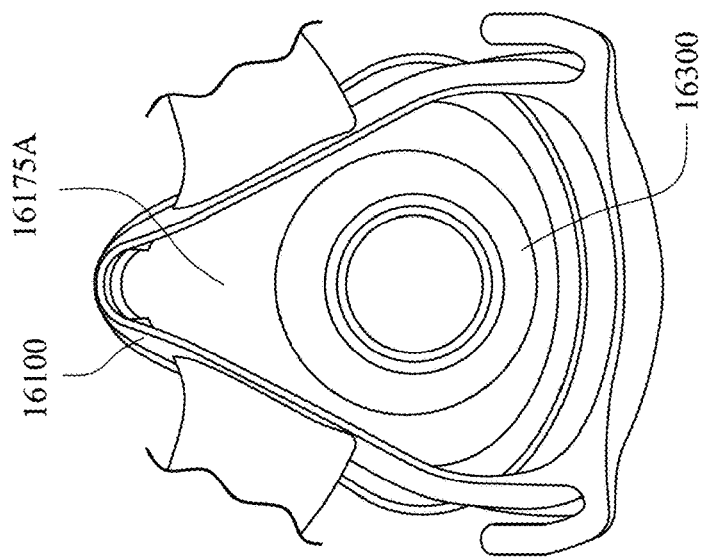

FIGS. 50A, 50B, and 50C are front views showing a common frame member and a common anterior wall member engaged with each of the small, medium, and large cushion assemblies of FIGS. 49A, 49B, and 49C according to an example of the present technology.

Figure 51:
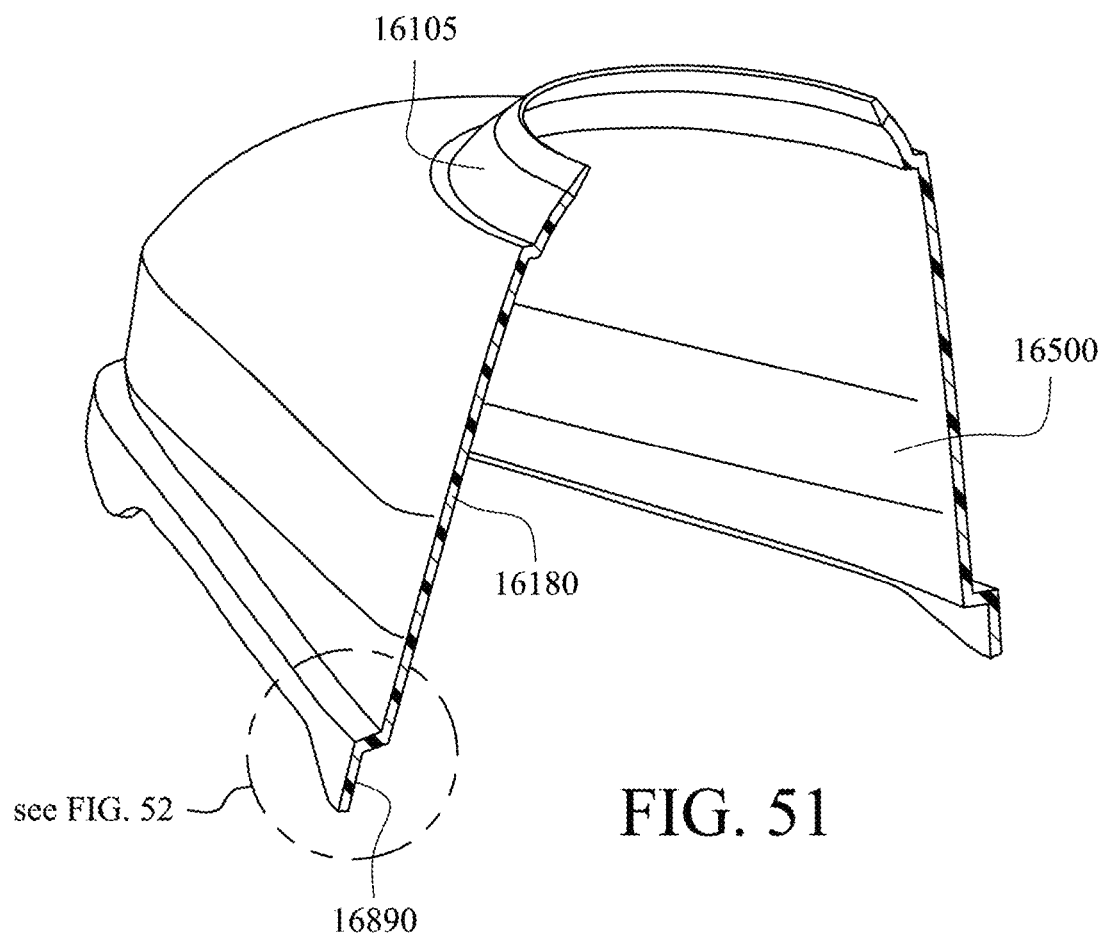
Figure 52:
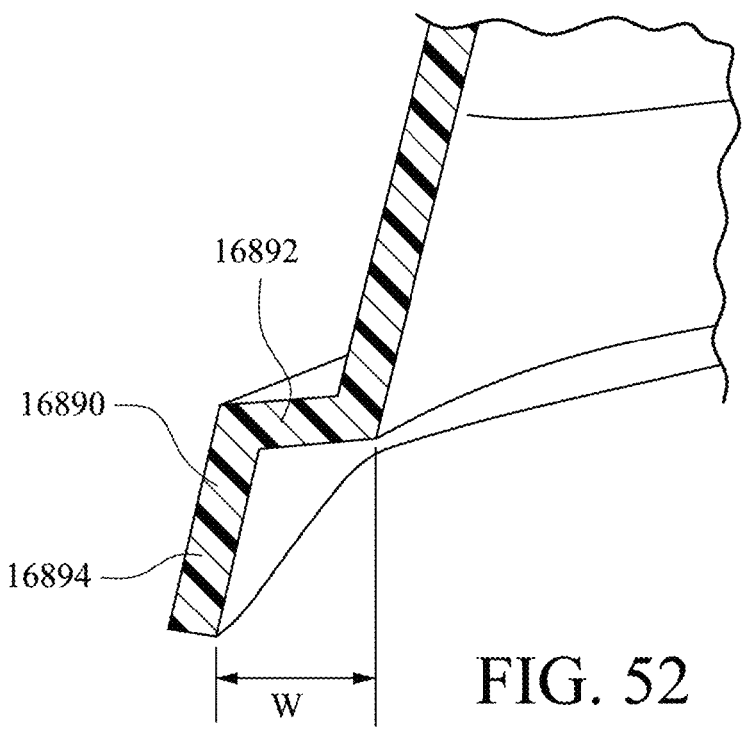
Figure 53:
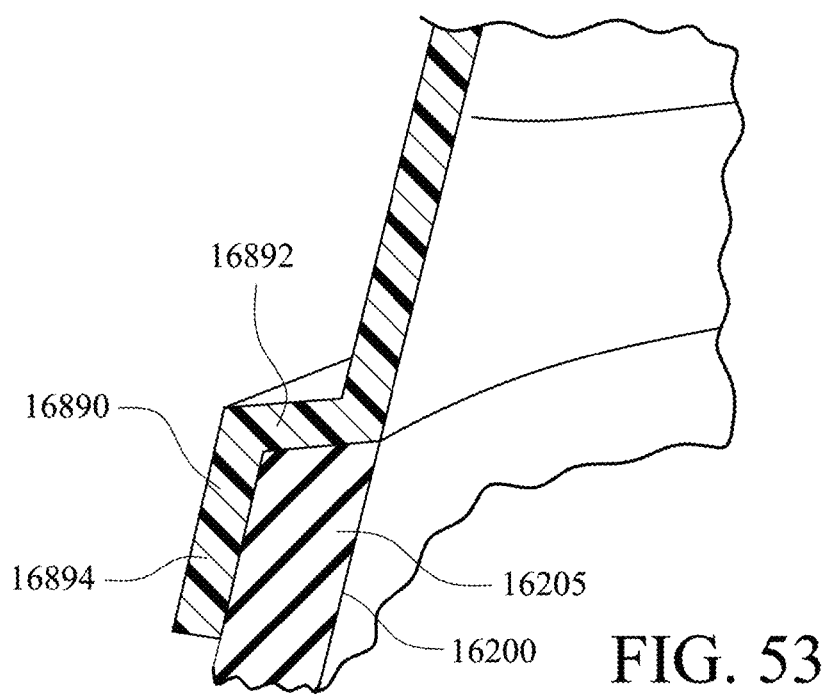

FIGS. 51, 52, and 53 are cross-sectional views showing a retaining structure of the cushion assembly according to an example of the present technology.

3 (D) DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to several examples which may share one or more common characteristics and features. It is to be understood that one or more features of any one example may be combinable with one or more features of another example or other examples. In addition, any single feature or combination of features in any of the examples may constitute a further example.

3.1 Treatment Systems

Figure 1A:
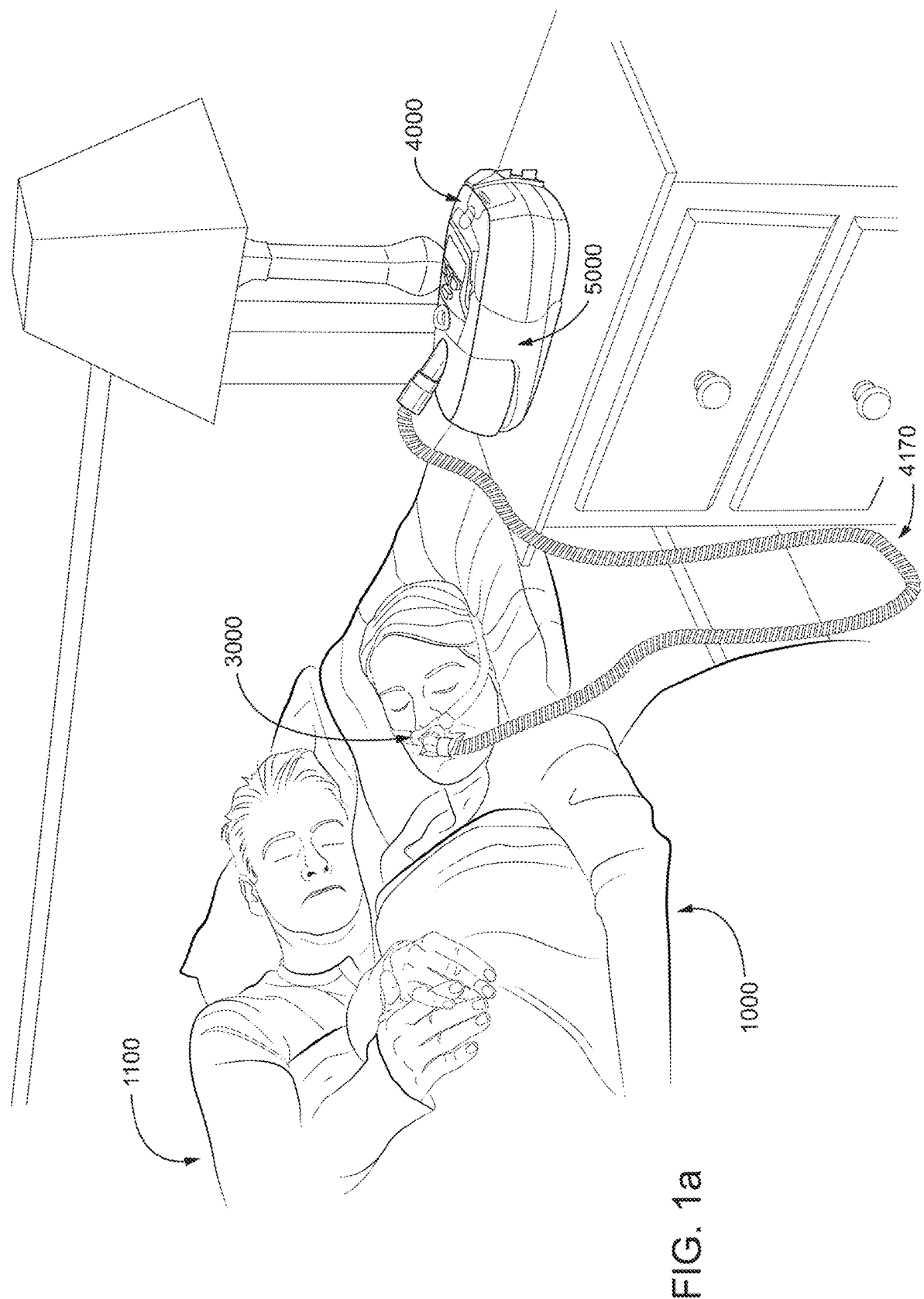
FIG. 1b shows a PAP device in use on a patient with a nasal mask.
FIG. 1c shows a PAP device in use on a patient with a full-face mask.
Figure 1B:
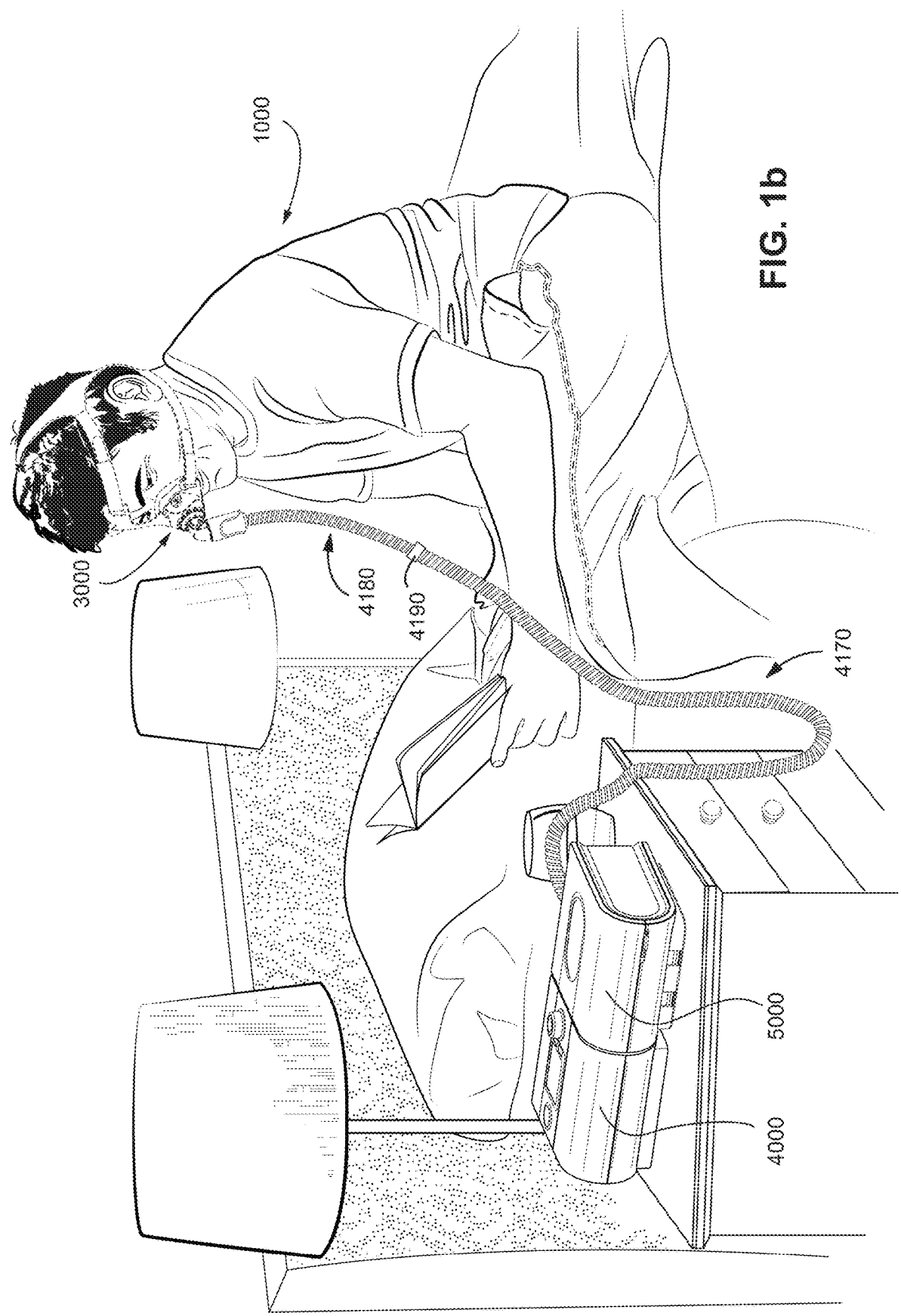
Figure 1C:

In one form, the present technology comprises an apparatus for treating a respiratory disorder, as shown in FIGS. 1a-1c. The apparatus may comprise a flow generator or blower 4000 for supplying pressurised respiratory gas, such as air, to the patient 1000 via a gas delivery tube 4170 leading to a patient interface 3000. The gas delivery tube 4170 may be connected to an additional gas delivery tube 4180 by a rotatable adapter 4190. A humidifier 5000 may also be provided to humidify the gas. A bed partner 1100 may also be present with the patient.

3.2 Therapy

In one form, the present technology comprises a method for treating a respiratory disorder comprising the step of applying positive pressure to the entrance of the airways of a patient 1000.

3.2.1 Nasal CPAP for OSA

In one form, the present technology comprises a method of treating Obstructive Sleep Apnea in a patient by applying nasal continuous positive airway pressure to the patient.

3.3 Patient Interface

Referring to FIGS. 4 to 16, a non-invasive patient interface 3000 in accordance with one aspect of the present technology comprises a frame member 3100, a cushion assembly 3175 including a seal-forming structure 3200, a removable anterior wall member 3300 (also referred to as a removable fascia) repeatedly engageable with and removably disengageable from the cushion assembly 3175, and a positioning and stabilising structure 3400. In use, one form of the seal-forming structure 3200 is arranged to surround an entrance to the airways of the patient 1000 so as to facilitate the supply of air at positive pressure to the airways. The seal-forming structure 3200 (e.g., constructed of silicone) may also be commonly referred to as a cushion.

In one form of the present technology, the frame member 3100, the cushion assembly 3175, and the anterior wall member 3300 are repeatedly and removably engageable with one another. In the illustrated example, the frame member 3100 and the cushion assembly 3175 are connected to one another, with the anterior wall member 3300 being repeatedly and removably engageable with the cushion assembly 3175 (e.g., see FIG. 11*b*). In this example, the anterior wall member 3300 is not directly connected to or engaged with the frame member 3100. In another example, the frame member and the cushion assembly may be connected to one another, with the anterior wall member being repeatedly and removably engageable with the frame member (e.g., see FIG. 23). In this example, the cushion assembly is connected to the anterior wall member via the frame member, i.e., the cushion assembly is not directly connected to the anterior wall member. In each form, the anterior wall member 3300 is always removably engageable with the cushion assembly 3175 or frame member 3100.

The frame member 3100 (e.g., constructed of a relatively hard plastic material such as polycarbonate) provides a connection between the cushion assembly 3175 and the positioning and stabilising structure 3400, e.g., either in a removable fashion or a more permanent fashion, to allow sealing forces to be transferred to the cushion assembly 3175 from the positioning and stabilising structure 3400.

The frame member 3100 may also be commonly referred to as a shroud, headgear connection structure, or chassis. In the illustrated example, the frame member 3100 engages with the cushion assembly 3175, and provides a 4-point connection to the positioning and stabilising structure 3400. The anterior wall member 3300 comprises a multi-hole vent 3700 surrounding connection port 3302. The connection port 3302 is connected to an elbow or swivel elbow 3600, which is connected to the gas delivery tube 4180 for fluid communication with a gas chamber or plenum chamber 3500 of the patient interface 3000.

In one form of the present technology, the cushion assembly 3175 includes a main body 3180 that is connected or otherwise provided to the seal-forming structure 3200. The main body 3180 may be permanently (e.g., co-molded, overmolded) or removably (e.g., mechanical interlock) connected to the seal-forming structure 3200. In an example, the seal-forming structure 3200 is constructed of a relatively flexible or pliable material (e.g., silicone) and the main body 3180 is constructed of a relatively rigid material (e.g., polycarbonate). In the illustrated example, the cushion assembly 3175 includes a void 3102 defined by an anterior facing surface 3104 of the main body 3180 of the cushion assembly 3175. When the anterior wall member 3300 and the cushion assembly 3175 are engaged, the anterior wall member 3300 (also referred to as the fascia) has a predetermined surface area to pneumatically seal the void 3102 of the cushion assembly 3175 and form the gas chamber or plenum chamber 3500 (e.g., see FIG. 20*a*). The predetermined surface area of the anterior wall member 3300 may be at least 50% of the total surface area of the superficial anterior wall of the cushion assembly 3175. In an example, the predetermined surface area of the anterior wall member 3300 may be greater than 381 mm$^2$. The void 3102 extends through the main body 3180 and the opening of the seal-forming structure 3200 to expose the patient's mouth and/or nose and/or upper lip.

As best shown in FIGS. 7-9 and 21, the void 3102 of the cushion assembly 3175 is sized such that the patient's nose and/or mouth is substantially exposed to ambient air and visible to the bed partner 1100 when the anterior wall member 3300 is disengaged from the cushion assembly 3175 thereby improving breathing comfort of the patient. Advantageously, this exposure may allow the bed partner 1100 to see the patient's lips moving when speaking which is more humanizing. An ideal breathing comfort is ambient air external of the patient interface 3000 which is considered natural breathing. Breathing comfort considers relative humidity, quantity of carbon dioxide, air flow impedance and air temperature. When the patient interface 3000 is donned by the patient and the anterior wall member 3300 is disengaged from the cushion assembly 3175 without therapy activated, breathing comfort for the patient should be similar or substantially the same as breathing the ambient air without the patient interface 3000 donned.

As shown in FIGS. 21 and 22, the void 3102 is sized to be sufficiently larger than a conventional connection port 302 for connection to a gas delivery tube. A conventional connection port 302 typically has a 22 mm diameter. That is, the void 3102 when the anterior wall member 3300 is removed provides a larger mask opening than conventional masks when the gas delivery tube is removed from the conventional connection port 302. For example, the void 3102 provides a height H (FIG. 21) that is sufficiently larger than a height or diameter h (22 mm) of the conventional connection port 302 (FIG. 22), which larger height H allows the patient's nose and/or mouth to be substantially exposed when the anterior wall member 3300 is disengaged from the cushion assembly 3175. In an example, the height or diameter H is greater than 22 mm and/or the void 3102 provides an area greater than 381 mm$^2$.

The sufficiently larger mask opening provided by the void 3102 improves breathing comfort of the patient (e.g., less claustrophobic, less air flow impedance), provides a less bulky/obtrusive mask (very low profile), allows visual inspection, better avoids condensation build-up (fogging), and/or assists with patient acclimatization of the patient interface 3000.

The patient interface 3000 is structured to reduce bulk along the sagittal plane, i.e., reduce depth of the patient interface or protrusion of the patient interface from the patient's face in the anterior-posterior direction. Also, the patient interface 3000 is structured to reduce the facial footprint (the superficial surface area) in the coronal plane, i.e., the surface area projected by the patient interface 3000 on the patient's face. The reduction in size in all three dimensions when the anterior wall member 3300 is removed from the cushion assembly 3175 reduces overall weight and perceived size and weight by the patient.

In an example, as shown in FIG. 20b, the patient interface 3000 may be structured to house an optional and replaceable heat and moisture exchanger (HME/HMX) cartridge 3750 to provide sufficient heat and humidity to the patient during therapy. For example, the HME/HMX cartridge 3750 may be integrated or otherwise received and supported in the anterior wall member 3300. In an example, the HME/HMX cartridge is a detachable HME/HMX cartridge positioned within the gas chamber and having a length greater than a diameter of a conventional connection port, i.e., length greater than 22 mm. The anterior wall member 3300 may have a length at least the same as the length of the HME/HMX cartridge to allow the HME/HMX cartridge to be detached via the void 3102 defined by the anterior surface of the cushion assembly 3175. Such arrangement allows a HME/HMX cartridge having a length greater than 22 mm to be removed or inserted via the front of the patient interface.

Engagement between Cushion Assembly and Anterior Wall Member

In one form of the present technology, at least a peripheral portion 3305 of the anterior wall member 3300 is repeatedly engageable with and disengageable from at least a peripheral portion 3105 of the main body 3180 of the cushion assembly 3175. In an example, the peripheral portion 3305 of the anterior wall member 3300 and the peripheral portion 3105 of the cushion assembly 3175 are rigid such that engagement between the peripheral portion 3305 of the anterior wall member 3300 and the peripheral portion 3105 of the cushion assembly 3175 provides a hard-to-hard connection and is not caused by material deformation of the cushion assembly 3175 and/or the anterior wall member 3300.

In an example, the perimeter and/or shape of the anterior wall member 3300 is predetermined to facilitate alignment of the anterior wall member 3300 to the cushion assembly 3175 for mechanical/structural engagement. For example, the shape of the anterior wall member 3300 may be symmetrical in at least one axis to minimise misalignment of the anterior wall member 3300 to the cushion assembly 3175 for engagement.

In an example, when the cushion assembly 3175 and the anterior wall member 3300 are engaged, accidental disengagement caused by tube drag forces is prevented due to the shape, geometry and perimeter of the mating surfaces of the cushion assembly 3175 and the anterior wall member 3300. That is, the cushion assembly 3175 and the anterior wall member 3300 are structured to maintain engagement during use and prevent any unintentional or partial disassembly during use.

Magnetic Engagement

In one form of the present technology, the anterior wall member 3300 is magnetically engageable with the cushion assembly 3175. For example, the peripheral portion 3305 of the anterior wall member 3300 and the peripheral portion 3105 of the main body 3180 of the cushion assembly 3175 may be magnetically engageable.

As shown in FIGS. 11a and 11b, the anterior facing surface 3104 (also referred to as a mounting surface) provided along the exterior or outwardly facing surface of the peripheral portion 3105 of the cushion assembly 3175 includes at least one magnet 3110, and the posterior facing surface 3303 provided along the interior or inwardly facing surface of the peripheral portion 3305 of the anterior wall member 3300 includes at least one magnet 3310.

In the example shown in FIGS. 4 to 16, the cushion assembly 3175 and the anterior wall member 3300 each include three magnets, e.g., one magnet 3110, 3310 provided along an apex of the respective peripheral portion 3105, 3305 and the remaining two magnets 3110, 3310 provided on opposing, lower sides of the respective peripheral portion 3105, 3305. However, it should be appreciated that more or less magnets may be provided, and the magnets 3110, 3310 may be positioned in other suitable arrangements and positions along the peripheral portions 3105, 3305. The magnets 3110, 330 depicted have a circular cross-section, however, any shape or size may be suitable.

In an example, the at least one magnet 3110, 3310 provided to the cushion assembly 3175 and the anterior wall member 3300 may be a permanent magnet or an electromagnet.

The magnetic attraction between the magnets 3110, 3310 of the cushion assembly 3175 and the anterior wall member 3300 guides and aligns the anterior wall member 3300 to the cushion assembly 3175 during engagement at least prior to surface contact between the cushion assembly 3175 and the anterior wall member 3300 when they are in close physical proximity to each other. Also, the magnetic attraction between the anterior wall member 3300 and the cushion assembly 3175 may provide the primary engagement force to maintain engagement of the anterior wall member 3300 to the cushion assembly 3175. In an example, the retention force (from the magnets) between the anterior wall member 3300 and the cushion assembly 3175 is less than the retention force (from headgear) to maintain the cushion assembly 3175 in sealing engagement with the patient's face.

The easy magnetic connection/disconnection between the cushion assembly 3175 and the anterior wall member 3300 facilitates use in the dark using macro movement (e.g., useful for bathroom break during the night), provides easy access to the patient for hospital/lab use cases by providing a quick release, and provides a greater sense of control over therapy for the patient (quick release, e.g., without pressing any buttons or rotating a bayonet coupling). Macro movement is contrasted with fine motor skills.

Flow Generator Activation/Deactivation

In one form of the present technology, engagement of the anterior wall member 3300 with the cushion assembly 3175 automatically activates a flow generator 4000 to supply pressurised respiratory gas to the patient interface 3000 via a gas delivery tube 4180 connected to the elbow 3600, and disengagement of the anterior wall member 3300 from the cushion assembly 3175 automatically deactivates the flow generator 4000 to cease the supply of pressurised respiratory gas to the patient interface 3000. In another example, engagement of the anterior wall member 3300 with the cushion assembly 3175 automatically actuates a valve to activate the supply of pressurised respiratory gas to the patient interface 3000.

For example, magnetic engagement of the peripheral portion 3305 of the anterior wall member 3300 to the peripheral portion 3105 of the cushion assembly 3175 causes the flow generator 4000 to supply pressurised respiratory gas to the patient interface 3000 via the gas delivery tube, and when the anterior wall member 3300 and cushion assembly 3175 are disengaged, the flow generator ceases the supply of pressurised respiratory gas to the patient interface 3000.

An electrical activate/deactivate signal may be sent from the patient interface 3000 to the flow generator 4000 in accordance with methods and apparatuses disclosed in U.S. Pat. No. 6,240,921, which is herein incorporated by reference in its entirety.

If the gas delivery tube 4170 is a heated tube comprising at least one wire, the at least one wire may transmit an electrical activate/deactivate signal from the patient interface 3000 to the flow generator 4000 to activate or cease the supply of pressurised respiratory gas to the patient interface 3000.

Alternatively, there may be a wireless transmitter located at the patient interface 3000 which may wirelessly transmit an electrical activate/deactivate signal to a wireless receiver located at the flow generator 4000 to activate or cease the supply of pressurised respiratory gas to the patient interface 3000.

The activate/deactivate signal may be sent upon detection of a magnetic field using a reed sensor, Hall Effect sensor or anisotropic magnetoresistance (AMR) sensor.

Alternative Engagement Examples Between Anterior Wall Member and Cushion Assembly In an alternative example, the peripheral portion 3305 of the anterior wall member 3300 and the peripheral portion 3105 of the cushion assembly 3175 may be engageable using an adhesive or a hook-and-loop fastener.

In an alternative example, the peripheral portion 3305 of the anterior wall member 3300 and the peripheral portion 3105 of the cushion assembly 3175 may be engageable using a mechanical interlock, e.g., snap-fit connection, barb, hinge, etc.

It should be appreciated that these alternative engagement examples may be used in lieu of or in combination with magnetic engagement. In examples without magnets, some advantages include lower cost and less manufacturing complexity associated with embedding magnets into plastic material.

For example, FIGS. 34 to 41 illustrate a patient interface 14000 according to an example of the present technology. The patient interface 14000 includes a frame member 14100, a cushion assembly 14175 including a seal-forming structure 14200, and an anterior wall member 14300 (shown without an elbow) repeatedly engageable with and removably disengageable from the cushion assembly 14175 via a mechanical interlock, e.g., snap-fit connection.

In this example, the frame member 14100 is similar to that shown in FIGS. 31-33 and includes an annular or ring style side wall 14115 with upper headgear connectors 14152 and lower headgear connectors 14120 adapted to connect to upper and lower side straps of the positioning and stabilizing structure 3400. The annular side wall 14115 of the frame member 14100 may be releasably connected or interlocked with a retaining portion or frame interface 14250 of the cushion assembly 14175 in any suitable manner.

The anterior wall member 14300 includes connection port 14302 adapted to be connected to an elbow or swivel elbow which is connected to the gas delivery tube 4180. In the illustrated example, the connection port 14302 includes grooves 14303 structured to allow a bayonet style attachment to the elbow. However, it should be appreciated that the elbow may be releasably or permanently connected to the connection port 14302 in other suitable manners.

As illustrated, each side of the anterior wall member 14300 includes a cantilevered push button 14800 and grooves 14802 along sides of the button 14800 that allow the button 14800 to flex with respect to the anterior wall member 14300. Each button 14800 includes a tab or catch 14804 (e.g., see FIG. 40) along an interior or inwardly facing surface of the anterior wall member 14300 that is adapted to engage the cushion assembly 14175 with a snap fit to releasably secure the anterior wall member 14300 to the cushion assembly 14175.

In the illustrated example, as best shown in FIGS. 40 and 41, a raised portion 14820 of the button and webbing 14830 within the grooves 14802 along sides of the button is constructed of a soft, tactile material, e.g., TPE. The raised portion 14820 provides a soft tactile feel for ease of use and grip, and the webbing 14830 provides seal, soft tactile feel, and spring (clip return) force. In an example, the raised portion 14820 and webbing 14830 are overmolded to the anterior wall member 14300.

Each side of a peripheral portion 14105 of the cushion assembly 14175 includes a tab or undercut 14110 structured to interlock with a respective tab or catch 14804 of the anterior wall member 14300 to releasably retain the anterior wall member 14300 to the cushion assembly 14175.

In an example, the elbow connected to the connection port 14302 of the anterior wall member 14300 may be used to grip or handle the anterior wall member 14300 to facilitate engagement/disengagement with the cushion assembly 14175.

In an alternative example, as shown in FIG. 42, the cantilevered push button 15800 may be provided to the main body 15180 of the cushion assembly 15175, which is structured to interlock with a respective tab or catch on the anterior wall member.

As shown in FIGS. 38 and 39, a lip seal 14850 (e.g., constructed of silicone) is provided along the edge of the peripheral portion 14105 defining the void 14102 of the cushion assembly 14175. As illustrated, the lip seal 14850 includes a hollow construction with side walls that cooperate to define an interior chamber (e.g., see FIG. 39), however other suitable sealing configurations are possible. In an example, the lip seal 14850 is overmolded to the main body 14180 of the cushion assembly 14175, e.g., during overmolding of the seal-forming structure 14200 to the main body 14180. The lip seal 14850 provides a compression and pressure assisted/pressure actuated seal between the cushion assembly 14175 and the anterior wall member 14300 when engaged with one another. In other words, when air pressure within the plenum chamber 3500 increases, the lip seal 14850 is urged against the anterior wall member 14300 with greater force.

When the anterior wall member 14300 and the cushion assembly 14175 are engaged, the anterior wall member 14300 seals the void 14102 of the cushion assembly 14175 and forms the gas chamber or plenum chamber. The anterior wall member 14300 is structured to align, seal, and interlock with main body 14180 of the cushion assembly 14175 (and not the frame member 14100) to allow better tolerance control and avoid headgear strap tension forces acting on the anterior wall member 14300. When the anterior wall member 14300 is disengaged from the cushion assembly 14175, e.g., see FIG. 37, the void 14102 of the cushion assembly 14175 is sized such that the patient's nose and/or mouth is substantially exposed, e.g., to improve patient breathing comfort, improve patient communication with bed partner, allow patient to drink/eat/medicate, allow clinician to view seal (from the interior of the patient interface prior to commencement of therapy, e.g. the fit of the static seal), and/or facilitate patient/clinician acclimatization to CPAP treatment.

In an example, the frame member 14100 and the anterior wall member 14300 may be provided in one size, which may be selectively engageable with multiple sizes of cushion assemblies 14175, e.g., small, medium, and large size cushion assemblies. In an example, regardless of size, the patient interface provides similar locations for the upper headgear connectors 14152 (e.g., based on headgear vectors and clearance with the patient's eyes) and the connection port 14302 for the elbow (e.g., to optimize gas washout). Also, anthropometrics (e.g., clearance with the patient's face, nose and/or mouth) and manufacturability (e.g., line of draw) may be similar across cushion sizes. For example, the axis of the connection port 14302 relative to the line of draw (e.g., about 10°) may be similar across cushion sizes. This may prevent the patient's nose coming into physical contact with the frame member 14100 and the anterior wall member 14300 when the patient interface is donned.

FIGS. 43 to 52 illustrate a patient interface 16000 according to another example of the present technology. The patient interface 16000 includes a frame member 16100, a cushion assembly 16175 including a seal-forming structure 16200, and a ring-shaped or disk-shaped anterior wall member 16300 (shown without an elbow) repeatedly engageable with and removably disengageable from the cushion assembly 16175.

In this example, the frame member 16100 is similar to that shown in FIGS. 31-36 and includes an annular or ring style side wall 16115 with upper headgear connectors 16152 and lower headgear connectors 16120 adapted to connect to upper and lower side straps of the positioning and stabilizing structure 3400. The annular side wall 16115 of the frame member 16100 may be releasably connected or interlocked with a retaining portion or frame interface 16250 of the cushion assembly 16175 in any suitable manner.

In an example, the frame member 16100 and the anterior wall member 16300 may be provided in one size, which may be selectively engageable with multiple sizes of cushion assemblies 16175. For example, the cushion assembly 16175 may be provided in three sizes, e.g., a small size cushion assembly 16175A as shown in FIG. 49A, a medium size cushion assembly 16175B as shown in FIG. 49B, and a large size cushion assembly 16175C as shown in FIG. 49C. As illustrated, the different size cushion assemblies include at least one aspect different from one another, e.g., different heights. As shown in FIG. 48, each main body 16180 of the different size cushion assemblies includes a retaining portion or frame interface 16250 that is common or similar for all sizes (e.g., common engagement surface along an apex and side portions of the main body 16180), which allows the one size or common frame member 16100 to be connected to each of the different size cushion assemblies, i.e., each cushion assembly includes common frame mating geometry on the frame interface 16250 for all cushion sizes. Similarly, the peripheral portion 16105 defining the void 16102 of each of the different size cushion assemblies includes a similar size and geometry, which allows the one size or common anterior wall member 16300 to be connected to each of the different size cushion assemblies. FIGS. 50A, 50B, and 50C illustrate the common frame member 16100 and the common anterior wall member 16300 engaged with each of the small, medium, and large cushion assemblies 16175A, 16175B, 16175C according to an example of the present technology.

The seal-forming structure 16200 is connected to the main body 16180 of the cushion assembly 16175, e.g., seal-forming structure 16200 co-molded to the main body 16180. As shown in FIGS. 51 to 53, the main body 16180 may include a retaining structure 16890 to receive a retaining portion 16205 of the seal-forming structure 16200, e.g., and may provide a substantially continuous internal surface defining the plenum chamber 16500. The retaining structure 16890 includes horizontal and vertical wall sections 16892, 16894 that define a space to receive the retaining portion 16205 of the seal-forming structure 16200 therein. In an example, the retaining structure includes a width w of about 2-5 mm, e.g., 3 mm. The retaining structure 16890 extends around the full perimeter of the main body 16180 which allows the horizontal wall section 16892 and its interior seal engaging surface to be maintained around the full perimeter for engagement with the retaining portion 16205.

The anterior wall member 16300 includes connection port 16302 adapted to be connected to an elbow or swivel elbow which is connected to the gas delivery tube 4180. In the illustrated example, the connection port 16302 includes grooves 16303 structured to allow a bayonet style attachment to the elbow. However, it should be appreciated that the elbow may be releasably or permanently connected to the connection port 16302 in other suitable manners.

As shown in FIGS. 43, 44, and 46, at least a peripheral portion 16305 of the anterior wall member 16300 is repeatedly engageable with and disengageable from at least the peripheral portion 16105 of the main body 16180 of the cushion assembly 16175. The perimeter, shape, and geometry of the mating surfaces provided by the peripheral portions 16305, 16105 are predetermined to facilitate alignment and mechanical/structural engagement, e.g., clean, smooth, and flat conical surfaces with minimal protrusions along leading/trailing edges to avoid interference with adjacent geometry. Adjacent geometry of the main body 16180 may be used as slip surfaces.

The anterior wall member 16300 may be secured and retained to the cushion assembly 16175 in any suitable manner. For example, as shown in FIG. 47, each side of the peripheral portion 16105 includes a tab 16110 associated with a push button 16800, which is structured to engage or interlock (e.g., with a snap-fit) with a respective tab 16804 of the anterior wall member 16300 to releasably retain the anterior wall member 16300 to the cushion assembly 16175.

A lip seal 16850 (e.g., constructed of silicone) is provided, e.g., overmolded, along the edge of the peripheral portion 16105 defining the void 16102 of the cushion assembly 16175. The lip seal 16850 provides a compression and pressure assisted seal between the cushion assembly 16175 and the anterior wall member 16300 when engaged with one another. In an example, the lip seal 16850 may extend radially inwardly from the peripheral portion 16105 into the void 16102.

When the anterior wall member 16300 and the cushion assembly 16175 are engaged, the anterior wall member 16300 seals the void 16102 of the cushion assembly 16175 and forms the gas chamber or plenum chamber. When the anterior wall member 16300 is disengaged from the cushion assembly 16175, e.g., see FIG. 45, the void 16102 of the cushion assembly 16175 is sized such that at least a portion of the patient's nose and/or mouth is exposed. The void 16102 is sized to be sufficiently larger than the connection port 13602, e.g., diameter of void 16102 about 35-50 mm, e.g., about 40 mm.

Engagement and Disengagement Process

In one form of the present technology, e.g., as shown in FIG. 17, the anterior wall member 3300 is engageable with the cushion assembly 3175 by posteriorly moving the anterior wall member 3300 towards the cushion assembly 3175 in a direction substantially parallel to the Frankfort horizontal, and the anterior wall member 3300 is disengageable from the cushion assembly 3175 by anteriorly moving the anterior wall member 3300 from the cushion assembly 3175 in a direction substantially parallel to the Frankfort horizontal.

In another example, as shown in FIGS. 18 and 19a, the anterior wall member 3300 may be engaged with the cushion assembly 3175 by first engaging the top magnets 3110a, 3310a provided along the apex of the respective peripheral portion 3105, 3305 to locate and align the tip of the anterior wall member 3300 with the cushion assembly 3175. Then the anterior wall member 3300 may be pivoting downwardly to engage the lower magnets 3110b, 3310b on opposing, lower sides of the respective peripheral portion 3105, 3305 as shown in FIG. 19b. In such example, the top apex magnets 3110a, 3310a may help to engage and locate a mechanical engagement, e.g., snap-fit connection, between the anterior wall member 3300 with the cushion assembly 3175, and the lower side magnets 3110b, 3310b may help to engage and locate a mechanical engagement, e.g., snap fit connection, between the anterior wall member 3300 with the cushion assembly 3175.

However, it is envisaged that the patient may engage the anterior wall member 3300 to the cushion assembly 3175 without any pivoting or tilting of the anterior wall member 3300 downwardly relative to the cushion assembly 3175, or pivoting may be in an upwardly or sideways direction.

In another example, as shown in FIG. 19c, the anterior wall member 3300 may be engaged with the cushion assembly 3175 by first engaging magnets 3310, 3110 provided on one lateral side of the anterior wall member/cushion assembly, and then pivoting the anterior wall member 3300 to engage magnets 3310, 3110 provided on the opposing lateral side of the anterior wall member/cushion assembly, e.g., left-right attachment.

In an example, the cushion assembly 3175 and frame member 3100 connected thereto is first positioned against the patient's face using the positioning and stabilizing structure 3400, and then the anterior wall member 3300 is engaged with the cushion assembly 3175 to seal the void 3102 of the cushion assembly 3175. A sealing lip or pressure activated seal may provide a pneumatic seal between the anterior wall member 3300 and cushion assembly 3175. An exemplary method of donning the patient interface 3000 includes positioning the cushion assembly 3175 including the seal-forming structure 3200 and frame member 3100 connected thereto against the patient's face using the positioning and stabilizing structure 3400 and engaging the anterior wall member 3300 having a predetermined surface area with the cushion assembly 3175 to seal the void 3102 of the cushion assembly 3175 and form the gas chamber 3500.

Connection Between Cushion Assembly and Frame Member

In the illustrated example, the cushion assembly 3175 and the frame member 3100 include cooperating retaining structures to connect the cushion assembly 3175 to the frame member 3100. In an example, the frame member 3100 is releasably connectable to the cushion assembly 3175 to facilitate replacement and/or cleaning, and to allow alternative frame members and cushion assemblies to be connected to one another. Such arrangement allows multiple seals (e.g., types and sizes) to be used with the patient interface and therefore provide a patient interface suitable for Multiple Patient Multiple Use (MPMU) usage situations. In an alternative example, the frame member 3100 may be permanently connected or integrally formed in one-piece with the cushion assembly 3175, e.g., co-molded.

In the illustrated example shown in FIG. 11a, the frame member 3100 includes an open construction with an annular side wall 3115 to receive and retain the cushion assembly 3175 thereto. The cushion assembly 3175 is engaged with the frame member 3100 such that the annular side wall 3115 encloses or wraps around the cushion assembly 3175, and at least a portion of the cushion assembly 3175 passes through the frame member 3100, i.e., the seal-forming structure 3200 and the peripheral portion 3105 of the main body 3180 are provided on opposite sides of the frame member 3100. Such arrangement allows the peripheral portion 3105 of the cushion assembly 3175 to project from the frame member 3100 and be sufficiently exposed for engagement with the anterior wall member 3300. Also, connection of the frame member 3100 about the periphery of the cushion assembly 3175 may facilitate a more even transfer of sealing force to the cushion assembly 3175 from the positioning and stabilising structure 3400.

As shown in FIGS. 11a and 11b, the annular side wall 3115 includes a pair of upper retention features structured to engage or interlock with corresponding retention features provided to an upper portion (e.g., apex) of the cushion assembly 3175. In the illustrated example, the upper retention features include a pair of inwardly projecting beads or protrusions 3117 structured to engage or interlock with corresponding recesses 3182 provided to the cushion assembly 3175. Also, the cushion assembly 3175 includes elongated protrusions 3184 on opposing, lower sides thereof structured to engage or interlock with opposing lower sides of the annular side wall 3115, e.g., elongated protrusions 3184 act as a catch to retain lower sides of the annular side wall 3115 on the cushion assembly 3175. However, it should be appreciated that the cushion assembly 3175 may be connected or interlocked with the frame member 3100 in other suitable manners.

Connection Port

In the illustrated example, the anterior wall member 3300 comprises a connection port 3302 for connection to a gas delivery tube. As illustrated, the connection port 3302 is connected to an elbow or swivel elbow 3600. In an example, as shown in FIGS. 10, 11a, and 11b, the elbow 3600 includes first end portion 3602 connected to the connection port 3302 and a second end portion 3604 adapted to connect to a short tube 4180 of the air circuit 4170, e.g., via swivel connector 3605. The swivel elbow 3600 and anterior wall member 3300 may form a permanent assembly, or the swivel elbow 3600 and anterior wall member 3300 may be removably coupled to one another.

In an alternative example, the cushion assembly 3175 may comprise a connection port 3302 for connection to a gas delivery tube 4180.

In an alternative example, as shown in FIG. 30, the gas delivery tube (e.g., short tube 4180) may be directly connected or otherwise provided to the connection port 3302 without the use of an elbow or swivel elbow. For example, the gas delivery tube (e.g., short tube 4180) may be directly connected to the connection port 3302 of the anterior wall member 3300. The gas delivery tube 4180 may be permanently or removably connected to the connection port 3302. Permanent connection may be by way of overmolding or mechanical interlock.

Vent

In one form of the present technology, the patient interface 3000 may include a vent 3700 constructed and arranged to allow for the washout of exhaled air (including carbon dioxide). The vent 3700 is not bulky, i.e., not thick or protrude significantly in the anterior and/or posterior direction. The vent 3700 directs exhaust air away from the cushion assembly 3175 and plenum chamber 3500.

Referring to FIGS. 10, 11a, and 11b, one form of vent 3700 in accordance with the present technology comprises a plurality of very small holes 3705, in other words, a multi-hole vent 3700. Two or more multi-hole vents 3700 may be provided to the patient interface 3000.

In the illustrated example, the vent 3700 is integrated into the anterior wall member 3300 and is implemented as an array of at least thirty (30) vent holes, e.g., at least 40 vent holes 3705, that ring around the connection port 3302, e.g., see FIGS. 10, 11a, and 11b. In other words, the vent 3700 has a substantially circular shape. That is, the anterior wall member 3300 has a multi-hole vent 3700 radially disposed around the connection port 3302 connected to the swivel elbow 3600. The individual vent holes 3705 are shaped so as to diffuse the exhaust air (i.e., not directional) thereby reducing the exhaust noise and effects of "air jetting", whilst providing adequate $CO_2$ washout, for example, tapered vent holes 3705.

In an alternative example, at least one vent 3700 may be provided on the swivel elbow 3600 or the cushion assembly 3175 to allow the washout of air.

In another example, the vent 3700 may be made from a textile formed of interlaced plastic fibers, e.g., mesh vent.

Seal-Forming Structure

In one form of the present technology, the seal-forming structure 3200 is permanently connected to the main body 3180 of the cushion assembly 3175, e.g., the seal-forming structure 3200 is co-molded to the main body 3180.

In another form of the present technology, the seal-forming structure 3200 may include a retaining structure to connect the seal-forming structure 3200 to the main body 3180. For example, the retaining structure (e.g., constructed of a relatively hard plastic material) may be in the form of a retaining clip structured to releasably connect to the main body 3180 with a snap-fit and provide the seal-forming structure 3200 with a hard-to hard connection with the main body 3180.

In the example shown in FIGS. 4 to 14, 17, 18, 20a, 20b, and 21, the seal-forming structure 3200 is of a first type structured to serve the patient's nose and mouth. For example, the seal-forming structure 3200 may be a full-face/oro-nasal cushion structured to form a seal around the patient's nose and mouth.

In an alternative example, the seal-forming structure 3200 is of a second type structured to only serve the patient's nares. For example, the seal-forming structure 3200 may be a nasal cushion or nasal cradle structured to form a seal around both nares without being partially located inside the nose. In another example, the seal-forming structure 3200 may include nasal pillows or nasal prongs structured to form a seal surrounding or with the patient's nares (e.g., see FIGS. 26 to 29).

For example, FIGS. 24a and 24b illustrate a patient interface 7000 including a frame member 7100, a seal-forming member 7200 (e.g., nasal cushion) co-molded or otherwise attached to the frame member 7100, and an anterior wall member 7300 (with elbow 7600) magnetically attachable to the frame member 7100 via respective magnets 7310, 7110. In an example, as shown in FIG. 24b, a cushion clip 7205 is provided (e.g., co-molded) to the seal-forming member 7200, which cushion clip 7205 allows the seal-forming member 7200 to be releasably attached to the frame member 7100. In an example, the elbow 7600 may swivel and/or flex relative to the anterior wall member 7300. In an alternative form, the gas delivery tube may be coupled directly to the anterior wall member 7300 without an elbow. In this example, the seal-forming member 7200 is in the form of a nasal cushion structured to form a seal around the patient's nose. Also, the patient interface 7000 may be structured to house an optional and replaceable heat and moisture exchanger (HME/HMX) cartridge 7750 to provide sufficient heat and humidity to the patient during therapy.

In another example, as shown in FIGS. 25a and 25b, the frame member 7100 and the anterior wall member 7300 may include a generally circular interface, e.g., frame member 7100 and anterior wall member 7300 provide generally circular magnets 7110, 7310 which provide a magnetic ring connection that allows swiveling between the frame member 7100 and the anterior wall member 7300. In an example, a cushion clip 7205 may be provided (e.g., co-molded) to the seal-forming member 7200, which cushion clip 7205 allows the seal-forming member 7200 to be releasably attached to the frame member 7100. However, it should be appreciated that the seal-forming member 7200 may be attached to the frame member 7100 in other suitable manners.

FIGS. 26a and 26b show another example of a patient interface 8000 including a frame member 8100, a seal-forming member 8200 co-molded or otherwise attached to the frame member 8100, and an anterior wall member 8300 (with elbow 8600) magnetically attachable to the frame member 8100 via respective magnets 8310, 8110. In this example, the seal-forming member 8200 is in the form of nasal pillows structured to form a seal surrounding or with the patient's nares. In an example, a cushion clip 8205 may be provided (e.g., co-molded) to the seal-forming member 8200, which cushion clip 8205 allows the seal-forming member 8200 to be releasably attached to the frame member 8100. However, it should be appreciated that the seal-forming member 8200 may be attached to the frame member 8100 in other suitable manners.

As shown in FIGS. 27 and 28, the frame member 8100 may be attachable to the anterior wall member 8300 in other manners, e.g., mechanical interlock used in combination with magnetic engagement. In FIG. 27, a snap-fit connector 8311 is used along with magnet 8310 to attach the anterior wall member 8300 to the frame member 8100. In FIG. 28, an alternative snap-fit connector 8313 is used along with magnet 8310 to attach the anterior wall member 8300 to the frame member 8100. In each example, a cushion clip 8205 may be provided (e.g., co-molded) to the seal-forming member 8200, which cushion clip 8205 allows the seal-forming member 8200 to be releasably attached to the frame member 8100. However, it should be appreciated that the seal-forming member 8200 may be attached to the frame member 8100 in other suitable manners.

In yet another example, as shown in FIG. 29, each connector may provide a mechanical interlock along with a magnet. As illustrated, the anterior wall member 8300 includes a snap-fit connector 8315 provided with a magnet 8310, and the frame member 8100 includes a connector provided with a magnet 8110. In an example, a cushion clip 8205 may be provided (e.g., co-molded) to the seal-forming member 8200, which cushion clip 8205 allows the seal-forming member 8200 to be releasably attached to the frame member 8100. However, it should be appreciated that the seal-forming member 8200 may be attached to the frame member 8100 in other suitable manners. In another example, the snap-fit connector 8315 and the connector of the frame member 8100 may not be provided with magnets, and the anterior wall member 8300 may be secured to the frame member 8100 only mechanically.

In one form of the present technology, the seal-forming structure 3200 provides a sealing-forming surface, and may additionally provide a cushioning function. A seal-forming structure 3200 of the non-invasive patient interface 3000 in accordance with the present technology may be constructed from a soft, flexible, resilient material such as silicone. However, the seal-forming structure 3200 may comprise other materials, e.g., foam and/or gel and/or low durometer silicone.

In one form of the present technology, the patient interface 3000 may provide a modular system including a single anterior wall member or fascia which is attachable to or otherwise structured to interface with frame members, cushion assemblies, and/or seal-forming structures of multiple types, sizes and/or interface types. For example, cushion assemblies having different seal-forming structures may be attachable to a common frame member and also allow attachment to the single anterior wall member or fascia.

Forehead Support

In one form of the present technology, the patient interface 3000 includes a forehead support. In the illustrated example shown in FIGS. 4-14, the frame member 3100 includes a forehead support 3150.

The forehead support 3150 includes upper headgear connectors 3152 adapted to connect to upper side straps 3402 of the positioning and stabilizing structure 3400 (e.g., see FIGS. 4 to 9). The frame member 3100 comprises lower headgear connectors 3120 adapted to connect to lower side straps 3404 of the positioning and stabilizing structure 3400 (e.g., see FIGS. 4 to 9).

In one alternative form, the patient interface 3000 does not include a forehead support. For example, FIGS. 23 to 28 illustrate examples of patient interfaces that do not include a forehead support.

For example, FIG. 23 illustrates a patient interface 6000 including a frame member 6100, a cushion assembly 6175 including a seal-forming member 6200 replaceably attached to the frame member 6100 via a retaining structure 6250, and an anterior wall member 6300 (with elbow 6600) magnetically attachable to the frame member 6100 via respective magnets 6310, 6110. In this example, the frame member 6100 includes upper headgear connectors 6152 and lower headgear connectors 6120 adapted to connect to upper and lower side straps 3402, 3404 of the positioning and stabilizing structure 3400.

FIGS. 31 to 33 show an alternative example in which an alternative frame member 13100 is provided to the cushion assembly 3175. In this example, the frame member 13100 does not include a forehead support. As illustrated, the frame member 13100 includes an annular side wall 13115 with upper headgear connectors 13152 and lower headgear connectors 13120 adapted to connect to upper and lower side straps of the positioning and stabilizing structure 3400. Similar to the example described above, the frame member 13100 is releasably connected to the cushion assembly 3175, e.g., by engaging a pair of inwardly projecting beads or protrusions 13117 with corresponding recesses 3182 provided to the cushion assembly 3175 and engaging lower sides of the annular side wall 13115 with respective protrusions 3184 provided to the cushion assembly 3175. However, it should be appreciated that the cushion assembly 3175 may be connected or interlocked with the frame member 13100 in other suitable manners.

As best shown in FIG. 33, the peripheral portion 3105 of the cushion assembly 3175 projects from the frame member 13100 to be sufficiently exposed for releasable engagement with the anterior wall member 3300.

Positioning and Stabilising Structure

Note that in one form of the present technology, a number of structural features form part of a positioning and stabilising structure 3400, e.g., a headgear assembly (which may be referred to simply as headgear). In an alternative form of the present technology, one or more of those features are located on or permanently attached to the frame 3100 or retaining structure of the cushion assembly.

The seal-forming structure 3200 of the patient interface 3000 of the present technology may be held in sealing position in use by the positioning and stabilising structure 3400 (FIGS. 4 to 9). In one form, the positioning and stabilising structure 3400 comprises headgear. It should be appreciated that the positioning and stabilising structure 3400 may, in one form of the technology, be referred to as headgear.

The positioning and stabilising structure 3400 may comprise two pairs of side straps, i.e., a pair of upper side straps 3402 and a pair of lower side straps 3404, connected to a circular crown strap 3406 that encapsulates the crown of the patient's head. Headgear straps to anchor and maintain the cushion assembly on the patient's face provides a suitable arrangement to comfortably handle tube torque from the gas delivery tube.

The upper side straps 3402 connect to the upper headgear connectors 3152 of the forehead support 3150 and the lower side straps 3404 connect to the lower headgear connectors 3120 of the frame member 3100. The side straps 3402, 3404 may include an adjustable hook and loop (Velcro™) connection mechanism, e.g., Velcro™-like hook tabs, to facilitate connection and/or adjustment to the headgear connectors 3152, 3120.

3.4 Pap Device 4000

A PAP device 4000 in accordance with one aspect of the present technology comprises mechanical and pneumatic components 4100, electrical components 4200 and is programmed to execute one or more algorithms. The PAP device may have an external housing 4010, formed in two parts, an upper portion 4012 of the external housing 4010, and a lower portion 4014 of the external housing 4010. In alternative forms, the external housing 4010 may include one or more panel(s) 4015. The PAP device 4000 may comprise a chassis 4016 that supports one or more internal components of the PAP device 4000. In one form a pneumatic block 4020 is supported by, or formed as part of the chassis 4016. The PAP device 4000 may include a handle 4018.

The pneumatic path of the PAP device 4000 may comprise an inlet air filter 4112, an inlet muffler, a controllable pressure device capable of supplying air at positive pressure (e.g., a controllable blower 4142), and an outlet muffler. One or more pressure sensors and flow sensors may be included in the pneumatic path.

The pneumatic block 4020 may comprise a portion of the pneumatic path that is located within the external housing 4010.

The PAP device 4000 may have an electrical power supply 4210 and one or more input devices 4220. Electrical components 4200 may be mounted on a single Printed Circuit Board Assembly (PCBA) 4202. In an alternative form, the PAP device 4000 may include more than one PCBA 4202.

3.4.1 Pap Device Mechanical & Pneumatic Components 4100

3.4.1.1 Air Filter(s) 4110

A PAP device 4000 in accordance with one form of the present technology may include an air filter 4110, or a plurality of air filters 4110.

In one form, an inlet air filter 4112 is located at the beginning of the pneumatic path upstream of a controllable blower 4142. See FIG. 3c.

In one form, an outlet air filter 4114, for example an antibacterial filter, is located between an outlet of the pneumatic block 4020 and a patient interface 3000. See FIG. 3c.

3.4.1.2 Pressure Device 4140

In a form of the present technology, a pressure device for producing a flow of air at positive pressure is a controllable blower 4142. For example the blower 4142 may include a brushless DC motor with one or more impellers housed in a volute. The blower 4142 may be capable of delivering a supply of air, for example about 120 litres/minute, at a positive pressure in a range from about 4 cmH$_2$O to about 20 cmH$_2$O, or in other forms up to about 30 cmH$_2$O.

3.5 Humidifier 5000

3.5.1 Humidifier Overview

In one form of the present technology there is provided a humidifier 5000, as shown in FIG. 3b, that may comprise a water reservoir and a heating plate.

3.6 Glossary

In certain forms of the present technology, one or more of the following definitions may apply. In other forms of the present technology, alternative definitions may apply.

3.6.1 General

Air: Air will be taken to include breathable gases, for example air with supplemental oxygen.

Continuous Positive Airway Pressure (CPAP): CPAP treatment will be taken to mean the application of a supply of air or breathable gas to the entrance to the airways at a pressure that is continuously positive with respect to atmosphere, and preferably approximately constant through a respiratory cycle of a patient. In some forms, the pressure at the entrance to the airways will vary by a few centimeters of water within a single respiratory cycle, for example being higher during inhalation and lower during exhalation. In some forms, the pressure at the entrance to the airways will be slightly higher during exhalation, and slightly lower during inhalation. In some forms, the pressure will vary between different respiratory cycles of the patient, for example being increased in response to detection of indications of partial upper airway obstruction, and decreased in the absence of indications of partial upper airway obstruction.

3.6.2 Aspects of PAP Devices

Air circuit: A conduit or tube constructed and arranged in use to deliver a supply of air or breathable gas between a PAP device and a patient interface. In particular, the air circuit may be in fluid connection with the outlet of the pneumatic block and the patient interface. The air circuit may be referred to as air delivery tube. In some cases there may be separate limbs of the circuit for inhalation and exhalation. In other cases a single limb is used.

Blower or flow generator: A device that delivers a flow of air at a pressure above ambient pressure.

Controller: A device, or portion of a device that adjusts an output based on an input. For example one form of controller has a variable that is under control—the control variable—that constitutes the input to the device. The output of the device is a function of the current value of the control variable, and a set point for the variable. A servo-ventilator may include a controller that has ventilation as an input, a target ventilation as the set point, and level of pressure support as an output. Other forms of input may be one or more of oxygen saturation (SaO2), partial pressure of carbon dioxide (PCO2), movement, a signal from a photoplethysmogram, and peak flow. The set point of the controller may be one or more of fixed, variable or learned. For example, the set point in a ventilator may be a long term average of the measured ventilation of a patient. Another ventilator may have a ventilation set point that changes with time. A pressure controller may be configured to control a blower or pump to deliver air at a particular pressure.

Therapy: Therapy in the present context may be one or more of positive pressure therapy, oxygen therapy, carbon dioxide therapy, control of dead space, and the administration of a drug.

Positive Airway Pressure (PAP) device: A device for providing a supply of air at positive pressure to the airways.

3.6.3 Anatomy of the Face

Ala: the external outer wall or "wing" of each nostril (plural: alar)

Alare: The most lateral point on the nasal ala.

Alar curvature (or alar crest) point: The most posterior point in the curved base line of each ala, found in the crease formed by the union of the ala with the cheek.

Auricula or Pinna: The whole external visible part of the ear.

(nose) Bony framework: The bony framework of the nose comprises the nasal bones, the frontal process of the maxillae and the nasal part of the frontal bone.

(nose) Cartilaginous framework: The cartilaginous framework of the nose comprises the septal, lateral, major and minor cartilages.

Columella: the strip of skin that separates the nares and which runs from the pronasale to the upper lip.

Columella angle: The angle between the line drawn through the midpoint of the nostril aperture and a line drawn perpendicular to the Frankfurt horizontal while intersecting subnasale.

Frankfort horizontal plane: A line extending from the most inferior point of the orbital margin to the left tragion. The tragion is the deepest point in the notch superior to the tragus of the auricle.

Glabella: Located on the soft tissue, the most prominent point in the midsagittal plane of the forehead.

Lateral nasal cartilage: A generally triangular plate of cartilage. Its superior margin is attached to the nasal bone and frontal process of the maxilla, and its inferior margin is connected to the major alar cartilage.

Major alar cartilage: A plate of cartilage lying below the lateral nasal cartilage. It is curved around the anterior part of the naris. Its posterior end is connected to the frontal process of the maxilla by a tough fibrous membrane containing three or four minor cartilages of the ala.

Nares (Nostrils): Approximately ellipsoidal apertures forming the entrance to the nasal cavity. The singular form of nares is naris (nostril). The nares are separated by the nasal septum.

Naso-labial sulcus or Naso-labial fold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: the most protruded point or tip of the nose, which can be identified in lateral view of the rest of the portion of the head.

Philtrum: the midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronasale.

Sagittal plane: A vertical plane that passes from anterior (front) to posterior (rear) dividing the body into right and left halves.

Sellion: Located on the soft tissue, the most concave point overlying the area of the frontonasal suture.

Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramentale: The point of greatest concavity in the midline of the lower lip between labrale inferius and soft tissue pogonion.

3.6.4 Anatomy of the Skull

Frontal bone: The frontal bone includes a large vertical portion, the squama frontalis, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama occipitalis.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

3.6.5 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx), the oropharynx (mesopharynx), and the laryngopharynx (hypopharynx).

3.6.6 Materials

Silicone or Silicone Elastomer: A synthetic rubber. In this specification, a reference to silicone is a reference to liquid silicone rubber (LSR) or a compression molded silicone rubber (CMSR). One form of commercially available LSR is SILASTIC (included in the range of products sold under this trademark), manufactured by Dow Corning. Another manufacturer of LSR is Wacker. Unless otherwise specified to the contrary, a preferred form of LSR has a Shore A (or Type A) indentation hardness in the range of about 35 to about 45 as measured using ASTM D2240.

Polycarbonate: a typically transparent thermoplastic polymer of Bisphenol-A Carbonate.

3.6.7 Aspects of a Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: A conduit that directs an axis of flow or air to change direction through an angle. In one form, the angle may be approximately 90 degrees. In another form, the angle may be less than 90 degrees. The conduit may have an approximately circular cross-section. In another form the conduit may have an oval or rectangular cross-section.

Frame: Frame will be taken to mean a mask structure that bears the load of tension between two or more points of connection with a headgear. A mask frame may be a non-airtight load bearing structure in the mask. However, some forms of mask frame may also be air-tight.

Functional dead space: The functional dead space refers to at least one region within a breathing circuit where a patient's exhalate may collect such that the normal flow of gas within the breathing circuit cannot effectively flush the exhalate from the breathing circuit.

Headgear: Headgear will be taken to mean a form of positioning and stabilizing structure designed for use on a head. Preferably the headgear comprises a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to a mean portion of a patient interface having walls enclosing a volume of space, the volume having air therein pressurised above atmospheric pressure in use. A shell may form part of the walls of a mask plenum chamber. In one form, a region of the patient's face forms one of the walls of the plenum chamber.

Seal: The noun form ("a seal") will be taken to mean a structure or barrier that intentionally resists the flow of air through the interface of two surfaces. The verb form ("to seal") will be taken to mean to resist a flow of air.

Shell: A shell will preferably be taken to mean a curved structure having bending, tensile and compressive stiffness, for example, a portion of a mask that forms a curved structural wall of the mask. Preferably, compared to its overall dimensions it is relatively thin. In some forms, a shell may be faceted. Preferably such walls are airtight, although in some forms they may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel: (noun) A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. Preferably there is little or no leak flow of air from the swivel in use.

Tie: A tie will be taken to be a structural component designed to resist tension.

Vent: (noun) the structure that allows a deliberate controlled rate leak of air from an interior of the mask, or conduit to ambient air, to allow washout of exhaled carbon dioxide ($CO_2$) and supply of oxygen ($O_2$).

3.6.8 Terms Used in Relation to Patient Interface

Curvature (of a surface): A region of a surface having a saddle shape, which curves up in one direction and curves down in a different direction, will be taken to have a negative curvature. A region of a surface having a dome shape, which curves the same way in two principle directions, will be taken to have a positive curvature. A flat surface will be taken to have zero curvature.

Floppy: A quality of a material, structure or composite that is the combination of features of:
  Readily conforming to finger pressure.
  Unable to retain its shape when caused to support its own weight.
  Not rigid.
  Able to be stretched or bent elastically with little effort.

The quality of being floppy may have an associated direction, hence a particular material, structure or composite may be floppy in a first direction, but stiff or rigid in a second direction, for example a second direction that is orthogonal to the first direction.

Resilient: Able to deform substantially elastically, and to release substantially all of the energy upon unloading, within a relatively short period of time such as 1 second.

Rigid: Not readily deforming to finger pressure, and/or the tensions or loads typically encountered when setting up and maintaining a patient interface in sealing relationship with an entrance to a patient's airways.

Semi-rigid: means being sufficiently rigid to not substantially distort under the effects of mechanical forces typically applied during positive airway pressure therapy.

3.7 Other Remarks

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

It must be noted that as used herein and in the appended claims, the singular forms "a", "an", and "the" include their plural equivalents, unless the context clearly dictates otherwise.

Moreover, in interpreting the disclosure, all terms should be interpreted in the broadest reasonable manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

While the present technology has been described in connection with what are presently considered to be the most practical and preferred examples, it is to be understood that the technology is not to be limited to the disclosed examples, but on the contrary, is intended to cover various modifications and equivalent arrangements included within the spirit and scope of the technology. Also, the various examples described above may be implemented in conjunction with other examples, e.g., aspects of one example may be combined with aspects of another example to realize yet other examples. Further, each independent feature or component of any given assembly may constitute an additional example.

3.8 Reference Signs List

| Number | Feature Item |
| --- | --- |
| 302 | conventional connection port |
| 1000 | patient |
| 1100 | bed partner |
| 3000 | patient interface |
| 3100 | frame member |
| 3102 | void |
| 3104 | anterior facing surface |
| 3105 | peripheral portion |
| 3110 | magnet |
| 3115 | annular side wall |
| 3117 | beads |
| 3120 | lower headgear connector |
| 3150 | forehead support |
| 3152 | upper headgear connector |
| 3175 | cushion assembly |
| 3180 | main body |
| 3182 | recesses |
| 3184 | protrusions |
| 3200 | seal-forming structure |
| 3300 | anterior wall member |
| 3302 | connection port |
| 3303 | posterior facing surface |
| 3305 | peripheral portion |
| 3310 | magnet |
| 3400 | positioning and stabilizing structure |
| 3402 | upper side straps |
| 3404 | lower side straps |
| 3406 | crown strap |
| 3500 | plenum chamber |
| 3600 | swivel elbow |
| 3602 | first end portion |
| 3604 | second end portion |
| 3605 | swivel connector |
| 3700 | vent |
| 3705 | vent holes |
| 3750 | HME/HMX cartridge |
| 4000 | PAP device |
| 4010 | housing |
| 4012 | upper portion |
| 4014 | lower portion |
| 4015 | panels |
| 4016 | chassis |
| 4018 | handle |
| 4020 | pneumatic block |
| 4100 | mechanical and pneumatic components |
| 4110 | filter |
| 4112 | filter |
| 4114 | filter |
| 4142 | blower |
| 4170 | gas delivery tube |
| 4180 | gas delivery tube |
| 4190 | adaptor |
| 4200 | electrical components |
| 4202 | PCBA |
| 4210 | power supply |
| 4220 | input devices |
| 5000 | humidifier |
| 6000 | patient interface |
| 6100 | frame member |
| 6110 | magnet |
| 6120 | lower headgear connectors |
| 6152 | upper headgear connectors |
| 6175 | cushion assembly |
| 6200 | seal-forming member |
| 6250 | retaining structure |
| 6300 | anterior wall member |
| 6310 | magnet |
| 6600 | elbow |
| 7000 | patient interface |
| 7100 | frame member |
| 7110 | magnet |
| 7200 | seal-forming member |
| 7205 | cushion clip |
| 7300 | anterior wall member |
| 7310 | magnet |
| 7600 | elbow |
| 7750 | HME/HMX cartridge |
| 8000 | patient interface |
| 8100 | frame member |
| 8110 | magnet |
| 8200 | seal-forming member |
| 8205 | cushion clip |
| 8300 | anterior wall member |
| 8310 | magnet |
| 8311 | snap-fit connector |
| 8313 | snap-fit connector |
| 8315 | snap-fit connector |
| 8600 | elbow |
| 13100 | frame member |
| 13115 | annular side wall |
| 13117 | beads |
| 13120 | lower headgear connectors |
| 13152 | upper headgear connectors |
| 14000 | patient interface |
| 14100 | frame member |
| 14102 | void |
| 14105 | peripheral portion |
| 14110 | tab or catch |
| 14115 | annular side wall |
| 14120 | lower headgear connectors |
| 14152 | upper headgear connectors |
| 14175 | cushion assembly |
| 14180 | main body |
| 14200 | seal-forming structure |
| 14250 | retaining portion |
| 14300 | anterior wall member |
| 14302 | connection port |
| 14303 | grooves |
| 14800 | push button |
| 14802 | grooves |
| 14804 | tab or catch |
| 14820 | raised portion |
| 14830 | webbing |
| 14850 | lip seal |
| 15175 | cushion assembly |
| 15180 | main body |
| 15800 | push button |
| 16000 | patient interface |

-continued

| Number | Feature Item |
|---|---|
| 16100 | frame member |
| 16102 | void |
| 16105 | peripheral portion |
| 16110 | tab |
| 16115 | annular side wall |
| 16120 | lower headgear connectors |
| 16152 | upper headgear connectors |
| 16175 | cushion assembly |
| 16175A | small cushion assembly |
| 16175B | medium cushion assembly |
| 16175C | large cushion assembly |
| 16180 | main body |
| 16200 | seal-forming structure |
| 16205 | retaining portion |
| 16250 | retaining portion |
| 16300 | anterior wall member |
| 16302 | connection port |
| 16303 | grooves |
| 16305 | peripheral portion |
| 16800 | push button |
| 16804 | tab |
| 16850 | lip seal |
| 16890 | retaining structure |
| 16892 | horizontal wall section |
| 16894 | vertical wall section |

The invention claimed is:

1. A patient interface for delivery of a supply of pressurised air or breathable gas to an entrance of a patient's airways for treatment of sleep disordered breathing, the patient interface comprising:
a frame member including a main body and a pair of headgear connector arms extending from the main body;
a cushion assembly provided to the frame member, wherein the cushion assembly includes a seal-forming structure constructed and arranged to form a seal with a patient's nose and/or mouth, and wherein the cushion assembly forms a void;
headgear to maintain the patient interface in position on a patient's head, the headgear including a pair of headgear straps adapted to connect to a respective one of the pair of headgear connector arms of the frame member; and
an anterior wall member repeatedly engageable with and disengageable from the frame member, the anterior wall member having a predetermined surface area to seal the void of the cushion assembly and form a gas chamber when the anterior wall member and the frame member are engaged,
wherein the anterior wall member and the frame member are magnetically engageable, and
wherein the void of the cushion assembly is sized such that the patient's nose and/or mouth is substantially exposed when the anterior wall member is disengaged from the frame member thereby improving breathing comfort of the patient.

2. The patient interface of claim 1, wherein the anterior wall member comprises a connection port for connection to a gas delivery tube.

3. The patient interface of claim 2, wherein the connection port is connected to an elbow operatively connected to the gas delivery tube.

4. The patient interface of claim 2, wherein the gas delivery tube is permanently connected to the connection port.

5. The patient interface of claim 1, wherein the seal-forming structure comprises a full-face cushion, a nasal cushion, or nasal pillows.

6. The patient interface of claim 1, wherein at least a peripheral portion of the anterior wall member is repeatedly engageable with and disengageable from at least a peripheral portion of the frame member.

7. The patient interface of claim 6, wherein the peripheral portion of the anterior wall member and the peripheral portion of the frame member are rigid such that engagement between the peripheral portion of the anterior wall member and the peripheral portion of the frame member is not caused by material deformation of the anterior wall member and/or the frame member.

8. The patient interface of claim 7, wherein the peripheral portion of the anterior wall member and the peripheral portion of the frame member are magnetically engageable.

9. The patient interface of claim 8, wherein the peripheral portion of the anterior wall member and the peripheral portion of the frame member has at least one magnet.

10. The patient interface of claim 9, wherein the at least one magnet is a permanent magnet or an electromagnet.

11. The patient interface of claim 6, wherein the peripheral portion of the anterior wall member and the peripheral portion of the frame member are relatively rigid such that engagement between the peripheral portion of the anterior wall member and the peripheral portion of the frame member provide a hard-to-hard connection.

12. The patient interface of claim 1, wherein the cushion assembly is releasably connected to the frame member.

13. The patient interface of claim 1, wherein the frame member does not include a forehead support.

14. The patient interface of claim 1, wherein each of the pair of headgear connector arms curves posteriorly from the main body so each of the pair of headgear connector arms curves is adapted to extend below a respective one of the patient's eyes.

15. The patient interface of claim 1, wherein the void includes a height or diameter greater than 22 mm.

16. The patient interface of claim 1, wherein the anterior wall member is ring-shaped or disk-shaped.

17. The patient interface of claim 1, wherein the void is sized to be sufficiently larger than a connection port for connection to a gas delivery tube.

18. The patient interface of claim 1, further comprising a detachable heat and moisture exchanger cartridge positioned within the gas chamber.

19. The patient interface of claim 1, wherein the pair of headgear connector arms provide upper headgear connectors, and the frame member further comprises a pair of lower headgear connectors adapted to connect to a respective one of a pair of lower headgear straps of the headgear.

20. The patient interface of claim 1, wherein the main body of the frame member comprises an annular or ring style side wall.

* * * * *